(12) United States Patent
Main et al.

(10) Patent No.: US 11,085,046 B2
(45) Date of Patent: Aug. 10, 2021

(54) COMPOSITIONS AND METHODS FOR PRODUCTION OF MYRCENE

(71) Applicant: AMYRIS, INC., Emeryville, CA (US)

(72) Inventors: Andrew Main, Emeryville, CA (US); Grzegorz Wojciechowski, Emeryville, CA (US); Yue Yang, Emeryville, CA (US); Lishan Zhao, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 226 days.

(21) Appl. No.: 15/771,888

(22) PCT Filed: Oct. 28, 2016

(86) PCT No.: PCT/US2016/059584
§ 371 (c)(1),
(2) Date: Apr. 27, 2018

(87) PCT Pub. No.: WO2017/075538
PCT Pub. Date: May 4, 2017

(65) Prior Publication Data
US 2019/0382773 A1     Dec. 19, 2019

Related U.S. Application Data

(60) Provisional application No. 62/248,240, filed on Oct. 29, 2015.

(51) Int. Cl.
*C12N 1/14* (2006.01)
*C12N 1/16* (2006.01)
(Continued)

(52) U.S. Cl.
CPC ............... *C12N 15/52* (2013.01); *C12N 1/14* (2013.01); *C12N 1/16* (2013.01); *C12N 1/20* (2013.01);
(Continued)

(58) Field of Classification Search
None
See application file for complete search history.

(56) References Cited

U.S. PATENT DOCUMENTS

2010/0311065 A1* 12/2010 Ubersax ................. C12N 15/52
435/6.14
2012/0276637 A1   11/2012 Zhou et al.
(Continued)

FOREIGN PATENT DOCUMENTS

WO       WO 99/02030 A1    1/1999
WO       WO 2009/036067 A2 3/2009

OTHER PUBLICATIONS

Gen Bank Accession No. AAV63791.1, published Nov. 20, 2004 (Year: 2004).*
Gen Bank Accession No. AAV63790.1, published Nov. 20, 2004 (Year: 2004).*
Gen Bank Accession No. ABD77417.1, published Nov. 1, 2006 (Year: 2006).*

(Continued)

*Primary Examiner* — Richard C Ekstrom
(74) *Attorney, Agent, or Firm* — Squire Patton Boggs (US) LLP

(57) ABSTRACT

Provided herein are compositions and methods for producing myrcene by culturing genetically modified microbial host cells that express a myrcene synthase and optionally a geranyl pyrophosphate synthase. Also provided herein are isolated nucleic acid molecules that encode myrcene synthase variants derived from the *Ocimum* species myrcene synthase, which comprise one or more amino acid substitutions that improve in vivo performance of myrcene synthase in genetically modified microbial host cells. Also provided herein are isolated myrcene synthase variants that exhibit an improved activity for converting geranyl diphosphate into myrcene.

24 Claims, 9 Drawing Sheets

Specification includes a Sequence Listing.

(51) Int. Cl.
  *C12N 1/20*       (2006.01)
  *C12N 15/52*      (2006.01)
  *C12P 5/00*       (2006.01)

(52) U.S. Cl.
  CPC ....... *C12P 5/007* (2013.01); *C12Y 205/01029* (2013.01); *C12Y 402/03015* (2013.01)

(56) References Cited

U.S. PATENT DOCUMENTS

| | | | | |
|---|---|---|---|---|
| 2013/0143291 A1* | 6/2013 | McDaniel | ............ | C12N 9/1085 435/166 |
| 2015/0225754 A1* | 8/2015 | Tange | ................. | C12P 5/026 435/61 |
| 2019/0382773 A1* | 12/2019 | Main | ................. | C12P 5/007 |

OTHER PUBLICATIONS

Gen Bank Accession No. AGZ58667.1, published Feb. 2, 2014 (Year: 2014).*
GenEmbl Accession No. AY693649, published Nov. 20, 2004 (Year: 2004).*
International Search report and written opinion dated Mar. 29, 2017 for PCT/US2016/059584, 15 pages.
Chen et al., "The family of terpene synthases in plants: a mid-size family of genes for specialized metabolism that is highly diversified throughout the kingdom", The Plant Journal, vol. 66, No. 1, Mar. 28, 2011, pp. 212-229; XP002738986.
Database UniProt [Online], Oct. 5, 2010, "RecName: Full=Beta-myrcene synthase, chloroplastic; EC=4.2.3.15; Flags: Precursor", XP002766180; 1 page.

* cited by examiner

1: Thujene    2: Sabinene    3: Myrcene    4: α - terpinene    5: Limonene

6: Ocimene    7: γ - terpinene    8: (E)-sabinene hydrate    9: (Z)-sabinene hydrate

10: β - Linalool    11: 4-terpineol

COMPOSITIONS AND METHODS FOR PRODUCTION OF MYRCENE

1. CROSS REFERENCE TO RELATED APPLICATION

This application is the U.S. national stage of International Application No. PCT/US2016/059584, filed Oct. 28, 2016, which claims benefit of priority of U.S. Provisional Application No. 62/248,240 filed Oct. 29, 2015, which is incorporated herein by reference.

2. FIELD OF THE INVENTION

The present invention relates to fermentation compositions, genetically modified microbial host cells, and isolated nucleic acid molecules for producing myrcene from the genetically modified microbial host cells.

3. BACKGROUND

Among terpenes, monoterpenes, the C10 members of the terpenoid family, are the main constituents of essential oils that are naturally found in leaves, flowers and fruits. These essential oils have various functions between plants and between plants and predators. For example, some of monoterpenes are involved in wound healing in plants. Examples of monoterpenes found in plants include limonene, myrcene, 3-carene, ocimene, pinene, and the like.

Monoterpenes are commercially important feedstocks for many industries. In particular, myrcene, is an important intermediate used in the perfumery industry. Myrcene can be derivatized to produce various end products including fragrances and flavors. While myrcene is found in nature, it exists in small quantities. Furthermore, while some monoterpenes, such as camphor, exist in a near pure form, myrcene generally exists as complex mixtures with other monoterpenes. Therefore, myrcene is difficult to isolate in large quantities from the complex mixtures.

Therefore, there is a need for an efficient and economical method for producing myrcene in high quantities.

4. SUMMARY

Provided herein are compositions and methods comprising genetically modified microbial host cells comprising a heterologous nucleic acid molecule encoding a myrcene synthase. It was discovered by the present inventors that a myrcene synthase derived from *Ocimum* species, when expressed in genetically modified microbial host cells, produces myrcene in relatively high quantities. Variants of the wild-type *Ocimum* species myrcene synthase are also generated using targeted mutagenesis techniques and screening of combinatorial libraries that contain various mutations. The myrcene synthase variants provided herein exhibit improved in vivo performance in terms of myrcene production and/or enzyme activity in genetically modified microbial host cells compared to their parent myrcene synthase. Therefore, fermentation compositions and methods provided herein can be used to produce myrcene in high quantity in an economic and reliable manner.

The monoterpene product profile produced by genetically modified microbial host cells comprising presently provided myrcene synthases is unique and distinguishable from those produced by other known myrcene synthases. Therefore, the fermentation compositions can be used to produce end products having unique properties, such as fragrance and flavor, which may be distinguishable from monoterpenes produced by other myrcene synthases.

In one aspect, provided herein is a fermentation composition comprising: (a) a genetically modified microbial host cell cultured in a culture medium, wherein the genetically modified microbial host cell comprises a heterologous nucleic acid molecule encoding a myrcene synthase; and (b) monoterpenes produced from the genetically modified microbial host cell, wherein the monoterpenes comprise myrcene as a major component and one or more co-products as minor components, wherein the one or more co-products comprise α-terpinene and/or γ-terpinene. In certain embodiments, one or more monoterpene co-products in the fermentation composition further comprise 4-terpineol. In certain embodiments, one or more monoterpene co-products in the fermentation composition further comprise sabinene, limonene, β-ocimene, and β-linalool. In certain embodiments, one or more monoterpene co-products in the fermentation composition further comprise α-thujene, (E)-sabinene hydrate, and/or (Z)-sabinene hydrate.

In certain embodiments, the monoterpenes in the fermentation composition comprise at least about 85% myrcene and less than about 15% one or more co-products, compared to a total amount of the monoterpenes, based on relative area % of the monoterpenes in a GC-MS chromatogram. In certain embodiments, the monoterpenes in the fermentation composition comprise between about 88% to about 93% myrcene, compared to the total amount of the monoterpenes, based on relative area % of the monoterpenes in the GC-MS chromatogram. In certain embodiments, the monoterpenes comprise, based on the total amount of the monoterpenes: about 89.09% to about 92.01% myrcene, about 0.80% to about 0.98% sabinene, about 0.67% to about 0.90% α-terpinene, about 0.54% to about 1.01% limonene, about 0.91% to about 1.21% β-ocimene, about 1.00% to about 1.06% γ-terpinene, about 0.76% to about 1.17% β-linalool, and about 2.32% to about 2.42% 4-terpineol, based on relative area % of the monoterpenes in the GC-MS chromatogram. In certain embodiments, the monoterpenes further comprise, based on the total amount of the monoterpenes: about 0% to about 0.51% α-thujene, about 0% to about 0.54% (E)-sabinene hydrate, and about 0.98% to about 1.13% (Z)-sabinene hydrate, based on relative area % of the monoterpenes in the GC-MS chromatogram. In certain embodiments, the fermentation composition comprises at least 50 mg, at least 100 mg, at least 500 mg, at least 1 gram, at least 5 grams, at least 10 grams, at least 50 grams, at least 100 grams, or at least 150 grams of myrcene per liter of the culture medium.

In another aspect, the fermentation composition comprises microbial host cells that are genetically modified to comprise a heterologous nucleic acid molecule encoding a myrcene synthase of an *Ocimum* species or a variant thereof. In some embodiments, the myrcene synthase comprises an amino acid sequence that has at least about 70%, at least about 75%, at least about 80%, at least about 85%, at least about 90%, at least about 95%, at least about 96%, at least about 97%, at least about 98%, at least about 99% sequence identity to the myrcene synthase of *Ocimum* species. In certain embodiments, the myrcene synthase comprises an amino acid sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 2. In certain embodiments, the myrcene synthase comprises an amino acid sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises at least one variant amino acid residue compared to SEQ ID NO: 2 at one or more of positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In certain embodiments, the myrcene synthase comprises an amino acid sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises at least one variant amino acid residue selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2. In certain embodiments, the myrcene synthase comprises an amino acid sequence of SEQ ID NO: 2, except that the amino acid sequence comprises one or more variant amino acid residues relative to SEQ ID NO:2, as described herein.

In certain embodiments, the genetically modified microbial host cells in the fermentation composition comprise a heterologous nucleic acid molecule encoding a myrcene synthase that comprises at least one set of variant amino acid residues compared to SEQ ID NO: 2, and wherein the at least one set of variant amino acid residues is selected from the group of sets of variant amino acid residues consisting of: (a) F381L, I404V, E528D, and M543I; (b) I404V and E528D; (c) F381L, D389G, I404V, Y439L, and E528D; (d) F381L, E528D, and M543I; (e) F381L, I404V, and E528D; (f) F381L, I404V, E528D, and A544S; and (g) F381L, I404V, E528D, and Q552R, wherein the positions are numbered with reference to SEQ ID NO: 2. In certain embodiments, the heterologous nucleic acid molecule encoding the myrcene synthase comprises a nucleotide sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 1, SEQ ID NO: 3, or SEQ ID NO: 4. In certain embodiments, the heterologous nucleic acid molecule encodes a myrcene synthase which comprises one or more amino acid variants described above.

In another aspect, the fermentation composition comprises genetically modified microbial host cells that further comprise a heterologous nucleic acid molecule encoding a geranyl pyrophosphate synthase. The geranyl pyrophosphate synthase catalyzes the formation of geranyl pyrophosphate, which is a substrate for a myrcene synthase. In certain embodiments, the geranyl pyrophosphate synthase is derived from a bacterium. In certain embodiments, the geranyl pyrophosphate synthase is derived from a *Streptomyces* species, in particular *Streptomyces aculeolatus*. In certain embodiments, the heterologous nucleic acid molecule encoding a geranyl pyrophosphate synthase comprises an amino acid sequence that has at least about 70%, at least about 75%, at least about 80%, at least about 85%, at least about 90%, at least about 95%, at least about 96%, at least about 97%, at least about 98%, at least about 99%, or 100% sequence identity to SEQ ID NO: 7. In certain embodiments, the heterologous nucleic acid molecule encoding the myrcene synthase and the heterologous nucleic acid molecule encoding the geranyl pyrophosphate synthase are chromosomally integrated into the genome of the genetically modified microbial host cells.

In certain embodiments, the genetically modified microbial host cells in the fermentation composition further comprise at least one heterologous mevalonate pathway gene encoding an enzyme selected from the group consisting of: (a) an enzyme that condenses two molecules of acetyl-coenzyme A to form acetoacetyl-CoA; (b) an enzyme that condenses acetoacetyl-CoA with another molecule of acetyl-CoA to form 3-hydroxy-3-methylglutaryl-CoA (HMG-CoA); (c) an enzyme that converts HMG-CoA into mevalonate; (d) an enzyme that converts mevalonate into mevalonate 5-phosphate; (e) an enzyme that converts mevalonate 5-phosphate into mevalonate 5-pyrophosphate; (f) an enzyme that converts mevalonate 5-pyrophosphate into IPP; and (g) an enzyme that converts IPP into DMAPP. In certain embodiments, the genetically modified microbial host cell comprises an endogenous farnesyl pyrophosphate which is functionally disrupted to direct carbon flow towards production of geranyl pyrophosphate.

In another aspect, genetically modified microbial host cells are provided. In certain embodiments, a genetically modified microbial host cell comprises: (a) a heterologous nucleic acid molecule encoding an *Ocimum* species myrcene synthase that comprises: (i) the amino acid sequence of SEQ ID NO: 2; or (ii) an amino acid sequence that has at least 70%, at least about 75%, at least about 80%, at least about 85%, at least about 90%, at least about 95%, at least about 96%, at least about 97%, at least about 98%, at least about 99% sequence identity to SEQ ID NO: 2; and (b) a heterologous nucleic acid molecule encoding a geranyl pyrophosphate synthase. In certain embodiments, the heterologous nucleic acid molecule encoding a geranyl pyrophosphate synthase is derived from a bacterium. In certain embodiments, the geranyl pyrophosphate synthase is derived from a *Streptomyces aculeolatus* geranyl pyrophosphate synthase. In certain embodiments, the heterologous nucleic acid molecule encodes a geranyl pyrophosphate synthase that comprises: (i) the amino acid sequence of SEQ ID NO: 7; or (ii) an amino acid sequence that has at least about 70%, at least about 75%, at least about 80%, at least about 85%, at least about 90%, at least about 95%, at least about 96%, at least about 97%, at least about 98%, at least about 99% sequence identity to SEQ ID NO: 7. In certain embodiments, the myrcene synthase in the microbial host cell comprises at least one variant amino acid residue compared to SEQ ID NO: 2 at one or more positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In certain embodiments, the myrcene synthase in the microbial host cell may comprise one or more variant amino acid residues described above.

In another aspect, isolated nucleic acid molecules encoding myrcene synthase variants are provided. In certain embodiments, the isolated nucleic acid molecule encodes a myrcene synthase comprising: (a) an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO:

2; and (b) at least one variant amino acid residue compared to SEQ ID NO: 2 at one or more positions 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In certain embodiments, at least one variant amino acid residue encoded by the isolated nucleic acid molecules is selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2.

In certain embodiments, the isolated nucleic acid molecule encodes a myrcene synthase comprising at least one set of variant amino acid residues compared to SEQ ID NO: 2, and wherein the at least one set of variant amino acid residues is selected from the group of sets of variant amino acid residues consisting of: (a) F381L, I404V, E528D, and M543I; (b) I404V and E528D; (c) F381L, D389G, I404V, Y439L, and E528D; (d) F381L, E528D, and M543I; (e) F381L, I404V, and E528D; (f) F381L, I404V, E528D, and A544S; and (g) F381L, I404V, E528D, and Q552R, wherein the positions are numbered with reference to SEQ ID NO: 2.

In certain embodiments, the isolated nucleic acid molecule comprises a nucleotide sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 1, SEQ ID NO: 3, or SEQ ID NO: 4. In certain embodiments, one or more codons in the isolated nucleic acid molecule encodes at least one variant amino acid residue selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2.

In another aspect, an isolated mutant myrcene synthase is provided. In certain embodiments, the isolated mutant myrcene synthase has at least about 70%, at least about 75%, at least about 80%, at least about 85%, at least about 90%, at least about 95%, at least about 96%, at least about 97%, at least about 98%, at least about 99% amino acid sequence identity to SEQ ID NO: 2 and exhibits an improved activity for converting geranyl diphosphate into myrcene compared to the activity of a myrcene synthase of SEQ ID NO: 2 under identical reaction conditions. In certain embodiments, the mutant myrcene synthase comprises a variant amino acid residue located at one or more of positions 27, 28, 207, 213, 222, 342, 347, 381, 382, 389, 390, 401, 404, 428, 439, 466, 482, 484, 505, 514, 517, 524, 527, 528, 543, 544, or 552, wherein the positions are numbered with reference to SEQ ID NO: 2. In certain embodiments, the mutant myrcene synthase comprises at least one variant amino acid residue selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2.

In another aspect, vectors comprising the isolated nucleic acid molecules described herein are provided.

In another aspect, a method of producing myrcene is provided. The method comprises culturing a genetically modified microbial host cell described herein in a culture medium under culture conditions suitable for production of myrcene. In certain embodiments, the method of producing myrcene comprises: (a) culturing a population of a genetically modified microbial host cell in a first culture medium under a non-inducing condition, wherein the genetically modified microbial host cell comprises a heterologous nucleic acid molecule encoding a myrcene synthase and a heterologous nucleic acid molecule encoding a geranyl pyrophosphate synthase; and (b) culturing the population or a subpopulation thereof in a second culture medium under an inducing condition which increases production of myrcene compared to the non-inducing condition of step (a), wherein the second culture medium comprises monoterpenes produced from the population or subpopulation of the genetically modified microbial host cell. In certain embodiments, the monoterpenes comprise myrcene as a major component and one or more co-products as minor components. In certain embodiments, one or more co-products comprise α-terpinene and γ-terpinene. In certain embodiments, the method of producing myrcene further comprises recovering myrcene from the culture medium. In certain embodiments, the genetically modified microbial host cells are cultured in a culture medium with an overlay. In certain embodiments, the genetically modified microbial host cells are cultured in a sealed container.

5. BRIEF DESCRIPTION OF THE FIGURES

FIG. 1 illustrates an overview of myrcene production in a microbial host cell. In the schematic diagram shown in FIG. 1, the microbial host cell converts feedstocks (e.g., sugar or other carbohydrates) to produce myrcene via the mevalonate pathway. To produce myrcene, geranyl pyrophosphate synthase (GPPS) and myrcene synthase (MyrS) can be incorporated into a microbial host cell to divert carbon flux from the C5-prenyl diphosphate metabolites isopentenyl diphosphate (IPP) and dimethylallyl diphosphate (DMAPP) to geranyl diphosphate (GPP). In some embodiments, FPP synthase (FPPS, e.g., encoded by ERG20 in S. cerevisiae) may be modulated, for example, functionally disrupted, to achieve maximum production of myrcene.

Figure 3A:
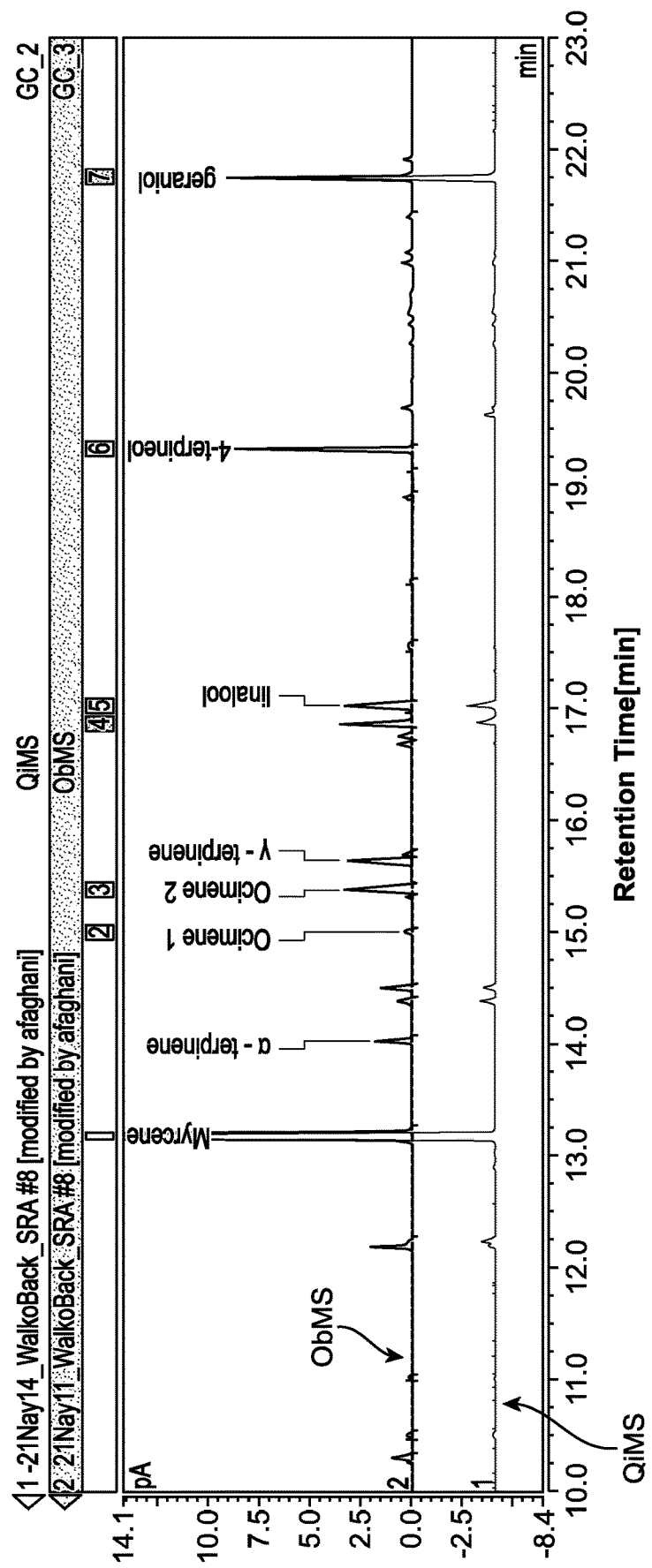

FIG. 3A illustrates chromatograms from GC-FID: Top trace, myrcene and co-products produced from genetically modified microbial host cells expressing Ocimum basilicum myrcene synthase (ObMS); bottom trace, myrcene and co-products produced from genetically modified microbial host cells expressing Quercus ilex (QiMS). The monoterpene production profiles of various myrcene synthases were tested using both GC-MS and GC-FID. GC-MS was used in particular to identify co-products including ocimene, phenethyl alcohol, linalool, and geraniol. Phenylethyl alcohol and geraniol were excluded from the myrcene area % purity calculation since phenylethyl alcohol is not a terpene and geraniol is likely not produced by the action of myrcene synthase but rather by yeast-derived pyrophosphatases. Only monoterpenes, which are identified by presence of molecular ion 136 (C10 terpene) on the GC-MS chromatograms as well molecular ion 154 (C10 terpene alcohol) are considered in the purity calculation. GC-FID detector was subsequently used to obtain more accurate area % monoterpene production profile data.

Figure 3B:
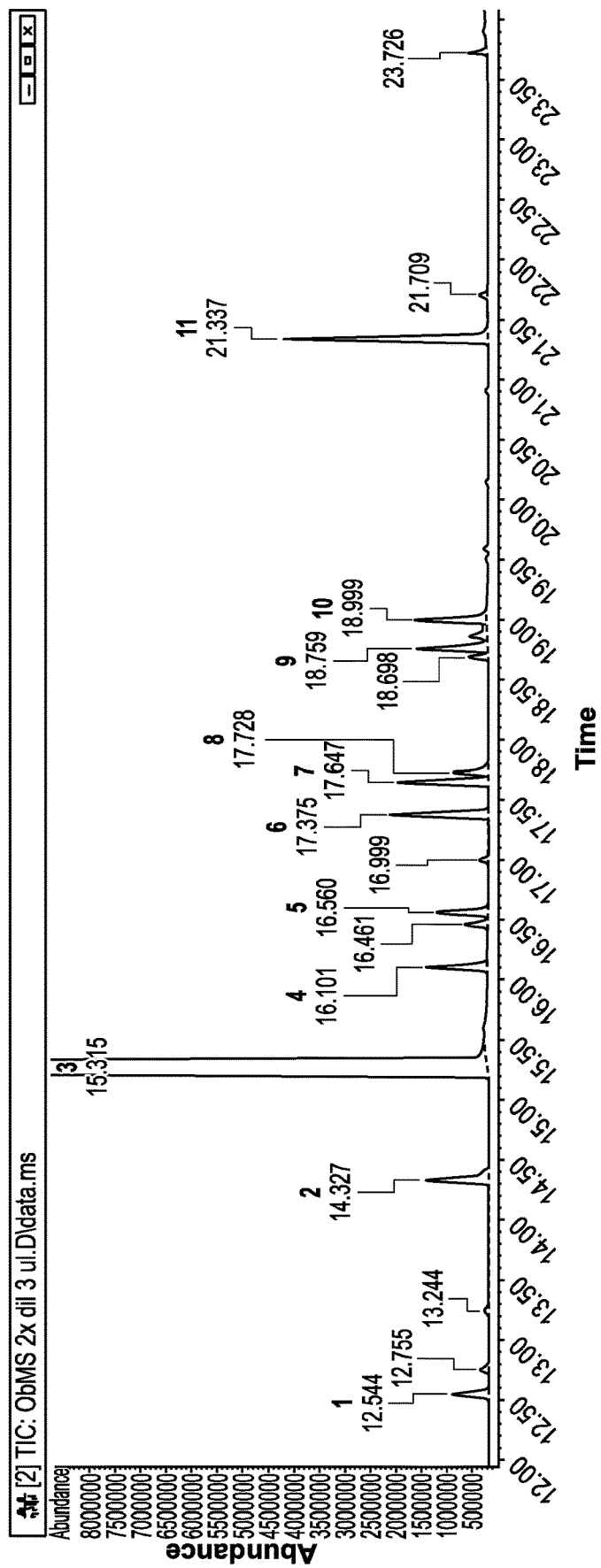

FIG. 3B illustrates GC-MS chromatogram zoomed in C10 terpenoid range of compounds produced by yeast host cells comprising *Ocimum basilicum* myrcene synthase. Assigned compound structures are listed in FIG. 4.

Figure 3C:
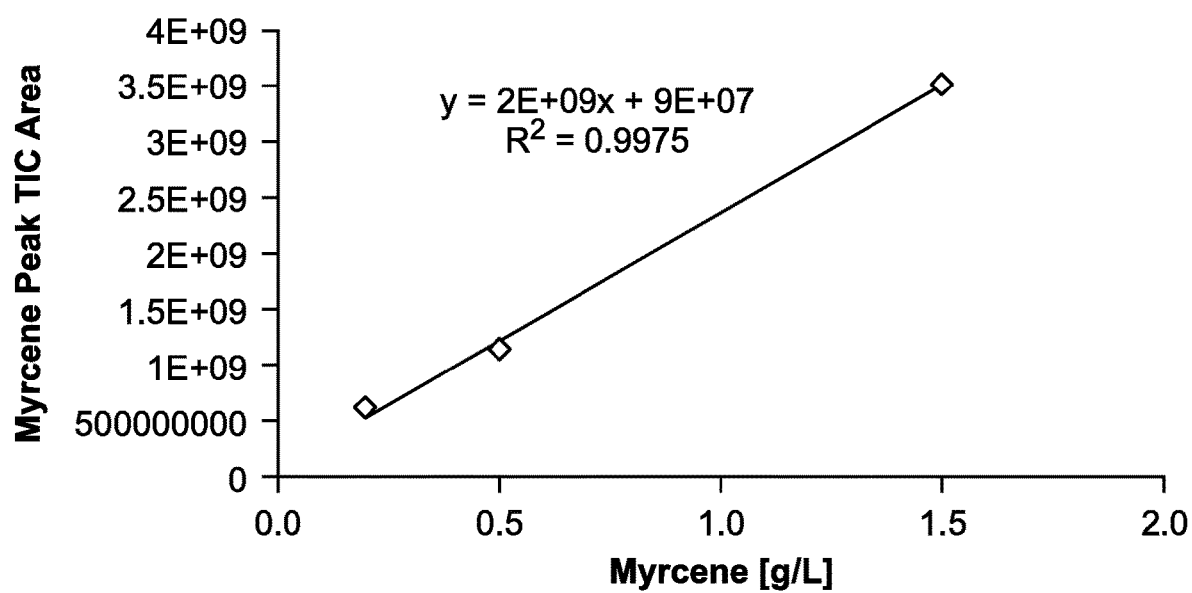

FIG. 3C illustrates linearity of myrcene signal response (area) as a function of sample concentration. For material purity assessment, the highest sample concentration, where biggest peak still remains within linear range of detector response, is used for data accuracy. Based on this data, 3 μl of sample at 0.5 g/L was chosen as appropriate for analysis in Example 7.7.

Figure 4:
Figure 4:
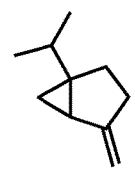
Figure 4:
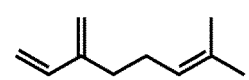
Figure 4:
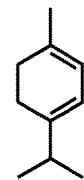
Figure 4:
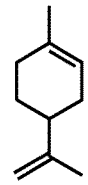
Figure 4:
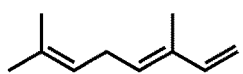
Figure 4:
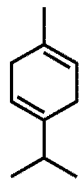
Figure 4:
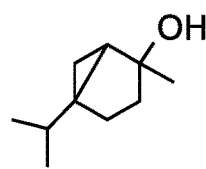
Figure 4:
Figure 4:
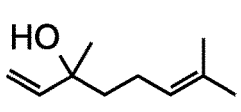
Figure 4:
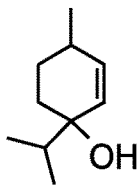

FIG. 4 illustrates chemical structures of compounds identified in monoterpenes produced by yeast host cells heterologously expressing *Ocimum basilicum* myrcene synthase.

Figure 5:
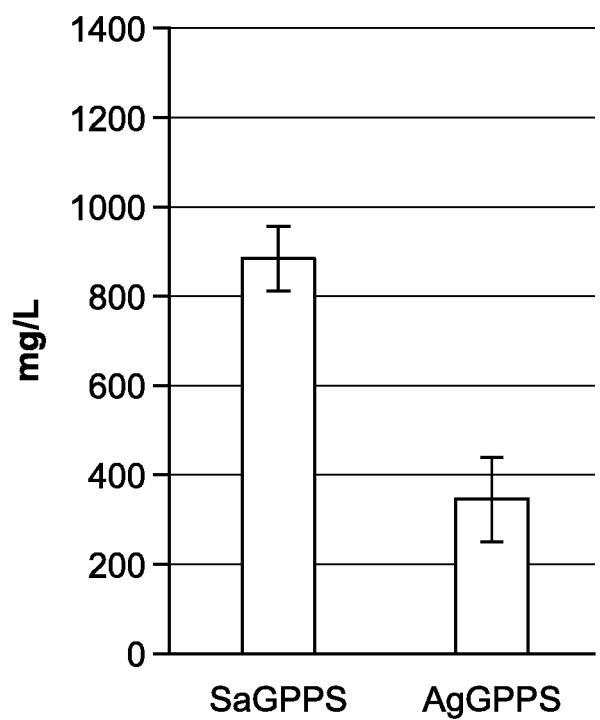

FIG. 5 provides a comparison of myrcene production in a strain comprising the *Streptomyces aculeolatus* geranyl pyrophosphate synthase (SaGPPS) gene and a strain comprising *Abies grandis* (AgGPPS) gene, both of which are codon optimized for expression in *S. cerevisiae*. Each GPPS was integrated as a single copy and ObMS was expressed on a high copy plasmid 4μ/Leu2d. Each flask was sampled at 72 hours, and the myrcene titers were determined by GC chromatograph. Error bars show standard deviation for 3 replicates.

Figure 6:
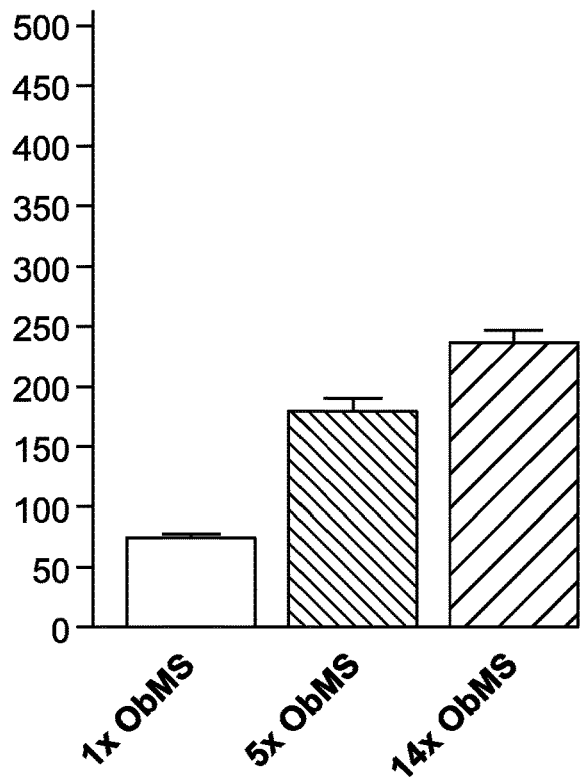

FIG. 6 illustrates comparison of the in vivo performance of the improved ObMS variants when integrated as a single copy in strain X100. The 1×ObMS is encoded by a wild-type myrcene synthase nucleic acid of *Ocimum basilicum* comprising SEQ ID NO: 1. The 1×ObMS was selected as the base enzyme (parent) to engineer. The 5×ObMS nucleic acid was created from codon optimization of the 1×ObMS nucleic acid for optimal expression in *Saccharomyces cerevisiae*. The 5×ObMS nucleic acid comprises a nucleotide sequence of SEQ ID NO: 3. The 14×ObMS nucleic acid was derived from directed evolution using 5×ObMS as parent. The 14×ObMS nucleic acid comprises a nucleotide sequence of SEQ ID NO: 4. The Y-axis is the myrcene production level at 72 hours as measured using limonene as an internal standard.

Figure 7:
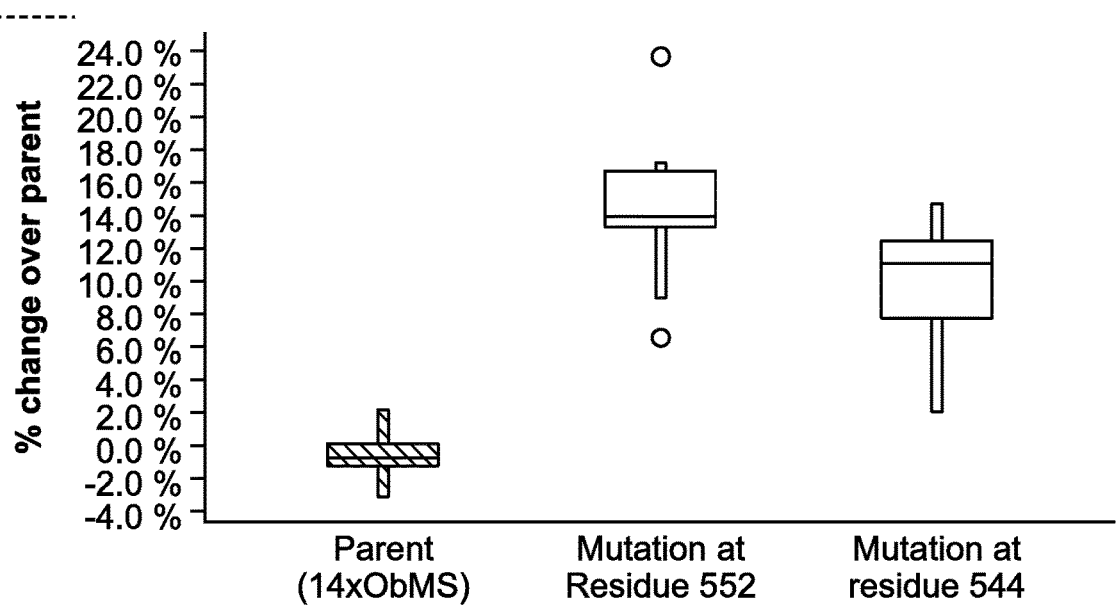

FIG. 7 illustrates two confirmed ObMS variants with improved myrcene production over their parent, 14×ObMS, based on the competition assay. The ObMS variant with mutation at residue 552 has an amino acid substitution from glutamine to arginine. The ObMS variant with a mutation at residue 544 has an amino acid substitution from alanine to serine. The Y-axis provides the percent improvement over the parent enzyme. Replicates of five (for parent) and twelve (for the two variants) were used in this experiment.

6. DETAILED DESCRIPTION OF THE EMBODIMENTS

Provided herein are compositions and methods for the efficient biosynthesis of myrcene, particularly via genetic engineering of myrcene synthases. In one embodiment, the production of myrcene is provided in high quantities in microorganisms that normally do not produce myrcene. In another embodiment, provided herein are compositions and methods for producing myrcene by culturing genetically modified microbial host cells that express a myrcene synthase derived from an *Ocimum* species. In certain embodiments, provided herein are isolated nucleic acid molecules that encode myrcene synthase variants derived from the wild-type *Ocimum basilicum* myrcene synthase, wherein the variants comprise one or more amino acid substitutions that improve in vivo performance of the enzyme in genetically modified microbial host cells. In certain embodiments, provided herein are isolated myrcene synthase variants that exhibit an improved activity for converting geranyl diphosphate into myrcene compared to wild-type myrcene synthases.

6.1 Definitions

Unless defined otherwise, all technical and scientific terms used herein have the same meaning as commonly understood by one of ordinary skill in the art to which this invention belongs. Reference is made here to a number of terms that shall be defined to have the following meanings:

The term "monoterpenes" are a class of terpenes that consist of two isoprene units. As used herein, the term "monoterpene" is also intended to include "monoterpenoid," which refers to a compound in which the C10 skeleton of the parent monoterpene has been modified, for example, by oxidation, or rearrangement of the carbon skeleton, and may be linear or cyclic.

The term "co-product" refers to a monoterpene that is co-produced with myrcene by genetically modified microbial host cells comprising a myrcene synthase through the catalytic reaction of the myrcene synthase. As used herein, myrcene and its co-products make up the total amount of monoterpenes produced from genetically modified microbial host cells.

As used herein, the term "the total amount of monoterpenes" produced from genetically modified microbial host cells exclude geraniol in the calculation of the total amount of monoterpenes or in the calculation of purity of myrcene produced by the microbial host cells. This is because geraniol is likely generated from myrcene synthase-independent hydrolysis of geranyl pyrophosphate in genetically modified microbial host cells.

As used herein, % refers to % measured as relative area % by GC-MS or GC-FID, unless specifically indicated otherwise. A relative area % refers to a ratio between an area of a peak of interest divided by a sum of all of the areas of peaks in the chromatogram multiplied by 100%. Thus, as used herein, % myrcene in a mixture of monoterpenes is based on peak area normalization of a gas chromatography-mass spectrometer (GC-MS) or gas chromatography-flame ionization detector (GC-FID) chromatogram. As described above, a peak associated with geraniol is excluded from the sum of all of the areas of peaks associated with monoterpenes. In certain embodiments, % of each monoterpene produced from genetically modified microbial host cells is measured under GC-MS conditions described in Example 7.7, and the relative area percent is calculated using 3 μl of sample at 0.5 g/L concentration of myrcene.

As used herein, the term "GC chromatogram" refers to an electronic and/or graphic record of data representing the absolute or relative quantitative detection of a plurality of separated chemical species obtained or derived from a group of molecules, where separation has been performed by a GC-MS or a GC-FID.

As used herein, the term "major component" in a mixture of compounds refers to a compound which comprises at least about 50%, at least about 55%, at least about 60%, at least about 65%, at least about 70%, at least about 75%, at least about 80%, at least about 85%, at least about 90%, or at least about 95%, compared to the total amount of compounds. With reference to monoterpenes produced from genetically modified microbial host cells, myrcene is a major component compared to the total amount of monoterpenes produced from the microbial host cells, based on relative area % of monoterpene peaks in a GC chromatogram as described in Example 7.7.

As used herein, the term "minor component(s)" in a mixture of compounds refer to one or more compounds which comprise, individually or collectively, less than about 50%, less than about 45%, less than about 40%, less than about 35%, less than about 30%, less than about 25%, less than about 20%, less than about 15%, less than about 10%, less than about 5%, less than about 4%, less than about 3%, less than about 2%, or less than about 1%, compared to the total amount of compounds. With reference to monoterpenes produced from genetically modified microbial host cells, co-products are minor components compared to the total amount of monoterpenes produced from the genetically modified microbial host cells, based on relative area % of monoterpene peaks in a GC chromatogram as described in Example 7.7.

As used herein, the term "substantially free" of a compound in a mixture of compounds refers to a compound having less than 0.1% of the compound based on the total amount of compounds based on relative area % of compound peaks in a GC chromatogram.

In the following description, all numbers disclosed herein are approximate values, regardless of whether the word "about" or "approximate" is used in connection therewith. Numbers may vary by 1%, 2%, 5%, or by 10 to 20%. Whenever a numerical range with a lower limit $R^L$ and an upper limit $R^U$ is disclosed, any number falling within the range is specifically disclosed. In particular, the following numbers $R_k$ within the range are specifically disclosed: $R_k=R^L+k*(R^U-R^L)$, wherein k is a variable ranging from 0.01 to 1 with a 0.01 increment, i.e., k is 0.01, 0.02, 0.03, 0.04, 0.05, ..., 0.5, 0.51, 0.52, ..., 0.95, 0.96, 0.97, 0.98, 0.99, or 1. Further, any numerical range defined by any two numbers $R_k$ as defined above is also specifically disclosed herein.

The term "myrcene" or "β-myrcene," also known as 7-methyl-3-methylene-1,6-octadiene, is a monoterpene having the molecular formula $C_{10}H_{16}$ and has the following molecular structure:

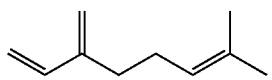

The term "sabinene," also known as 4-methylene-1-(1-methylethyl)bicyclo[3.1.0]hexaner, is a monoterpene having the molecular formula $C_{10}H_{16}$ and has the following structure or a stereoisomer thereof:

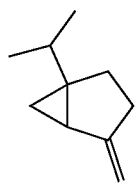

The term "α-terpinene," also known as 1-Isopropyl-4-methyl-1,3-cyclohexadiene, is a monoterpene having the molecular formula of $C_{10}H_{16}$ and has the following structure:

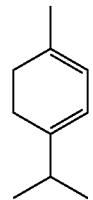

The term "limonene," also known as 1-methyl-4-(1-methylethenyl)-cyclohexene, is a monoterpene having the molecular formula of $C_{10}H_{16}$ and has the following structure or a stereoisomer thereof:

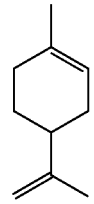

The term "β-ocimene," also known as cis-3,7-dimethyl-1,3,7-octatriene, is a monoterpene having the molecular formula of $C_{10}H_{16}$ and has the following structure or a stereoisomer thereof:

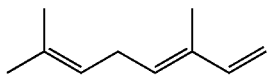

The term "γ-terpinene," also known as 4-methyl-1-(1-methylethyl)-1,4-cyclohexadiene, is a monoterpene having the molecular formula of $C_{10}H_{16}$ and has the following structure:

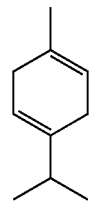

The term "β-linalool," also known as 3,7-dimethylocta-1,6-dien-3-ol, is a monoterpene product having the molecular formula of $C_{10}H_{18}O$ and has the following structure or a stereoisomer thereof:

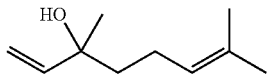

The term "α-thujene," also known as 1-isopropyl-4-methylbicyclo[3.1.0]hex-3-ene, is a monoterpene having the molecular formula of $C_{10}H_{16}$ and has the following structure or a stereoisomer thereof:

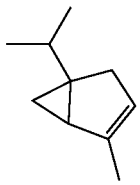

The term "(E)-sabinene hydrate," also known as (1S,4R,5R)-4-methyl-1-propan-2-ylbicyclo[3.1.0]hexan-4-ol, is a monoterpene having the molecular formula of $C_{10}H_{18}O$ and has the following structure or a stereoisomer thereof:

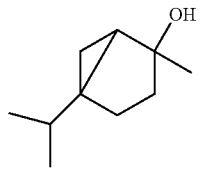

The term "(z)-sabinene hydrate," also known as 4-methyl-1-propan-2-ylbicyclo[3.1.0]hexan-4-ol, is a monoterpene having the molecular formula of C10H18O and has the following structure or a stereoisomer thereof:

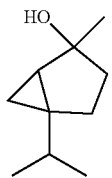

As used herein, to "functionally disrupt" or a "functional disruption" e.g., of a target gene, for example, a gene encoding FPP synthase, means that the target gene is altered in such a way as to decrease in the host cell the activity of the protein encoded by the target gene. Similarly, to "functionally disrupt" or a "functional disruption" e.g., of a target protein, for example, FPP synthase, means that the target protein is altered in such a way as to decrease in the host cell the activity of the protein. In some embodiments, the activity of the target protein encoded by the target gene is eliminated in the host cell. In other embodiments, the activity of the target protein encoded by the target gene is decreased in the host cell. Functional disruption of the target gene may be achieved by deleting or mutating all or a part of the gene so that gene expression is eliminated or reduced, or so that the activity of the gene product is eliminated or reduced. Functional disruption of the target gene may also be achieved by deleting or mutating a regulatory element of the gene, e.g., the promoter of the gene so that expression is eliminated or reduced, or by deleting or mutating the coding sequence of the gene so that the activity of the gene product is eliminated or reduced. In some embodiments, functional disruption of the target gene results in the removal of the complete open reading frame of the target gene.

The term "fermentation" is used to refer to culturing microorganisms that utilize carbon sources, such as sugar, as an energy source to produce a desired product.

The term "culture medium" refers to a medium which allows growth of biomass and production of microbial metabolites. It contains a source of carbon and may further contain a source of nitrogen, a source of phosphorus, a source of vitamins, a source of minerals, and the like.

As used herein, the term "fermentation medium" may be used synonymously with "culture medium." Generally, the term "fermentation medium" may be used to refer to a medium which is suitable for culturing microorganisms for a prolonged time period to produce a desired compound from microorganisms.

The term "medium" refers to a culture medium and/or fermentation medium. The "medium" can be liquid or semi-solid. A given medium may be both a culture medium and a fermentation medium.

The term "whole cell broth" refers to the entire contents of a vessel (e.g., a flask, plate, fermentor and the like), including cells, aqueous phase, compounds produced in hydrocarbon phase and/or emulsion. Thus, the whole cell broth includes the mixture of a culture medium comprising water, carbon source (e.g., sugar), minerals, vitamins, other dissolved or suspended materials, microorganisms, metabolites and compounds produced by microorganisms, and all other constituents of the material held in the vessel in which monoterpenes including myrcene is being made by the microorganisms.

The term "fermentation composition" is used interchangeably with "whole cell broth." The fermentation composition can also include an overlay if it is added to the vessel during fermentation.

The term "biosynthetic pathway" refers to a pathway with a series of enzymes leading to the biosynthesis of a molecule.

Figure 2A:
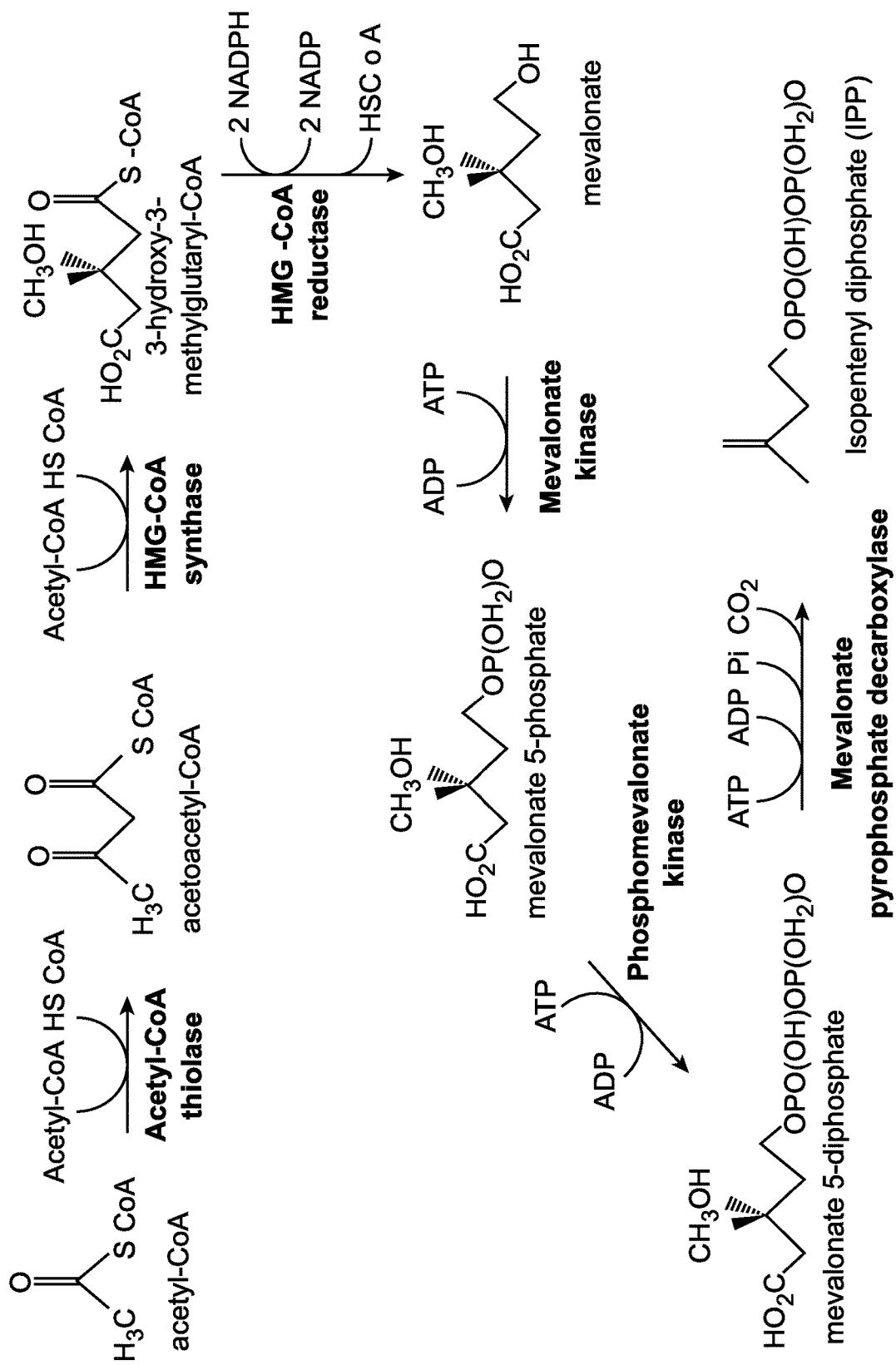
FIG. 2A is a schematic depiction of the mevalonate pathway.

The term "mevalonate pathway" or "MEV pathway" is used herein to refer to a biosynthetic pathway that can convert acetyl-CoA to IPP. One embodiment of the MEV pathway is shown in FIG. 2A. The mevalonate pathway comprises enzymes that catalyze the following steps: (a) condensing two molecules of acetyl-CoA to form acetoacetyl-CoA; (b) condensing acetoacetyl-CoA with acetyl-CoA to form 3-hydroxy-3-methylglutaryl-CoA (HMG-CoA); (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate (IPP). The "top half" of the mevalonate pathway refers to the enzymes responsible for the conversion of acetyl-CoA to mevalonate through a MEV pathway intermediate. In certain embodiments, the IPP isomerase, which converts IPP into DMAPP, is also referred to as a MEV pathway enzyme.

The term "deoxyxylulose 5-phosphate pathway" or "DXP pathway" is used herein to refer to the biosynthetic pathway that converts glyceraldehyde-3-phosphate and pyruvate to IPP and DMAPP through a series of enzymes, which are referred to as DXP pathway enzymes. One embodiment of the DXP pathway is illustrated schematically in FIG. 2B.

The term "pyrophosphate" is used interchangeably herein with "diphosphate."

The term "myrcene synthase" refers to an enzyme capable of catalyzing the formation of myrcene as a major product from a geranyl pyrophosphate precursor (also referred to as geranyl diphosphate precursor). The catalytic reaction of myrcene synthase may concurrently produce other co-products as minor components in addition to myrcene. For example, a myrcene synthase is capable of producing at least about 50%, at least about 60%, at least about 70%, at least about 80%, at least about 85%, at least about 90%, at least about 95%, at least about 96%, at least about 97%, at least about 98%, or at least about 99% myrcene, compared to the total amount of monoterpenes produced by microbial host cells genetically modified with the myrcene synthase, based on relative area % of monoterpenes in a GC chromatogram. As used herein, the term "myrcene synthase" may include a bifunctional enzyme which catalyzes two different catalytic reactions using two different substrates.

The term "geranyl pyrophosphate synthase" refers to a polypeptide capable of catalyzing the formation of geranyl pyrophosphate by condensing precursors, isopentenyl pyrophosphate (IPP) and dimethylallyl pyrophosphate (DMAPP) together. As used herein, the term "geranyl pyrophosphate synthase" may include a bifunctional enzyme which catalyzes two different catalytic reactions using two different substrates.

As used herein, the term "sequence identity" or "percent identity," in the context or two or more nucleic acid or protein sequences, refer to two or more sequences or subsequences that are the same or have a specified percentage of amino acid residues or nucleotides that are the same. For example, the sequence can have a percent identity of at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22: 4673-4680), ALIGN (Myers et al., (1988) *CABIOS,* 4: 11-17), FASTA (Pearson et al., (1988) PNAS, 85:2444-2448; Pearson (1990), *Methods Enzymol.,* 183: 63-98) and gapped BLAST (Altschul et al., (1997) *Nucleic Acids Res.,* 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=1, Nucleic mismatch=−3, Expectation value=10.0, Word size=11). For polypeptide sequence alignment and sequence identity calculations, BLASTP program is used with its default parameters (Gap opening=11, Gap extension penalty=2; Nucleic match=1; Nucleic mismatch=−3, Expectation value=10.0; Word size=11; matrix Blosum 62). Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. For example, a "homolog" of a reference protein or nucleic acid includes a protein or nucleic acid which has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% sequence identity to the reference protein or nucleic acid, respectively. As discussed above, various programs for sequence alignment and analysis are well known, and can be used to determine whether two sequences are homologs of each other.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., *Current Protocols in Molecular Biology*, ed. Ausubel et al.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol. Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V); and 6) Phenylalanine (F), Tyrosine (Y), Tryptophan (W).

As used herein, the term "variant amino acid residue" refers to an amino acid change or an amino acid substitution in a variant form of a reference protein. For example, a variant amino acid residue "F381L" refers that position 381 of a reference protein, which normally has phenylalanine (F), is substituted with amino acid residue leucine (L) in the variant protein. In another example, a variant amino acid residue "D389G" refers that position 389 of a reference protein, which normally has amino acid residue aspartic acid (D), is substituted with amino acid residue glycine (G) in the variant protein.

As used herein, the term "myrcene synthase variant" or "mutant myrcene synthase" with reference to an amino acid sequence refers to a myrcene synthase that has a different amino acid sequence compared to a reference myrcene synthase (e.g., a wild-type myrcene synthase). The myrcene synthase variant or mutant myrcene synthase may comprise amino acid additions, deletions, substitutions and/or insertions, compared to its reference myrcene synthase. The term "myrcene synthase variant" or "mutant myrcene synthases" nucleic acid molecule with reference to a nucleotide sequence refers to a myrcene synthase nucleic acid molecule that has a different nucleotide sequence compared to a reference myrcene synthase nucleic acid molecule. For example, compared to the wild-type myrcene synthase nucleic acid molecule, a myrcene synthase variant nucleic acid molecule or a mutant myrcene synthase nucleic acid molecule may comprise nucleotide addition(s), deletion(s), and/or substitution(s) that may or may not result in changes to the corresponding amino acid sequence. In some embodiments where nucleotide changes do not result in changes to the amino acid sequence, the changes may nonetheless effect improved activity of the myrcene synthase, for example, through codon optimization.

As used herein, the term "reference" or "parent" sequence (e.g., nucleic acid or protein) refers to a sequence selected for sequence comparison, enzyme activity comparison, or myrcene production comparison with a variant sequence (e.g., nucleic acid or protein).

As used herein, the term "native" or "endogenous" refers to a substance or process that can occur naturally in a host cell.

As used herein, the term "genetically modified" denotes a host cell that comprises a heterologous nucleotide sequence.

As used herein, the term "heterologous" refers to what is not normally found in nature. For example, the term "heterologous" when used with respect to a nucleic acid (DNA or RNA) or protein refers to a nucleic acid or protein that does not occur naturally as part of the organism, cell, genome, or DNA or RNA sequence in which it is present, or that is found in a cell or location or locations in the genome or DNA or RNA sequence that differ from that in which it is found in nature. The term "heterologous compound" refers to the production of a compound by a cell that does not normally produce the compound, or to the production of a compound at a level at which it is not normally produced by the cell.

As used herein, the term "naturally occurring" refers to what is found in nature. For example, a myrcene synthase that is present in an organism that can be isolated from a source in nature and that has not been intentionally modified by a human in the laboratory is naturally occurring myrcene synthase. Conversely, as used herein, the term "naturally not occurring" refers to what is not found in nature but is created by human intervention.

As used herein, the term "in vivo performance" or "activity" of a myrcene synthase refers to its ability to convert a geranyl pyrophosphate to myrcene when expressed in a microbial host cell. Accordingly, the term "improved in vivo performance" or "improved activity" refers to an increased ability of a myrcene synthase to convert a geranyl pyrophosphate to myrcene when expressed in a microbial host cell.

As used herein, the phrase "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

The terms "amino acid sequence," "peptide," "oligopeptide," "polypeptide" and "protein" are used here interchangeably, and refer to a polymeric form of amino acids of any length which may or may not be chemically or biochemically modified.

The terms "polynucleotide" and "nucleic acid" are used here interchangeably, referring to polymeric forms of any length, both ribonucleotides and deoxyribonucleotide.

The term "isolated nucleic acid" or "isolated nucleic acid molecule," when applied to DNA, refers to a DNA molecule that is separated from sequences with which it is immediately contiguous in the naturally occurring genome of the organism in which it originated. An "isolated nucleic acid" or "isolated nucleic acid molecule" also includes non-genomic nucleic acids such as cDNA or other non-naturally occurring nucleic acid molecules.

The term "cDNA" is defined herein as a DNA molecule which can be prepared by reverse transcription from a mature, spliced, mRNA molecule obtained from a cell. cDNA lacks intron sequences that are usually present in the corresponding genomic DNA.

As used herein, the phrase "operably linked" refers to a functional linkage between nucleic acid sequences such that the linked promoter and/or regulatory region functionally control expression of the coding sequence.

As used herein, the term "productivity" refers to production of a compound by a host cell, expressed as the amount of a compound produced (by weight) per amount of fermentation medium in which the host cell is cultured (by volume) over time (per hour). As applied to myrcene, the term "productivity" refers to production of myrcene by a host cell, expressed as the amount of myrcene produced (by weight) per amount of fermentation medium in which the host cell is cultured (by volume) over time (per hour).

As used herein, the term "yield" refers to production of a compound by a host cell, expressed as the amount of the compound produced per amount of carbon source consumed by the host cell, by weight. More specifically, as applied to production of myrcene, the term "yield" refers to the amount of myrcene generated compared with total reducing sugar added to a fermentor vessel or a flask (i.e., grams of myrcene produced divided by grams of total reducing sugar added, expressed as percentage). The total reducing sugar is a unit of measurement of sugar in grams. A reducing sugar is any sugar that is capable of acting as a reducing agent because it has a free aldehyde group or a free ketone group. All monosaccharides, such as galactose, glucose, and fructose, are reducing sugars. For example, if 10 grams of myrcene is produced by feeding host cells 100 grams of glucose (i.e., 100 grams of reducing sugar), then the yield of myrcene is 10%.

The term "titer" or "concentration" refers to production of a compound by a host cell, expressed as the amount of a compound produced (by weight) per volume of fermentation medium in which the host cell is cultured.

The term "a," "an," and "the" means "at least one" unless the context clearly indicates otherwise.

6.2 Biosynthetic Pathways for Production of Myrcene

Figure 1:
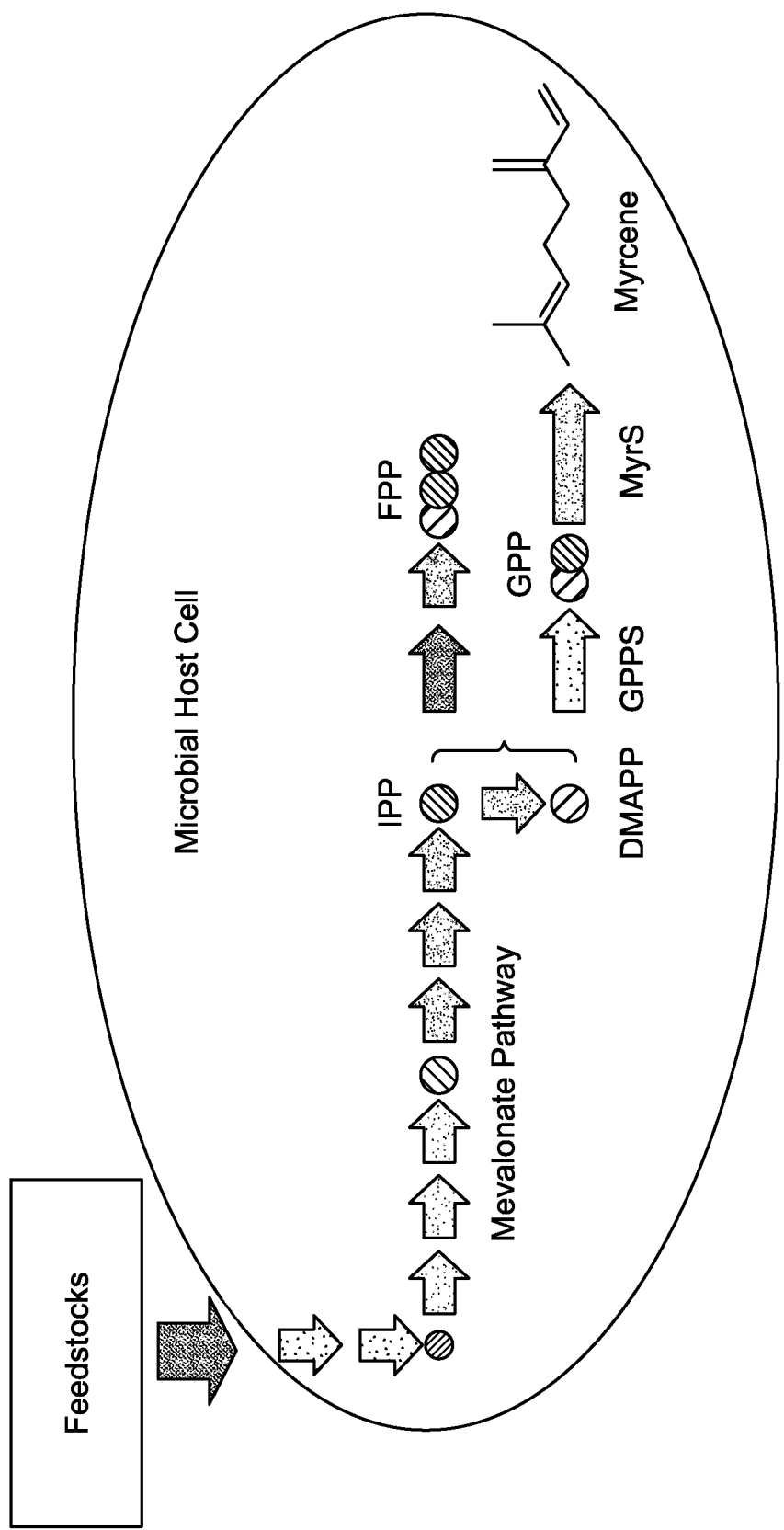

Myrcene is an aromatic hydrocarbon which is an important part of the essential oils of a number of different plants. It is a monoterpene, which is derived from the C5 compound isopentyl pyrophosphate (IPP). As shown in FIG. 1, the biosynthetic steps leading from IPP to monoterpenes include two enzymes, geranyl pyrophosphate synthase (GPPS) and myrcene synthase (MyrS). In order to produce myrcene, both GPPS and MyrS are typically required in genetically modified microbial host cells, although certain terpene synthases are known to be bifunctional as GPPS and MyrS. Generally, GPPS diverts the carbon flux from the C5-prenyl diphosphate metabolites isopentenyl diphosphate (IPP) and dimethylallyl diphosphate (DMAPP) to geranyl diphosphate (GPP). MyrS, in turn, can convert the GPP precursor to myrcene. While FIG. 1 illustrates myrcene as the only monoterpene produced by the catalytic reaction of a myrcene synthase with a geranyl pyrophosphate, a number of other monoterpenes may be concurrently produced as minor components by certain myrcene synthases.

Figure 2B:
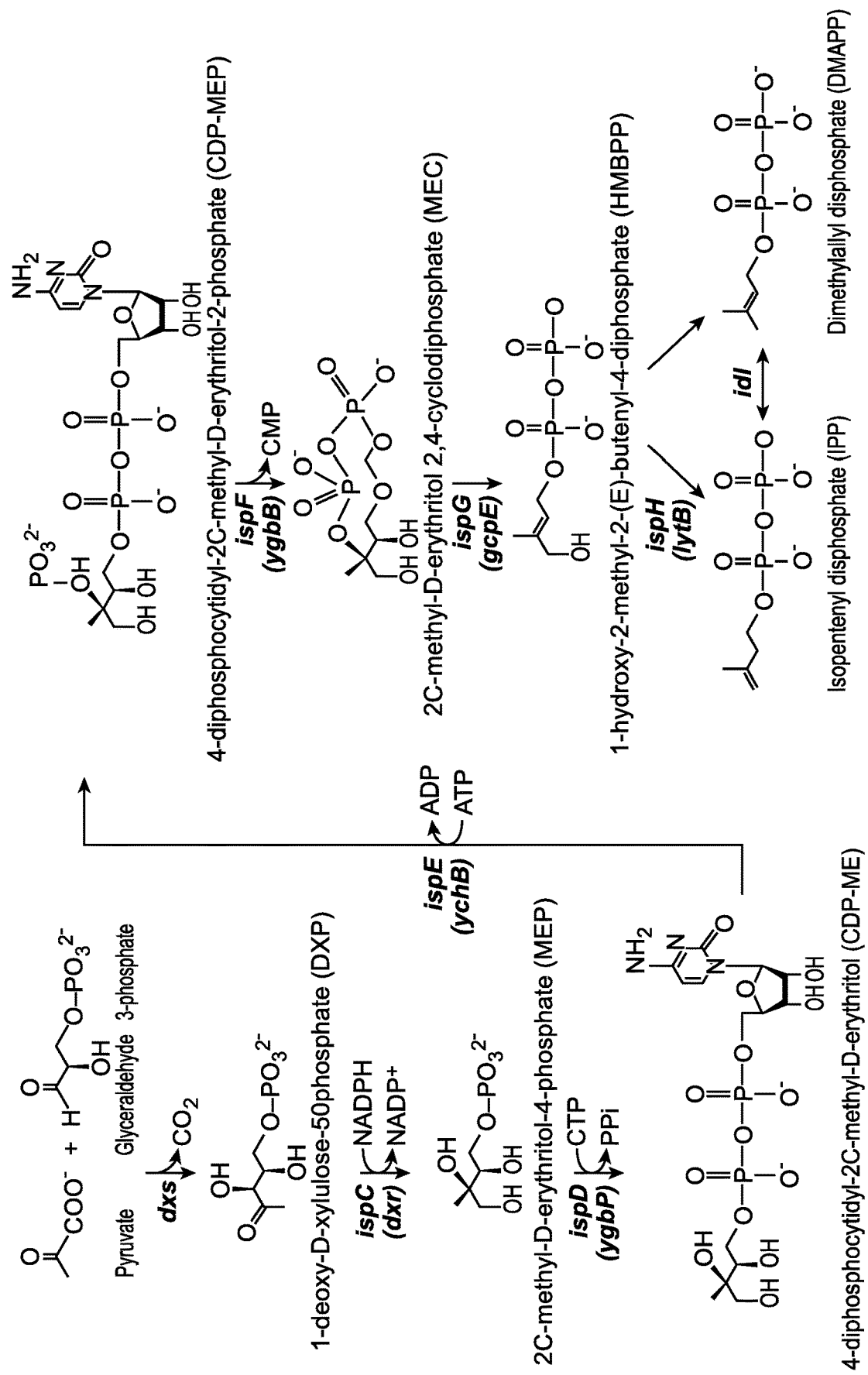
FIG. 2B is a schematic depiction of the 1-deoxy-D-xylulose 5-diphosphate (DXP) pathway.

Furthermore, while FIG. 1 illustrates using the mevalonate pathway for production of myrcene, the present compositions and methods are not limited to using the mevalonate pathway for the production of myrcene. Two different pathways leading to IPP and DMAPP exist: the mevalonate pathway (MEV pathway) and non-mevalonate pathway (DXP pathway). Eukaryotes, with the exception of plants, generally use the mevalonate dependent pathway. As shown in FIG. 2A, the MEV pathway uses acetyl CoA as the initial precursor to produce IPP and its isomer DMAPP through a series of MEV pathway enzymes. Prokaryotes, with some exceptions, typically employ only the DXP pathway to produce IPP and DMAPP. Plants use both the MEV pathway and DXP pathway. As shown in FIG. 2B, the DXP pathway uses glyceraldehyde-3-phosphate and pyruvate as the initial precursors to produce IPP and its isomer DMAPP through a series of DXP pathway enzymes. In certain embodiments, either the MEV pathway or DXP pathway enzymes may be utilized to produce precursors for biosynthesis of myrcene in genetically modified microbial host cells.

In compositions and methods provided herein, a microbial host cell is genetically modified to comprise a heterologous myrcene synthase sequence. In certain embodiments, the microbial host cell is further genetically modified to comprise a heterologous geranyl pyrophosphate synthase sequence. In some embodiments, additional heterologous nucleic acid molecules (e.g., MEV or DXP pathway genes) may be introduced together with the heterologous myrcene synthase and the heterologous geranyl pyrophosphate synthase to enhance the production of myrcene in genetically modified microbial host cells. In certain embodiments, one or more endogenous genes of the host genome may be functionally disrupted or modified to improve myrcene production in genetically modified microbial host cells.

6.3 Myrcene Synthases and its Variants

A number of myrcene synthase genes have been previously isolated and annotated as myrcene synthases in the literature. While some of them have been characterized biochemically, none of them have been shown to biosynthetically produce myrcene in high quantity in genetically modified microbial host cells. It has been discovered by the present inventors that compared to myrcene synthase sequences obtained from other organisms, the myrcene synthases derived from *Ocimum* species, in particular *Ocimum basilicum*, are capable of providing relatively high production of myrcene in genetically modified microbial host cells.

Furthermore, as shown in the examples section, both wild-type *Ocimum basilicum* and its variants, when expressed in genetically modified microbial host cells, exhibit a unique monoterpene product profile, which is distinguishable from monoterpene product profiles produced by myrcene synthases derived from other organisms. For example, the presently provided myrcene synthases, when expressed in genetically modified microbial host cells, produce α-terpinene and γ-terpinene as co-products together with myrcene. However, other myrcene synthases, such those derived from *Quercus ilex* do not produce α-terpinene and γ-terpinene as co-products with myrcene. See, e.g., FIG. 3A. Therefore, the product profile of the presently provided myrcene synthase sequences have a unique molecular fingerprint and is distinguishable from the product profile of other myrcene synthase sequences. As a result, they can be utilized to produce end products, such as fragrances and flavors, with potentially distinct characteristics (e.g., odor or flavor profile) which may differ from those produced by other myrcene synthases.

Thus, provided herein are myrcene synthase sequences, which, when expressed in genetically modified microbial host cells, produce myrcene in relatively high quantity with a distinct monoterpene product profile. In certain embodiments, the wild-type myrcene synthase sequences from *Ocimum* species are codon optimized for a selected microbial host cell to produce myrcene. In certain embodiments, the myrcene synthase variants are provided where one or more amino acid positions of the wild-type myrcene synthases are altered to further improve in vivo performance of the enzymes to enhance myrcene production, purity, and/or product profile.

6.3.1. Myrcene Synthase Variant Amino Acid Sequences

Provided herein are myrcene synthase variants which include modification(s) of amino acid residues compared to a reference sequence and yet still retain the biological activity as a myrcene synthase. In one embodiment, the reference myrcene synthase is a wild-type myrcene synthase of *Ocimum basilicum* (ObMS) comprising amino acid sequence SEQ ID NO: 2. In another embodiment, the reference myrcene synthase may be a homolog of the myrcene synthase of *Ocimum basilicum*. For example, the reference myrcene synthase may be myrcene synthases from *Ocimum* species other than *Ocimum basilicum* which share a substantial sequence identity with SEQ ID NO: 2. In some embodiments, myrcene synthase variants may also be generated from other homologs or orthologs of the *Ocimum basilicum* myrcene synthase from different organisms.

As used herein, the term "wild-type" myrcene synthase refers to a truncated form of naturally occurring myrcene synthases without the N-terminal transit peptide. Terpene synthases derived from plants including the myrcene synthase preprotein of *Ocimum basilicum* include an N-terminal transit peptide sequence (also referred to as plastid-targeting sequence) which is necessary in plants to import the nuclear-encoded plastid protein into plastids. In microbial host cells, the N-terminal transit peptide sequence is not necessary for expression. As such, to express *Ocimum basilicum* or other myrcene synthases in microbial host cells, the N-terminal transit peptide in the myrcene synthase preprotein is truncated to remove the N-terminal transit peptide sequence. An exemplary embodiment of *Ocimum basilicum* myrcene synthase nucleotide sequence without the transit peptide sequence is shown as SEQ ID NO: 1 (also referred to as 1×ObMS nucleic acid), and the corresponding amino acid sequence is shown as SEQ ID NO: 2.

Myrcene synthase variants according to certain embodiments may include amino acid substitutions, deletions, additions, and/or insertions at certain amino acid positions compared to a reference myrcene synthase. The deletions or additions may occur at the N-terminus or C-terminus of the reference protein. In one embodiment, an amino acid sequence may be added to one or both terminal ends of the reference protein. For example, an amino acid sequence may be added to the reference myrcene synthase to increase the myrcene synthase stability in myrcene synthase variants. In another embodiment, myrcene synthase variants may include a deletion of a non-functional portion of the enzyme. For example, a myrcene synthase variant may include a deletion of one, two, three, or four amino acid residues at the N-terminus compared to a reference sequence of SEQ ID NO: 2. The amino acid sequence of SEQ ID NO: 2, which is a truncated wild-type *Ocimum basilicum* myrcene synthase, includes RR(x)8W motif sequences near the N-terminus. In the motif sequence, R is arginine, W is tryptophan, and "(x)8" represent 8 amino acid residues between R and W. The RR(x)8W motif is generally found in the N-terminal part of class III terpene synthase proteins. The amino acid sequence of SEQ ID NO: 2 includes four amino acid residues, MVEP, to the N-terminus of the RR(x)8W motif. One or more of these MVEP amino acid residues may not necessarily affect the myrcene synthase function or its expression in genetically modified microbial host cells. Thus, in certain embodiments, a myrcene synthase variant may further include a deletion of one or more amino acid residues of MVEP at the N-terminus of SEQ ID NO: 2.

In other embodiments, a myrcene synthase variant may include one or more amino acid substitutions compared to a reference sequence. For example, a myrcene synthase variant may include one, two, three, four, five, six, seven, eight, nine, ten, or more amino acid substitutions compared to the reference myrcene synthase sequence, and retains the myrcene synthase activity of the reference sequence. In certain embodiments, a myrcene synthase variant comprises one or more amino acid substitutions up to 5%, up to 10%, up to 15%, up to 20%, up to 25%, or up to 30% of the reference myrcene synthase sequence. In certain embodiments, amino acid substitutions may include conservative amino acid substitutions. For example, a basic amino acid residue (e.g., lysine) in the reference myrcene synthase may be exchanged with another basic amino acid residue (e.g., arginine). In another example, a polar amino acid residue (e.g., serine) in the reference myrcene synthase may be substituted with another polar amino acid residue (e.g., threonine). In other embodiments, amino acid substitutions may include non-conservative amino acid substitutions. For example, a nonpolar amino acid residue (e.g., glycine) in the reference myrcene synthase may be substituted with an acidic amino acid residue (e.g., glutamine). In another example, an aromatic amino acid residue (e.g., tyrosine) may be substituted with a cyclic amino acid residue (e.g., proline).

In certain embodiments, a myrcene synthase variant comprises an amino acid sequence that has at least about 70%, at least about 75%, at least about 80%, at least about 85%, at least about 90%, at least about 95%, at least about 96%, at least about 97%, at least about 98%, or at least about 99% sequence identity to a reference myrcene synthase. In an embodiment, the reference myrcene synthase comprises an amino acid sequence of SEQ ID NO: 2, the wild-type sequence of *Ocimum basilicum* myrcene synthase. Thus, in certain embodiments, a myrcene synthase variant comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2.

In certain embodiments, myrcene synthase variants are not naturally occurring myrcene synthases, and comprise one or more amino acid substitutions compared to wild-type myrcene synthases. In certain embodiments, a myrcene synthase variant may comprise at least one variant amino acid residue compared to SEQ ID NO: 2 at one or more of positions 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. As shown in the examples section, one or more amino acid substitutions at these positions of SEQ ID NO: 2 generated beneficial mutations in terms of improving in vivo myrcene synthase activity or performance. For example, as described in Example 7.9, myrcene synthase variants comprising one or more mutations at these positions of SEQ ID NO: 2 exhibited an improved myrcene to limonene production ratio in a competition assay. In another example, as described in Example 7.11, myrcene synthase variants comprising one or more mutations at these positions of SEQ ID NO: 2 exhibited improved myrcene production (e.g., titer) compared to a parent myrcene synthase comprising an amino acid sequence of SEQ ID NO: 2.

In certain embodiments, the myrcene synthase variants described herein comprise one or more amino acid substitutions at certain amino acid positions, relative to the *Ocimum basilicum* myrcene synthase of SEQ ID NO: 2. However, corresponding positions in homologs or orthologs of the *Ocimum basilicum* myrcene synthase can be readily determined by sequence alignment algorithms known in the art, and the amino acid substitutions described with reference to positions of SEQ ID NO: 2 may be applied to the homologs or orthologs of the *Ocimum basilicum* myrcene synthase (e.g., *O. campechianum, O. tenuiflorum, O. centraliafricanum*, and the like). While SEQ ID NO: 2 is derived from *Ocimum basilicum*, it is expected that other *Ocimum* species myrcene synthases or other homologous myrcene synthases may share a substantial sequence identity (e.g., at least 50%). The homologous myrcene synthases of *Ocimum basilicum* myrcene synthase may also hybridize under stringent conditions to the complement of a nucleic acid sequence encoding SEQ ID NO: 2 (e.g., a nucleotide sequence of SEQ ID NO: 1). The amino acid substitutions at one or more positions relative to SEQ ID NO: 2 may be incorporated into other *Ocimum* species myrcene synthases or other homologous sequences (e.g., having at least 70%, 80%, 90%, or 95% sequence identity to SEQ ID NO: 2) to generate additional myrcene synthase variants which retain or possess improved myrcene synthase activity compared to the parent myrcene synthase.

Thus, in certain embodiments, a myrcene synthase variant comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises one or more variant amino acid residues compared to SEQ ID NO: 2 at one or more positions selected from the group consisting of positions 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2.

In other embodiments, a myrcene synthase variant comprises an amino acid sequence that is encoded by a nucleic acid molecule that hybridizes under stringent hybridization conditions to the complement of SEQ ID NO: 1, and comprises one or more variant amino acid residues compared to SEQ ID NO: 2 at one or more positions selected from the group consisting of positions 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In some embodiments, a myrcene synthase variant is encoded by a nucleic acid molecule that hybridizes under stringent conditions to the complement of SEQ ID NO: 3 and comprises at least one variant amino acid residue compared to SEQ ID NO: 2 at one or more positions selected from the group consisting of positions 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. The nucleotide sequence of SEQ ID NO: 3 encodes the amino acid sequence of SEQ ID ON: 2 and is a codon optimized version of SEQ ID NO: 1 for expression in yeast host cells (e.g., *S. cerevisiae*).

In certain embodiments, the myrcene synthase variant has an amino acid sequence shown in SEQ ID NO: 2 but comprises a histidine to isoleucine substitution at position 27 (H27I). In certain embodiments, the myrcene synthase variant has an amino acid sequence shown in SEQ ID NO: 2 but comprises a histidine to cysteine substitution at position 27 (H27C). In certain embodiments, the myrcene synthase variant has an amino acid sequence shown in SEQ ID NO: 2 but comprises a serine to histidine substitution at position 28 (S28H). In certain embodiments, the myrcene synthase variant has an amino acid sequence shown in SEQ ID NO: 2 but comprises an isoleucine to valine substitution at position 207 (I207V). In certain embodiments, the myrcene synthase variant has an amino acid sequence shown in SEQ ID NO: 2 but comprises a lysine to cysteine substitution at position 213 (K213C). In certain embodiments, the myrcene synthase variant has an amino acid sequence shown in SEQ ID NO: 2 but comprises a lysine to histidine substitution at position 213 (K213H). In certain embodiments, the myrcene synthase variant has an amino acid sequence shown in SEQ ID NO: 2 but comprises a lysine to arginine substitution at position 213 (K213R). In certain embodiments, the myrcene synthase variant has an amino acid sequence shown in SEQ ID NO: 2 but comprises a lysine to valine substitution at position 213 (K213V). In certain embodiments, the myrcene synthase variant has an amino acid sequence shown in SEQ ID NO: 2 but comprises an arginine to asparagine substitution at position 222 (R222N). In certain embodiments, the myrcene synthase variant has an amino acid sequence shown in SEQ ID NO: 2 but comprises a cysteine to leucine substitution at position 342 (C342L). In certain embodiments, the myrcene synthase variant has an amino acid sequence shown in SEQ ID NO: 2 but comprises a tyrosine to arginine substitution (Y347R). In certain embodiments, the myrcene synthase variant has an amino acid sequence shown in SEQ ID NO: 2 but comprises a phenylalanine to leucine substitution at position 381 (F381L). In certain embodiments, the myrcene synthase variant has an amino acid sequence shown in SEQ ID NO: 2 but comprises a valine to leucine substitution at position 382 (V382L). In certain embodiments, the myrcene synthase variant has an amino acid sequence shown in SEQ ID NO: 2 but comprises an aspartic acid to glycine substitution at position 389 (D389G). In certain embodiments, the myrcene synthase variant has an amino acid sequence shown in SEQ ID NO: 2 but comprises an aspartic acid to serine substitution at position 389 (D389S). In certain embodiments, the myrcene synthase variant has an amino acid sequence shown in SEQ ID NO: 2 but comprises a glycine to aspartic acid substitution at position 390 (G390D). In certain embodiments, the myrcene synthase variant has an amino acid sequence shown in SEQ ID NO: 2 but comprises an asparagine to isoleucine substitution at position 401 (N401I). In certain embodiments, the myrcene synthase variant has an amino acid sequence shown in SEQ ID NO: 2 but comprises an asparagine to valine substitution at position 401 (N401V). In certain embodiments, the myrcene synthase variant has an amino acid sequence shown in SEQ ID NO: 2 but comprises an isoleucine to valine substitution at position 404 (I404V). In certain embodiments, the myrcene synthase variant has an amino acid sequence shown in SEQ ID NO: 2 but comprises a valine to leucine substitution at position 428 (V428L). In certain embodiments, the myrcene synthase variant has an amino acid sequence shown in SEQ ID NO: 2 but comprises a tyrosine to leucine substitution at position 439 (Y439L). In certain embodiments, the myrcene synthase variant has an amino acid sequence shown in SEQ ID NO: 2 but comprises an alanine to cysteine substitution at position 466 (A466C). In certain embodiments, the myrcene synthase variant has an amino acid sequence shown in SEQ ID NO: 2 but comprises an alanine to serine substitution at position 466 (A466S). In certain embodiments, the myrcene synthase variant has an amino acid sequence shown in SEQ ID NO: 2 but comprises an arginine to cysteine substitution at position 482 (R482C). In certain embodiments, the myrcene synthase variant has an amino acid sequence shown in SEQ ID NO: 2 but comprises an arginine to aspartic acid substitution at position 482 (R482D). In certain embodiments, the myrcene synthase variant has an amino acid sequence shown in SEQ ID NO: 2 but comprises an arginine to histidine substitution at position 482 (R482H). In certain embodiments, the myrcene synthase variant has an amino acid sequence shown in SEQ ID NO: 2 but comprises an arginine to isoleucine substitution at position 482 (R482I). In certain embodiments, the myrcene synthase variant has an amino acid sequence shown in SEQ ID NO: 2 but comprises an arginine to leucine substitution at position 482 (R482L). In certain embodiments, the myrcene synthase variant has an amino acid sequence shown in SEQ ID NO: 2 but comprises an arginine to asparagine substitution at position 482 (R482N). In certain embodiments, the myrcene synthase variant has an amino acid sequence shown in SEQ ID NO: 2 but comprises an arginine to valine substitution (R482V). In certain embodiments, the myrcene synthase variant has an amino acid sequence shown in SEQ ID NO: 2 but comprises a histidine to tyrosine substitution at position 484 (H484Y). In certain embodiments, the myrcene synthase variant has an amino acid sequence shown in SEQ ID NO: 2 but comprises a cysteine to isoleucine substitution at position 505 (C505I). In certain embodiments, the myrcene synthase variant has an amino acid sequence shown in SEQ ID NO: 2 but comprises a cysteine to leucine substitution at position 505 (C505L). In certain embodiments, the myrcene synthase variant has an amino acid sequence shown in SEQ ID NO: 2 but comprises a cysteine to valine substitution (C505V). In certain embodiments, the myrcene synthase variant has an amino acid sequence shown in SEQ ID NO: 2 but comprises a glycine to leucine substitution at position 514 (G514L). In certain embodiments, the myrcene synthase variant has an amino acid sequence shown in SEQ ID NO: 2 but comprises a glycine to valine substitution at position 514 (G514V). In certain embodiments, the myrcene synthase variant has an amino acid sequence shown in SEQ ID NO: 2 but comprises a serine to glycine substitution at position 517 (S517G). In certain embodiments, the myrcene synthase variant has an amino acid sequence shown in SEQ ID NO: 2 but comprises a phenylalanine to leucine substitution at position 524 (F524L). In certain embodiments, the myrcene synthase variant has an amino acid sequence shown in SEQ ID NO: 2 but comprises a phenylalanine to valine substitution at position 524 (F524V). In certain embodiments, the myrcene synthase variant has an amino acid sequence shown in SEQ ID NO: 2 but comprises a valine to cysteine substitution at position 527 (V527C). In certain embodiments, the myrcene synthase variant has an amino acid sequence shown in SEQ ID NO: 2 but comprises a valine to phenylalanine substitution at position 527 (V527F). In certain embodiments, the myrcene synthase variant has an amino acid sequence shown in SEQ ID NO: 2 but comprises a valine to histidine substitution at position 527 (V527H). In certain embodiments, the myrcene synthase variant has an amino acid sequence shown in SEQ ID NO: 2 but comprises a valine to leucine substitution at position 527 (V527L). In certain embodiments, the myrcene synthase variant has an amino acid sequence shown in SEQ ID NO: 2 but comprises a valine to asparagine substitution at position 527 (V527N). In certain embodiments, the myrcene synthase variant has an amino acid sequence shown in SEQ ID NO: 2 but comprises a valine to serine substitution at position 527 (V527S). In certain embodiments, the myrcene synthase variant has an amino acid sequence shown in SEQ ID NO: 2 but comprises a valine to tyrosine substitution at position 527 (V527Y). In certain embodiments, the myrcene synthase variant has an amino acid sequence shown in SEQ ID NO: 2 but comprises a glutamic acid to aspartic acid substitution at position 528 (E528D). In certain embodiments, the myrcene synthase variant has an amino acid sequence shown in SEQ ID NO: 2 but comprises a methionine to isoleucine substitution at position 543 (M543I). In certain embodiments, the myrcene synthase variant has an amino acid sequence shown in SEQ ID NO: 2 but comprises an alanine to serine substitution at position 544 (A544S). In certain embodiments, the myrcene synthase variant has an amino acid sequence shown in SEQ ID NO: 2 but comprises a glutamine to arginine substitution at position 552 (Q552R). In certain embodiments, the myrcene synthase variant has any combination of amino acid substitutions described herein.

In certain embodiments, provided herein are myrcene synthase variants which comprise an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2 and comprises at least one variant amino acid residue compared to SEQ ID NO: 2, wherein at least one variant amino acid residue is selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the position of amino acid residue is numbered with reference to SEQ ID NO: 2.

In certain embodiments, provided herein are myrcene synthase variants which are encoded by a nucleic acid molecule that hybridizes under stringent conditions to the complement of SEQ ID NO: 1, SEQ ID NO: 3, or SEQ ID NO: 4 and comprises at least one variant amino acid residue compared to SEQ ID NO: 2, wherein at least one variant amino acid residues selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the position of amino acid residue is numbered with reference to SEQ ID NO: 2.

In certain embodiments, a myrcene synthase variant comprises one variant amino acid residue compared to SEQ ID NO: 2. In certain embodiments, a myrcene synthase variant comprises two variant amino acid residues compared to SEQ ID NO: 2. In certain embodiments, a myrcene synthase variant comprises three variant amino acid residues compared to SEQ ID NO: 2. In certain embodiments, a variant myrcene synthase comprises four variant amino acid residues compared to SEQ ID NO: 2. In certain embodiments, a myrcene synthase variant comprises five variant amino acid residues compared to SEQ ID NO: 2. In certain embodiments, a myrcene synthase variant comprises at least 6, 7, 8, 9, 10, 11, 12, 13, 14, 15, 16, 17, 18, 19, 20, or more amino acid substitutions compared to SEQ ID NO: 2.

In certain embodiments, a myrcene synthase variant comprises at least one set of variant amino acid residues compared to SEQ ID NO: 2, and wherein the at least one set of variant amino acid residues is selected from the group of sets of variant amino acid residues consisting of: (a) F381L, I404V, E528D, and M543I; (b) I404V and E528D; (c) F381L, D389G, I404V, Y439L, and E528D; (d) F381L, E528D, and M543I; (e) F381L, I404V, and E528D; (f) F381L, I404V, E528D, and A544S; and (g) F381L, I404V, E528D, and Q552R, wherein the position is numbered with reference to SEQ ID NO: 2. As described in the examples section, each of these sets of variant amino acid residues, when introduced into the background of SEQ ID NO: 2, further improves the myrcene synthase activity relative to the reference myrcene synthase comprising SEQ ID NO: 2. One or more of these sets of variant amino acid residues may also be introduced into homologous sequences of SEQ ID NO: 2.

As described in the examples section, a myrcene synthase variant which comprises a set of variant amino acid residues F381L, I404V, and E528D was found to exhibit about a 14-fold increase in the myrcene synthase activity relative to the reference myrcene synthase comprising a sequence of SEQ ID NO: 2, when encoded by the wild-type nucleotide sequence having SEQ ID NO: 1, in microbial host cells (e.g., S. cerevisiae). Thus, in certain embodiments, one or more variant amino acid residues can be further introduced into this myrcene synthase variant (referred to as "14×ObMS" variant) to generate additional myrcene synthase variants with improved myrcene synthase activities. For example, additional myrcene synthase variants may be generated by introducing into the 14×ObMS variant, one or more variant amino acid residues, such as H27I, H27C, S28H, I207V, K213C, K213H, K213R, K213V, R222N, C342L, Y347R, V382L, D389G, D389S, G390D, N401I, N401V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, M543I, A544S, and Q552R.

In addition to specific amino acid substitutions described herein, other variations of amino acid substitutions, deletions, additions, and insertions in the reference myrcene synthases are within the scope of the present invention. The function of these myrcene synthase variants can be readily determined by expressing each variant in microbial host cells and measuring production of myrcene using plate assays, headspace assays, competition assays, and GC techniques described in the examples section or other suitable techniques known in the art.

As shown in the examples section, the amino acid substitutions in myrcene synthase variants described herein change in vivo performance of the reference myrcene synthase, that is, their ability to convert a geranyl pyrophosphate substrate to a myrcene when expressed in microbial host cells. Without wishing to be bound by any theory, changes in in vivo performance of myrcene synthase variants may be due to changes in binding affinity for substrates, enzyme kinetics, transcription, protein expression level, protein stability, and the like. In certain embodiments, myrcene synthase variants may also alter substrate utilization or monoterpene product distribution.

In certain embodiments, changes in in vivo performance of myrcene synthase variants can be assessed by measuring and comparing myrcene production with that of a reference myrcene synthase (e.g., wild-type myrcene synthase of Ocimum basilicum) under the same culture conditions. The myrcene production can be measured in terms of titer, yield and/or productivity using any suitable techniques known in the art. For example, the myrcene production can be measured using culture conditions and myrcene titer analysis techniques described in the examples section.

In certain embodiments, the myrcene production by a myrcene synthase variant, when expressed in genetically modified microbial host cells, is at least 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold higher than the myrcene production by a reference myrcene synthase. In certain embodiments, the fold increase in myrcene production by a myrcene synthase variant is compared to the myrcene production by the reference myrcene synthase, wherein the reference myrcene synthase comprises SEQ ID NO: 2 which is encoded by SEQ ID NO: 1. In an embodiment, the myrcene production is measured using GC techniques described in Examples 6.4 and 6.5 in the examples section. The myrcene production is compared between the variant and reference myrcene synthases under equivalent experimental conditions (e.g., host cell, control sequences, culture conditions, and the like).

In other embodiments, changes in in vivo performance of myrcene synthase variants can be assessed by measuring myrcene titer and a comparison monoterpene titer in a competition assay. An illustrative example of a competition assay employs a known monoterpene synthase (e.g., a limonene synthase) as the comparison enzyme against which myrcene synthase variants are compared. Both the comparison monoterpene synthase and each of the myrcene synthase variants are co-expressed in a microbial host cell in which they then compete for the same substrate (e.g., geranyl pyrophosphate) to produce their corresponding monoterpenes. Since the performance of the comparison enzyme remains constant in the genetically modified microbial host cells, any changes in the ratios of titers of the monoterpenes produced by the test myrcene synthase variant and the comparison monoterpene synthase are the direct result of the activities of the myrcene synthase variants. For example, if a limonene synthase is used as the comparison enzyme, then the ratios of titers of myrcene and limonene can be measured for each myrcene synthase variant. Consequently, such ratios can be used to identify myrcene synthase variants with improved in vivo performance, and/or to quantitatively compare the myrcene synthase variants for their in vivo kinetic capacities in diverting geranyl pyrophosphate to the production of myrcene. An exemplary competition assay that is suitable for use in screening is further described in the examples section.

In certain embodiments, myrcene synthase variants exhibit improved ratios of titer of myrcene and a comparison monoterpene synthase (e.g., limonene synthase) by at least 5%, at least 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold than the ratio of titer of myrcene and comparison monoterpene (e.g., limonene) produced by a reference myrcene synthase (e.g., wild-type myrcene synthase comprising SEQ ID NO: 2 which is encoded by SEQ ID NO: 1).

In certain embodiments, an additional assay may be performed to determine whether a myrcene synthase variant has retained or improved the monoterpene product profile by comparing the product profile of the myrcene synthase variant with that of a reference myrcene synthase. As shown in Example 7.7, the wild-type myrcene synthase comprising SEQ ID NO: 2, when expressed in genetically modified microbial host cells, produces between about 89% to 92% myrcene compared to the total amount of monoterpenes produced by the genetically modified microbial host cells. It may be desirable to screen for myrcene synthase variants which are capable of producing myrcene at even a higher proportion, for example, at least about 93%, 94%, 95%, 96%, 97%, 98%, or 99% myrcene, compared to the wild-type myrcene synthase comprising SEQ ID NO: 2. GC techniques described in the example section can be used to determine whether a myrcene synthase variant has at least retained its monoterpene product profile or improved its product profile by increasing the proportion of myrcene in the monoterpenes produced by the genetically modified microbial host cells.

The assays described above are merely exemplary, and other suitable assays to determine in vivo performance of myrcene synthase variants apparent to those skilled in the art may be utilized to screen myrcene synthase variants with improved in vivo performance.

6.3.2. Myrcene Synthase Variant Nucleic Acid Sequences

In another aspect, provided herein are isolated nucleic acid molecules that encode myrcene synthases described herein. In certain embodiments, the isolated nucleic acid molecules may comprise nucleotide substitutions, deletions, additions, and/or insertions to SEQ ID NO: 1, which may or may not result in changes in the corresponding amino acid sequences. In certain embodiments, the isolated nucleic acid molecules may comprise nucleotide substitutions, deletions, additions, and/or insertions into homologous sequences of SEQ ID NO: 1 which encode myrcene synthases. In certain embodiments, modifications to the isolated nucleic acid molecules may be silent due to degeneracy of the genetic code, and the protein encoded by the variant is identical to the protein encoded by the reference nucleotide sequence. In certain embodiments, modifications to the isolated nucleic acid molecules may cause substitutions of amino acids in the protein encoded by the variant compared to the protein encoded by the reference nucleotide sequence.

In some embodiments where nucleotide changes do not result in changes to the amino acid sequence, the changes may nonetheless result in improved activity of the myrcene synthase, for example, through codon optimization. The codons for nucleic acid molecules encoding myrcene synthases can be optimized for any selected microbial host cell. In some embodiments, the nucleotide sequence encoding the myrcene synthase is altered to reflect the codon preferences of *Saccharomyces cerevisiae* (see, e.g., Bennetzen and Hall (1982) *J. Biol. Chem.* 257(6): 3026-3031). In some embodiments, the nucleotide sequence encoding the myrcene synthase is altered to reflect the codon preferences for *Escherichia coli* (see, e.g., Gouy and Gautier (1982) *Nucleic Acids Res.* 10(22):7055-7074; Eyre-Walker (1996) *Mol. Biol. Evol.* 13(6): 864-872; Nakamura et al. (2000) *Nucleic Acids Res.* 28(1):292). Codon optimization for other microbial host cells can be readily determined using codon usage tables or can be performed using commercially available software, such as CodonOp (https://www.idtdna.com/CodonOptfrom) from Integrated DNA Technologies.

In one embodiment, provided herein is an isolated nucleic acid molecule comprising the nucleotide sequence shown in SEQ ID NO: 3. The nucleotide sequence of SEQ ID NO: 3 includes distinct codon optimizations for expression in yeast host cells (e.g., *S. cerevisiae*). The nucleotide sequence having SEQ ID NO: 3 is referred to as the 5×ObMS variant nucleotide sequence. In certain embodiments, when the 5×ObMS is expressed in genetically modified microbial host cells, it exhibits about a five-fold increase in myrcene synthase activity compared to the 1×ObMS (wild-type *O. basilicum* myrcene synthase nucleic acid molecule comprising SEQ ID NO: 1, which is not codon optimized) in a competition assay as described in the examples section. The codon optimized nucleotide sequence shown in SEQ ID NO: 3 for yeast host cells is merely exemplary, and other codon optimized nucleotide sequences for yeast or other microbial host cells can be generated using codon usage tables or codon optimizing software.

In certain embodiments, provided herein are isolated nucleic acid molecules that encode variant myrcene synthases described above. For instance, isolated nucleic acid molecules encode myrcene synthase variants which comprise an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2. In certain embodiments, isolated nucleic acid molecules encode myrcene synthase variants comprising an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises at least one variant amino acid residue compared to SEQ ID NO: 2 at one or more of positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In certain embodiments, the isolated nucleic acid molecules encoding myrcene synthase variants are not naturally occurring nucleic acid molecules.

In certain embodiments, provided herein are isolated nucleic acid molecules that hybridize under stringent conditions to the complement of SEQ ID NO: 1 and encode myrcene synthase variants comprising at least one variant amino acid residue compared to SEQ ID NO: 2 at one or more of positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. In certain embodiments, provided herein are isolated nucleic acid molecules that hybridize under stringent conditions to the complement of SEQ ID NO: 3 and encodes a myrcene synthase variant comprising at least one variant amino acid residue compared to SEQ ID NO: 2 at one or more of positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. As described above, the nucleotide sequence of SEQ ID NO: 3 encodes the amino acid sequence of SEQ ID ON: 2 and is a codon optimized version of SEQ ID NO: 1 for expression in yeast host cells (e.g., *S. cerevisiae*). In certain embodiments, provided herein are isolated nucleic acid molecules that hybridize under stringent conditions to the complement of SEQ ID NO: 4 and encodes a myrcene synthase variant comprising at least one variant amino acid residue compared to SEQ ID NO: 2 at one or more of positions selected from the group consisting of 27, 28, 207, 213, 222, 342, 347, 381, 382, 389, 390, 401, 404, 428, 439, 466, 482, 484, 505, 514, 517, 524, 527, 528, 543, 544, and 552, wherein the positions are numbered with reference to SEQ ID NO: 2. The nucleotide sequence of SEQ ID NO: 4 encodes the amino acid sequence of SEQ ID NO: 2 with three amino acid substitutions F381L, I404V, and E528D, wherein the positions are numbered with reference to SEQ ID NO: 2.

In certain embodiments, provided herein are isolated nucleic acid molecules encoding myrcene synthase variants which comprise an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2 and comprises at least one variant amino acid residue compared to SEQ ID NO: 2, wherein at least one variant amino acid residue is selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2. In certain embodiments, provided herein are isolated nucleic acid molecules that hybridize under stringent conditions to the complement of SEQ ID NOS: 1, 3, or 4, and encode myrcene synthase variants comprising at least one variant amino acid residue compared to SEQ ID NO: 2, wherein at least one variant amino acid residue is selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2.

In certain embodiments, provided herein are isolated nucleic acid molecules encoding myrcene synthase variants which comprise at least one set of variant amino acid residues compared to SEQ ID NO: 2, wherein at least one set of variant amino acid residues is selected from the group of sets of variant amino acid residues consisting of: (a) F381L, I404V, E528D, and M543I; (b) I404V and E528D; (c) F381L, D389G, I404V, Y439L, and E528D; (d) F381L, E528D, and M543I; (e) F381L, I404V, and E528D; (f) F381L, I404V, E528D, and A544S; and (g) F381L, I404V, E528D, and Q552R, wherein the positions are numbered with reference to SEQ ID NO: 2. In certain embodiments, provided herein are isolated nucleic acid molecules that hybridize under stringent conditions to the complement of SEQ ID NOS: 1, 3, or 4, and encode myrcene synthase variants comprising at least one set of variant amino acid residues compared to SEQ ID NO: 2, and wherein at least one set of variant amino acid residues is selected from the group of sets of variant amino acid residues consisting of: (a) F381L, I404V, E528D, and M543I; (b) I404V and E528D; (c) F381L, D389G, I404V, Y439L, and E528D; (d) F381L, E528D, and M543I; (e) F381L, I404V, and E528D;(f) F381L, I404V, E528D, and A544S; and (g) F381L, I404V, E528D, and Q552R, wherein the positions are numbered with reference to SEQ ID NO: 2.

In certain embodiments, isolated nucleic acid molecules encoding myrcene synthase variants may be generated using the nucleotide sequence having SEQ ID NO: 3 (which is codon optimized) as a background nucleotide sequence for replacing specific codons to encode a variant myrcene synthase. For example, SEQ ID NO: 4 is generated by using SEQ ID NO: 3 as the background nucleotide sequence with three codons replaced to encode a myrcene synthase variant comprising three variant amino acid residues F381L, I404V, and E528D compared to SEQ ID NO: 2, wherein the positions are numbered with reference to SEQ ID NO: 2. As described in the examples section, when the nucleic acid molecule comprising the sequence of SEQ ID NO: 4 was expressed in genetically modified microbial host cells, it was discovered that this myrcene synthase variant (also referred to as the 14×ObMS) exhibited about a 14-fold increase in the myrcene synthase activity compared to genetically modified microbial host cells expressing wild-type myrcene synthase encoded by a nucleic acid sequence comprising SEQ ID NO: 1.

Additional myrcene synthase variant nucleic acid molecules can be produced using any suitable genetic engineering techniques known in the art. These techniques include, for example, error-prone PCR, shuffling, oligonucleotide-directed mutagenesis, assembly PCR, site-specific mutagenesis, cassette mutagenesis, and the like. Furthermore, combinatorial libraries based on saturation mutagenesis may be generated to engineer additional myrcene synthase variant nucleic acid molecules that result in enhanced in vivo performance of myrcene synthases.

6.4 Other Enzymes for Co-Expression with Myrcene Synthase for Biosynthesis of Myrcene In another aspect, the myrcene synthases described herein can be co-expressed with other enzymes for biosynthesis of myrcene in microbial host cells. In some embodiments, in addition to a heterologous nucleic acid molecule encoding a myrcene synthase, microbial host cells can be genetically modified to include heterologous nucleic acid molecules encoding one or more enzymes of the MEV pathway. In other embodiments, in addition to a heterologous nucleic acid molecule encoding a myrcene synthase, microbial host cells can be genetically modified to include one or more heterologous nucleic acid molecules encoding one or more enzymes of the DXP pathway. In another embodiment, in addition to a heterologous nucleic acid molecule encoding a myrcene synthase, microbial host cells can be genetically modified to comprise a heterologous nucleic acid molecule encoding a geranyl pyrophosphate synthase. In yet another embodiment, the microbial host cells can be genetically modified to include any combination of these and other heterologous nucleic acid molecules.

6.4.1. Geranyl Pyrophosphate Synthase

In certain embodiments, a myrcene synthase provided herein is co-expressed with a geranyl pyrophosphate synthase (GPPS). A GPPS is an enzyme that can condense one molecule of isopentenyl pyrophosphate (IPP) with one molecule of dimethylallyl pyrophosphate (DMAPP) to form one molecule of geranyl pyrophosphate ("GPP"). As shown in FIG. 1, geranyl pyrophosphate is a precursor for myrcene synthases. Thus, in some embodiments, a heterologous nucleic acid molecule encoding a geranyl pyrophosphate synthase (GPPS) can be introduced together with a heterologous nucleic acid molecule encoding a myrcene synthase into microbial host cells to catalyze the formation of a GPP substrate for the myrcene synthase. In some embodiments, the GPPS nucleotide sequences may be modified (e.g., codon optimized, truncated, mutagenized, and the like) prior to co-expressing the GPPS sequence together with a myrcene synthase sequence.

Illustrative examples of nucleotide sequences encoding such a GPPS include, but are not limited to: (AF513111;

*Abies grandis*), (AF513112; AF513112.1 *Abies grandis*), (AF513113; *Abies grandis*), (AY534686; *Antirrhinum majus*), (AY534687; *Antirrhinum majus*), (AA82860; *Antirrhinum majus*), (AA82859; *Antirrhinum majus*), (ACQ90682; *Humulus lupulus*), (ACQ90681; *Humulus lupulus*) (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Menthaxpiperita*), (AF182827; *Menthax piperita*), (MPI249453; *Menthaxpiperita*), (PZE431697, Locus CAD24425; *Paracoccus zeaxanthinifaciens*), (AY866498; *Picrorhiza kurrooa*), (AY351862; *Vitis vinifera*), (AF203881, Locus AAF12843; *Zymomonas mobilis*), (ABS50454; *Streptomyces culeolatus*); (AAR08151; *Vitis vinifera*), and (JX417185; *Catharanthus roseus*), (JX417183; *Catharanthus roseus*), (JX417184; *Catharanthus roseus*), (AEZ55677; *Salvia miltiorrhiza*), (AEZ55681; *Salvia miltiorrhiza*), (AEZ55678; *Salvia miltiorrhiza*), (AFJ52721; *Mangifera indica*), (AFJ52722; *Mangifera indica*), (GQ369788; *Picea abies*), (EU432047; *Picea abies*), (ABY90133; *Glycine max*), (AEL29573; *Medicago sativa*), (ABV71395; *Phalaenopsis bellina*), and (BAH90987; *Oryza sativa* subsp. *japonica*).

Among many of these known sequences, the present inventors found that bacterial geranyl pyrophosphate synthase sequences, such as those derived from *Streptomyces aculeolatus*, are particularly useful. For example, a codon optimized *Streptomyces aculeolatus* geranyl pyrophosphate synthase (SaGPPS), when co-expressed with myrcene synthases described herein, exhibits sufficient enzyme activity in microbial host cells to support normal strain growth and a relatively high level of myrcene production. See, e.g., Example 7.8 for comparison with other GPPS sequences for myrcene production. Thus, in certain embodiments, the compositions and methods provided herein utilize bacterial geranyl pyrophosphate synthases, in particular SaGPPS, for the production of myrcene in microbial host cells. In an embodiment, SaGGPS comprising an amino acid sequence of SEQ ID NO: 7 or its homologous sequences may be used in the compositions and methods provided herein. In another embodiment, a codon optimized SaGPPS nucleic acid molecule comprising the nucleotide sequence of SEQ ID NO: 6 may be used in the compositions and methods provided herein.

6.4.2. MEV Pathway Enzymes

In some embodiments, the myrcene synthases provided herein are co-expressed with one or more heterologous nucleic acid molecules encoding one or more mevalonate pathway enzymes in microbial host cells. FIG. 1 and FIG. 2A illustrate one example of the mevalonate pathway. In certain embodiments, this biosynthetic pathway can be used in genetically modified microbial host cells to provide sufficient carbon flow for the production of dimethylallyl pyrophosphate (DMAPP) and isopentenyl pyrophosphate (IPP), which, in turn, can be used for production of geranyl pyrophosphate and myrcene. Thus, in certain embodiments, the genetically modified microbial host cells comprise one or more heterologous nucleic acid molecules encoding one or more enzymes of the mevalonate pathway, which effects increased production of myrcene as compared to a genetically unmodified parent cell.

In some embodiments, the myrcene producing microbial host cell can be further genetically modified to comprise a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC 000913 REGION: 2324131.2325315; *Escherichia coli*), (D49362; *Paracoccus denitrificans*), and (L20428; *Saccharomyces cerevisiae*).

In some embodiments, the myrcene producing microbial host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the myrcene producing microbial host cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the myrcene producing microbial host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the myrcene producing microbial host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

In some embodiments, the myrcene producing microbial host cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

In some embodiments, the myrcene producing microbial host cell comprises one or more heterologous nucleotide sequences encoding more than one enzyme of the MEV pathway. In some embodiments, the myrcene producing microbial host cell comprises one or more heterologous nucleotide sequences encoding two enzymes of the MEV pathway. In some embodiments, the myrcene producing microbial host cell comprises one or more heterologous nucleotide sequences encoding an enzyme that can convert HMG-CoA into mevalonate and an enzyme that can convert mevalonate into mevalonate 5-phosphate. In some embodiments, the myrcene producing microbial host cell comprises one or more heterologous nucleotide sequences encoding three enzymes of the MEV pathway. In some embodiments, the myrcene producing microbial host cell comprises one or more heterologous nucleotide sequences encoding four enzymes of the MEV pathway. In some embodiments, the myrcene producing microbial host cell comprises one or more heterologous nucleotide sequences encoding five enzymes of the MEV pathway. In some embodiments, the myrcene producing microbial host cell comprises one or more heterologous nucleotide sequences encoding six enzymes of the MEV pathway. In some embodiments, the myrcene producing microbial host cell further comprises a heterologous nucleotide sequence encoding an enzyme that can convert IPP generated via the mevalonate pathway into its isomer, dimethylallyl pyrophosphate ("DMAPP"). IPP and DMAPP can be condensed and modified through the action of geranyl pyrophosphate synthase and myrcene synthase to produce myrcene (FIG. 1 and FIG. 2A).

6.4.3. DXP Pathway Enzymes

In some embodiments of the methods provided herein, the myrcene producing microbial host cell comprises one or more heterologous nucleotide sequences encoding one or more enzymes of the DXP pathway, which effects increased production of one or more myrcene as compared to a genetically unmodified parent cell. The DXP pathway shown in FIG. 2B is an alternative biosynthetic pathway for producing intermediate metabolites, such as DMAPP, which can be catalyzed for the formation of GPP.

In some embodiments, the myrcene producing microbial host cell comprises a heterologous nucleotide sequence encoding an enzyme, e.g., 1-deoxy-D-xylulose-5-phosphate synthase, which can condense pyruvate with D-glyceraldehyde 3-phosphate to make 1-deoxy-D-xylulose-5-phosphate. Illustrative examples of nucleotide sequences encoding such an enzyme include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula*1), and (NC_003076, locus tag AT5G11380; *Arabidopsis thaliana*).

In some embodiments, the myrcene producing microbial host cell comprises a heterologous nucleotide sequence encoding an enzyme, e.g., 1-deoxy-D-xylulose-5-phosphate reductoisomerase, which can convert 1-deoxy-D-xylulose-5-phosphate to 2C-methyl-D-erythritol-4-phosphate. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP 2709; *Rhodobacter sphaeroides* 2.4.1), and (NC_007492, locus tag Pfl_1107; *Pseudomonas fluorescens* PfO-1).

In some embodiments, the myrcene producing microbial host cell comprises a heterologous nucleotide sequence encoding an enzyme, e.g., 4-diphosphocytidyl-2C-methyl-D-erythritol synthase, which can convert 2C-methyl-D-erythritol-4-phosphate to 4-diphosphocytidyl-2C-methyl-D-erythritol. Illustrative examples of nucleotide sequences include but are not limited to: (AF230736; *Escherichia coli*), (NC_007493, locus tag RSP 2835; *Rhodobacter sphaeroides* 2.4.1), (NC_003071, locus tag AT2G02500; *Arabidopsis thaliana*), and (NC_002947, locus tag PP1614; *Pseudomonas putida* KT2440).

In some embodiments, the myrcene producing microbial host cell comprises a heterologous nucleotide sequence encoding an enzyme, e.g., 4-diphosphocytidyl-2C-methyl-D-erythritol kinase, which can convert 4-diphosphocytidyl-2C-methyl-D-erythritol to 4-diphosphocytidyl-2C-methyl-D-erythritol-2-phosphate. Illustrative examples of nucleotide sequences include but are not limited to: (AF216300; *Escherichia coli*) and (NC_007493, locus tag RSP_1779; *Rhodobacter sphaeroides* 2.4.1).

In some embodiments, the myrcene producing microbial host cell comprises a heterologous nucleotide sequence encoding an enzyme, 2C-methyl-D-erythritol 2,4-cyclodiphosphate synthase, which can convert 4-diphosphocytidyl-2C-methyl-D-erythritol-2-phosphate to 2C-methyl-D-erythritol 2,4-cyclodiphosphate. Illustrative examples of nucleotide sequences include but are not limited to: (AF230738; *Escherichia coli*), (NC_007493, locus tag RSP_6071; *Rhodobacter sphaeroides* 2.4.1), and (NC_002947, locus tag PP1618; *Pseudomonas putida* KT2440).

In some embodiments, the myrcene producing microbial host cell comprises a heterologous nucleotide sequence encoding an enzyme, e.g., 1-hydroxy-2-methyl-2-(E)-butenyl-4-diphosphate synthase, which can convert 2C-methyl-D-erythritol 2,4-cyclodiphosphate to 1-hydroxy-2-methyl-2-(E)-butenyl-4-diphosphate. Illustrative examples of nucleotide sequences include but are not limited to: (AY033515; *Escherichia coli*), (NC_002947, locus tag PP0853; *Pseudomonas putida* KT2440), and (NC_007493, locus tag RSP 2982; *Rhodobacter sphaeroides* 2.4.1).

In some embodiments, the myrcene producing microbial host cell comprises a heterologous nucleotide sequence encoding an enzyme, e.g., isopentyl/dimethylallyl diphosphate synthase, which can convert 1-hydroxy-2-methyl-2-(E)-butenyl-4-diphosphate into either IPP or its isomer, DMAPP. Illustrative examples of nucleotide sequences include but are not limited to: (AY062212; *Escherichia coli*) and (NC_002947, locus tag PP0606; *Pseudomonas putida* KT2440).

In some embodiments, the myrcene producing microbial host cell comprises one or more heterologous nucleotide sequences encoding more than one enzyme of the DXP pathway. In some embodiments, the myrcene producing microbial host cell comprises one or more heterologous nucleotide sequences encoding two enzymes of the DXP pathway. In some embodiments, the myrcene producing microbial host cell comprises one or more heterologous nucleotide sequences encoding three enzymes of the DXP pathway. In some embodiments, the myrcene producing microbial host cell comprises one or more heterologous nucleotide sequences encoding four enzymes of the DXP pathway. In some embodiments, the myrcene producing microbial host cell comprises one or more heterologous nucleotide sequences encoding five enzymes of the DXP pathway. In some embodiments, the myrcene producing microbial host cell comprises one or more heterologous nucleotide sequences encoding six enzymes of the DXP pathway. In some embodiments, the myrcene producing microbial host cell comprises one or more heterologous nucleotide sequences encoding seven enzymes of the DXP pathway.

In some embodiments, the myrcene producing cell further comprises a heterologous nucleotide sequence encoding an enzyme that can convert IPP generated via the MEV pathway into DMAPP, e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

In some embodiments, "cross talk" (or interference) between the microbial host cell's own metabolic processes and those processes involved with the production of IPP are minimized or eliminated entirely. For example, cross talk is minimized or eliminated entirely when the host microorganism relies exclusively on the DXP pathway for synthesizing IPP, and a MEV pathway is introduced to provide additional IPP. Such a host organism would not be equipped to alter the expression of the MEV pathway enzymes or process the intermediates associated with the MEV pathway. Organisms that rely exclusively or predominately on the DXP pathway include, for example, *Escherichia coli*.

In some embodiments, the microbial host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

6.4.4. Modification of Other Enzymes for Biosynthesis of Myrcene and Identification of Other Useful Homologous Enzymes Described above are examples of specific biosynthetic enzymes and genes useful in the methods and compositions according to certain embodiments; however, it will be recognized that absolute identity to such enzymes and genes are not necessary. For example, the sequences of known biosynthetic pathway enzymes may be modified by substitutions, insertions, and deletions. In some embodiments, such changes comprise conservative amino acid mutations and silent mutations. In other embodiments, the nucleotide sequences encoding other biosynthetic pathway enzymes may be modified to reflect the codon preferences for a particular host cell as described above in relation to myrcene synthase sequences. The use of preferred codons for a particular host cell generally increases the likelihood of translation, and hence expression, of the nucleotide sequence. Furthermore, any of the genes encoding the foregoing enzymes (or any others mentioned herein or any of the regulatory elements that control or modulate expression thereof) may be optimized by genetic/protein engineering techniques, such as directed evolution and/or rational mutagenesis. For example, the activity of an enzyme in a host can be altered in a number of ways, including, but not limited to, expressing a modified form of the enzyme that has a higher or lower $K_{cat}$ or a lower or higher $K_m$ for the substrate, or expressing an altered form of the enzyme that is more or less affected by feedback or feed-forward regulation by another molecule in the pathway. The changes in a particular gene or polynucleotide comprising a sequence encoding an enzyme can be performed, and screened for expression or activity of functional enzymes using known methods in the art.

In addition, genes encoding these enzymes can be identified from other fungal, bacterial, plant or other species, and can be expressed for the modulation of this biosynthetic pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp. *stipitis*, *Torulaspora pretoriensis*, *Issatchenkia orientalis*, *SchizoSaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp. In certain embodiments, sequences encoding biosynthetic pathway enzymes may be obtained from plant species. These include, but are not limited to, *Picea abies*, *Glycine max*, *Medicago sativa*, *Phalaenopsis bellina*, *Salvia miltiorrhiza*, and *Mangifera indica*.

Techniques known to those skilled in the art may be suitable to identify additional homologous genes and homologous enzymes. Generally, homologous genes and/or homologous enzymes can be identified by functional analysis and will have functional similarities. Techniques known to those skilled in the art may be suitable to identify analogous genes enzymes. For example, to identify homologous GGPS genes, proteins, or enzymes, techniques may include, but are not limited to, cloning a gene by PCR using primers based on a published sequence of a GPPS gene/enzyme or by degenerate PCR using degenerate primers designed to amplify a conserved region among GPPS genes. Further, one skilled in the art can use techniques to identify homologous genes, proteins, or enzymes with functional homology or similarity. Techniques include examining a cell or cell culture for the catalytic activity of an enzyme through in vitro enzyme assays for said activity (e.g. as described herein or in Kiritani, K., Branched-Chain Amino Acids Methods Enzymology, 1970), then isolating the enzyme with said activity through purification. The protein sequence of the enzyme can be determined through techniques such as Edman degradation; PCR primers to the likely nucleic acid sequence can be designed; the DNA sequence can be amplified through PCR; and the nucleic acid sequence can be cloned. To identify homologous or similar genes and/or homologous or similar enzymes, techniques also include comparison of data concerning a candidate gene or enzyme with databases such as BRENDA, KEGG, or MetaCYC. The candidate gene or enzyme may be identified within the above mentioned databases.

6.5 Preparation of Nucleic Acid Molecules, Constructs and Expression Vectors

Preparation of the nucleic acid molecules described herein can be carried out by a variety of routine recombinant techniques and synthetic procedures. Briefly, the nucleic acid molecules can be prepared from genomic DNA fragments, cDNAs, and RNAs, all of which can be extracted directly from a cell or can be recombinantly produced by various amplification processes including, but not limited to, PCR and rt-PCR. These and other recombinant techniques are described in, e.g., Sambrook et al., 2001, Molecular Cloning—A Laboratory Manual, 3rd edition, Cold Spring Harbor Laboratories, Cold Spring Harbor, N.Y., and Ausubel et al., eds. Current Edition, Current Protocols in Molecular Biology, Greene Publishing Associates and Wiley Interscience, N.Y.

Direct chemical synthesis of nucleic acid molecules typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al. (1980) *Tet. Lett.* 521:719; U.S. Pat. No. 4,500,707 to Caruthers et al.; and U.S. Pat. Nos. 5,436,327 and 5,700,637 to Southern et al.).

In addition, the nucleic acid molecules can be custom ordered through various commercial sources. These include, for example, Twist Bioscience (San Francisco, Calif.), Biomatik (Wilmington, Del.), Genescript (Piscataway, N.J.), and GeneArt gene synthesis services available through www.introgen.com.

In addition, provided herein are nucleic acid constructs comprising an isolated nucleic acid molecule operably linked to one or more control sequences that direct the expression of the coding sequence in a suitable microbial host cell under conditions compatible with the control sequences. The control sequence may include any suitable promoter sequence, transcription terminal sequence, a polyadenylation sequence, and the like. In certain embodiments, these control sequences may be any nucleotide sequences that regulate transcriptional activity in the microbial host cell of choice and may be obtained from genes encoding one or more enzymes in the biosynthetic pathway homologous or heterologous to the microbial host cell.

Various control sequences for expression in microbial host cells are well-known in the art. For example, useful promoters for expression in yeast host cells can be derived from genes homologous to the transformed microbial host cell and/or native to the production host. In some embodiments, promoters operably linked to the nucleic acid molecule are inducible. In other embodiments, the promoters operably linked to the nucleic acid molecule encoding a coding sequence are constitutive. In some embodiments, one or more nucleic acid sequences are operably linked to an inducible promoter, and one or more other nucleic acid sequences are operably linked to a constitutive promoter. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL2, GALT, and GAL10 genes). Additional promoters and other control sequences for microbial host cells are described by, e.g., Romanos et al., 1992, *Yeast* 8: 423-488; Bitter et al., 1987, *Methods in Enzymology*, 153: 516-544; and Maximizing Gene Expression, ed. Reznikoff and Gold, 2014, Elsevier.

Also provided herein are vectors comprising nucleic acid constructs comprising nucleic acid molecules encoding biosynthetic pathway enzymes including the myrcene synthases that catalyze the formation of myrcene and other monoterpenes. Vectors useful for the transformation of suitable microbial host cells are well-known in the art. In some embodiments, the vector contains control sequences directing transcription and translation of the relevant gene, a selectable marker, and sequences allowing autonomous replication or chromosomal integration. Suitable vectors comprise a region 5' of the coding sequence which harbors transcriptional initial controls and a region 3' of the coding sequence which controls transcriptional termination.

The vectors may be any vector that is suitable for expressing the enzymes. Expression vectors useful for expressing polypeptide-encoding nucleotide sequences include viral vectors (e.g., retroviruses, adenoviruses and adeno-associated viruses), plasmid vectors, and cosmids. Illustrative examples of expression vectors suitable for use in yeast cells include, but are not limited to CEN/ARS and 2μ plasmids. The choice of vector will depend on the compatibility of the vector with the microbial host cells into which the vector to be introduced and the end application of the host cell. In some embodiments, the vector may be a chromosomal integration construct which further include element(s) that permits integration of the vector into the host cell's genome. In other embodiments, the vectors may be expression vectors that are autonomously replicating and exist extrachromosomally in host cells. Suitable vectors for microbial host cells are described in, e.g., "Cloning Vectors for Introducing Genes into Host cells," The ABCs of Gene Cloning, 2006, pp. 93-124, Springer US. Protein Expression, a Practical Approach, Higgins and Hames, Oxford University Press 1999. Vectors suitable for microbial host cells are also commercially available from various sources, e.g., Life Technologies, Sigma-Aldrich, New England BioLabs, and the like.

The procedures used to ligate the elements described above to construct the recombinant expression vectors or chromosomally integrating constructs are well known to those skilled in the art (see, e.g., Sambrook et al., 1989, supra).

6.6 Genetically Modified Microbial Host Cells

Provided herein are genetically modified microbial host cells that produce heterologous myrcene. The heterologous nucleic acid molecules encoding myrcene synthases, geranyl pyrophosphate synthases, and/or other biosynthetic pathway enzymes may be introduced into the microbial host cells using any suitable vectors described herein and known in the art. Methods for genetically modifying microbes using expression vectors or chromosomal constructs in a host cell are well known in the art. See, e.g., Sherman, F., et al., *Methods Yeast Genetics*, Cold Spring Harbor Laboratory, N.Y. (1978); Guthrie, C., et al. (Eds.) *Guide To Yeast Genetics and Molecular Biology* Vol. 194, Academic Press, San Diego (1991); Sambrook et al., 2001, *Molecular Cloning—A Laboratory Manual*, $3^{rd}$ edition, Cold Spring Harbor Laboratory, Cold Spring Harbor, N.Y.; and Ausubel et al., eds., Current Edition, *Current Protocols in Molecular Biology*, Greene Publishing Associates and Wiley Interscience, NY.; the disclosures of which are incorporated herein by reference.

Exemplary techniques for host cell transformation include, but are not limited to, spheroplasting, electroporation, PEG 1000 mediate transformation, and lithium acetate or lithium chloride mediated transformation. Furthermore, heterologous nucleic acid molecules may be integrated into the selected site in the host genome via any suitable techniques. For example, specific genome sites may be targeted by site specific nucleases (e.g., Zinc Finger Nucleases, Meganucleases, Transcription Activator-Like Effector Nucleases, CRISPR/Cas system) to induce targeted mutagenesis, induce targeted deletions of cellular DNA sequences, and facilitate targeted recombination of heterologous nucleic acid molecules within the targeted genomic site. See, e.g., U.S. Pat. No. 8,685,737; and Horwitz et al. (2015), Cell Systems 1, 1-9, U.S. Patent Publication No. 20030232410; 20050208489; 20050026157; 20050064474; and 20060188987, and WO 2007/014275, the disclosures of which are incorporated herein by reference in their entirety for all purposes.

In certain embodiments, the microbial host cells can further comprise genetic modifications (e.g., insertions, deletions, or modifications of nucleic acids) in such a manner as to provide the desired effect of elevating the intracellular level of geranyl pyrophosphate, of expressing the myrcene synthases described herein, or of production of myrcene. For example, the endogenous farnesyl pyrophosphate synthase in the host genome may be functionally disrupted to increase carbon flow towards production of geranyl pyrophosphate precursor and myrcene.

Furthermore, the copy number of one or more biosynthetic enzymes in a host cell may be altered by modifying the transcription of the gene that encodes the enzyme. This can be achieved for example by modifying the copy number of the nucleotide sequence encoding the enzyme, for example, by using a higher or lower copy number expression vector comprising the nucleotide sequence, or by introducing additional copies of the nucleotide sequence into the genome of the host cell. For example, 2, 3, 4, 5, 6, 7, 8, 9, 10 or more copies of a myrcene synthase gene may be chromosomally integrated into the genome of microbial host cells. In another example, 2, 3, 4, 5, 6, 7, 8, 9, 10 or more copies of a geranyl pyrophosphate synthase gene may be chromosomally integrated into the genome of microbial host cells. In certain embodiments, the copy number of a myrcene synthase gene and the copy number of a geranyl pyrophosphate synthase gene may be adjusted relative to each other to increase carbon flow toward production of myrcene. In some embodiments, the copy number of a myrcene synthase gene integrated into the genome of a microbial host cell is equal to or greater than the copy number of a geranyl pyrophosphate gene integrated into the genome of the microbial host cell.

In addition, inhibition of gene expression or decreased expression level, which results in increased production of myrcene in host cells, may be accomplished by deleting or disrupting the nucleotide sequence in the genome of the host cell, mutation, and/or gene rearrangement. It can also be carried out with the use of antisense RNA, siRNA, miRNA, ribozymes, triple stranded DNA, a trans-acting DNA binding protein such as TAL effector or CRISPR guided Cas9, and transcription and/or translation inhibitors. In addition, transposons can be employed to disrupt gene expression, for example, by inserting it between the promoter and the coding region, or between two adjacent genes to inactivate one or both genes. The additional modification may include changing the order of coding sequences on a polycistronic mRNA of an operon or breaking up an operon into individual genes each with its own control elements, or by increasing the strength of the promoter or operator to which the nucleotide sequence is operably linked. In some versions, a gene or coding sequence can be replaced with a selection marker or screenable marker. Various methods for introducing the genetic modifications described above are well known in the art and include homologous recombination, among other mechanisms. See, e.g., Green et al., Molecular Cloning: A laboratory manual, 4th ed., Cold Spring Harbor Laboratory Press (2012) and Sambrook et al., Molecular Cloning: A Laboratory Manual, 3rd ed., Cold Spring Harbor Laboratory Press (2001).

Alternatively or additionally, the copy number of an enzyme in a host cell may be altered by modifying the level of translation of an mRNA that encodes the enzyme. This can be achieved, for example, by modifying the stability of the mRNA, modifying the sequence of the ribosome binding site, modifying the distance or sequence between the ribosome binding site and the start codon of the enzyme coding sequence, modifying the entire intercistronic region located upstream of or adjacent to the 5' side of the start codon of the enzyme coding region, stabilizing the 3'-end of the mRNA transcript using hairpins and specialized sequences, and the like.

Genetic modifications of microbial host cells are not limited to the specific modifications described herein. Other suitable means for genetically modifying microbial host cells apparent to those skilled in the art are also within the scope of the present invention and can be employed to increase carbon flow through the biosynthetic pathway to increase production of myrcene.

6.6.1. Microbial Host Cells

Microbial host cells useful in the methods and compositions provided herein include any cell capable of naturally or recombinantly producing myrcene. In some embodiments, the cell is a prokaryotic cell. In some embodiments, the cell is a bacterial cell. In some embodiments, the cell is an *Escherichia coli* cell. In some embodiments, the cell is a eukaryotic cell. In some embodiments, the cell is a unicellular eukaryotic organism cell. In some embodiments, the cell is a yeast cell. In some embodiments, the cell is a *Saccharomyces cerevisiae* cell.

In some embodiments, the microbial host cell is a mycelial bacterial cell. In some embodiments, the mycelial bacterial cell is of the class actinomycetes. In particular embodiments, the mycelial bacterial cell is of the genera *Streptomyces*, for example, *Streptomyces ambofaciens, Streptomyces avermitilis, Streptomyces azureus, Streptomyces cinnamonensis, Streptomyces coelicolor, Streptomyces curacoi, Streptomyces erythraeus, Streptomyces fradiae, Streptomyces galilaeus, Streptomyces glaucescens, Streptomyces hygroscopicus, Streptomyces lividans, Streptomyces parvulus, Streptomyces peucetius, Streptomyces rimosus, Streptomyces roseofulvus, Streptomyces thermotolerans,* and *Streptomyces violaceoruber.*

In another embodiment, the microbial host cell is a fungal cell. In a more particular embodiment, the cell is a yeast cell. Yeasts useful in the methods and compositions provided herein include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis,* and *Zygozyma*, among others.

In particular embodiments, useful yeasts in the methods and compositions provided herein include *Saccharomyces cerevisiae, Pichia pastoris, SchizoSaccharomyces pombe,*

*Dekkera bruxellensis*, *Kluyveromyces lactis* (previously called *Saccharomyces lactis*), Kluveromyces *marxianus*, *Arxula adeninivorans*, or *Hansenula polymorpha* (now known as *Pichia angusta*). In some embodiments, the microbe is a strain of the genus *Candida*, such as *Candida lipolytica*, *Candida guilliermondii*, *Candida krusei*, *Candida pseudotropicalis*, or *Candida utilis*.

In a particular embodiment, the cell is a *Saccharomyces cerevisiae* cell. In some embodiments, the strain of the *Saccharomyces cerevisiae* cell is selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the strain of *Saccharomyces cerevisiae* is selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the cell is a haploid microbial cell. In other embodiments, the cell is a diploid microbial cell. In some embodiments, the cell is heterozygous. In other embodiments, the cell is homozygous other than for its mating type allele (i.e., if the cell should sporulate, the resulting four haploid microbial cells would be genetically identical except for their mating type allele, which in two of the haploid cells would be mating type a and in the other two haploid cells would be mating type alpha).

In some embodiments, the cell is suitable for industrial fermentation. In particular embodiments, the cell is conditioned to subsist under high solvent concentration, high temperature, expanded substrate utilization, nutrient limitation, oxygen limitation, osmotic stress, acidity, sulfite and bacterial contamination, or combinations thereof, which are recognized stress conditions of the industrial fermentation environment. In particular embodiments, the cell is conditioned to subsist under high mycene concentration.

6.7 Fermentation Compositions and Production of Myrcene

In another aspect, provided herein are fermentation compositions produced by genetically modified microbial host cells and methods for producing myrcene. The fermentation is performed by culturing the genetically modified microbial host cells in a culture medium comprising a carbon source under suitable culture conditions for a period of time sufficient to produce a desired biomass of host cells and/or a desired amount of myrcene.

In certain embodiments, the fermentation process is carried out in two stages—a build stage and a production stage. The build stage is carried out for a period of time sufficient to produce an amount of cellular biomass that can support production of myrcene during the production stage. The build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between 0.01 and 400 in the fermentation vessel or container in which the build stage is being carried out. In some embodiments, the build stage is carried out until an $OD_{600}$ of at least 0.01 is reached. In some embodiments, the build stage is carried out until an $OD_{600}$ of at least 0.1 is reached. In some embodiments, the build stage is carried out until an $OD_{600}$ of at least 1.0 is reached. In some embodiments, the build stage is carried out until an $OD_{600}$ of at least 10 is reached. In some embodiments, the build stage is carried out until an $OD_{600}$ of at least 100 is reached. In some embodiments, the build stage is carried out until an $OD_{600}$ of between 0.01 and 100 is reached. In some embodiments, the build stage is carried out until an $OD_{600}$ of between 0.1 and 10 is reached. In some embodiments, the build stage is carried out until an $OD_{600}$ of between 1 and 100 is reached. In other embodiments, the build stage is carried for a period of at least 12, 24, 36, 48, 60, 72, 84, 96 or more than 96 hours.

In some embodiments, the production stage is carried out for a period of time sufficient to produce a desired amount of myrcene. In some embodiments, the production stage is carried out for a period of at least 12, 24, 36, 48, 60, 72, 84, 96 or more than 96 hours. In some embodiments, the production stage is carried out for a period of between 3 and 20 days. In some embodiments, the production stage is carried for a period of 1, 2, 3, 4, 5, 6, 7, 8, 9, 10, 11, 12, 13, 14, 15, 16, 17, 18, 19, 20 or more than 20 days.

In a particular embodiment, the method of producing myrcene comprises conducting fermentation of the genetically modified host cell under aerobic conditions sufficient to allow growth and maintenance of the genetically modified host cell; then subsequently providing microaerobic fermentation conditions sufficient to induce production of myrcene (and other monoterpene co-products), and maintaining the microaerobic conditions throughout the fermentation run. In certain embodiments, the microaerobic conditions are used throughout the fermentation run. In certain embodiments, an inducing agent is added during the production stage to activate a promoter or to relieve repression of a transcriptional regulator to promote production of myrcene and other monoterpene co-products.

In another embodiment, the method of producing myrcene comprises culturing the microbial host cells in separate build and production culture media. For example, the method can comprise culturing the genetically modified microbial host cell in a build stage wherein the cell is cultured under non-producing conditions (e.g., non-inducing conditions) to produce an inoculum, then transferring the inoculum into a second fermentation medium under conditions suitable to induce myrcene production (e.g., inducing conditions), and maintaining steady state conditions in the second fermentation stage to produce a cell culture containing myrcene.

6.7.1. Culture Media and Conditions

Culture media and culture conditions for the maintenance and growth of microbial cultures are well known to those skilled in the art of microbiology or fermentation science (see, for example, Bailey et al., Biochemical Engineering Fundamentals, second edition, McGraw Hill, New York, 1986). Appropriate culture medium, pH, temperature, and requirements for aerobic, microaerobic, or anaerobic conditions may be selected depending on the specific requirements of the microbial host cell, the fermentation, and the process.

In some embodiments, the culture medium for use in the methods of producing myrcene as provided herein includes any culture medium in which a genetically modified microorganism capable of producing monoterpenes can subsist, i.e., support and maintain growth and viability. In some embodiments, the culture medium, also promotes the biosynthetic pathway necessary to produce the desired monoterpenes, in particular myrcene.

In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol. In some embodiments, the carbon source may be derived from a wide variety of crops and sources. Some non-limiting examples of suitable crops or sources include sugar cane, bagasse, *miscanthus*, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn. In other embodiments, the sugar source is cane juice or molasses. In certain embodiments, any combination of the above carbon sources may be used.

In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In certain embodiments, a liquid organic overlay may be added to the culture medium during the production stage of the fermentation. In certain embodiments, a liquid organic overlay is an immiscible organic liquid which is in contact with the aqueous culture medium, and myrcene and other co-products secreted from microorganisms can be captured in the liquid organic overlay. A liquid organic overlay can reduce evaporation of volatile monoterpenes from the fermentation vessel as well reduce potential myrcene toxicity to microorganisms. Examples of an overlay include, but are not limited to, isopropyl myristate (IPM) or other hydrocarbon liquids such as white mineral oils or polyalphaolefins.

The fermentation methods may be performed in a suitable container or vessel, including but not limited to, a cell culture plate, a flask, or a fermentor. In certain embodiments, the fermentation is conducted in a closed system to trap monoterpenes in the gas phase. For example, the closed system may include a series of vessels connected to one another to trap off gas including monoterpenes in the vapor phase. For example, a first vessel may contain a culture medium comprising an aqueous medium and genetically modified microorganisms. A second vessel comprising an organic overlay may be connected in series with the first vessel to trap the volatile monoterpenes. In certain embodiments, one or more additional vessels may be connected to the first vessel in series and/or parallel to capture a gaseous composition comprising myrcene and other monoterpene co-products.

Furthermore, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al., in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any volume of fermentation, e.g., from lab scale (e.g., 10 ml to 20 L) to pilot scale (e.g., 20 L to 500 L) to industrial scale (e.g., 500 L to ≥500,000 L) fermentations.

Additional details related to culture conditions and fermentation methods suitable for certain embodiments can be found in U.S. Pat. Nos. 8,603,800, 7,659,097 and WO2007/139924, which are incorporated herein by reference in their entirety for all purposes.

6.7.2. Fermentation Compositions

In another aspect, provided herein are fermentation compositions comprising a genetically modified microbial host cell described herein, a culture medium, and monoterpenes produced from the genetically modified microbial host cell. In the fermentation compositions provided herein, the monoterpenes comprise myrcene as a major component and one or more co-products (which are concurrently produced with myrcene) as minor components. In certain embodiments, the monoterpenes in fermentation compositions comprise at least about 85% myrcene and less than about 15% monoterpene co-products (excluding geraniol), compared to the total amount of monoterpenes, based on relative area % of monoterpene peaks shown in a GC chromatogram of the monoterpenes. In certain embodiments, the fermentation composition comprises at least about 88% to about 93% myrcene, compared to the total amount of monoterpene products in the culture medium.

In certain embodiments, the fermentation compositions comprise a number of different co-products catalyzed by the myrcene synthase in vivo in genetically modified microbial host cells. For example, the fermentation composition can comprise 1, 2, 3, 4, 5, 6, 7, 8, 9, or 10 monoterpene co-products as minor components. In certain embodiments, the fermentation compositions comprise 4-terpineol as one of monoterpenes co-products concurrently produced with myrcene as shown in FIG. 3B. By contrast, other myrcene synthases, such as those obtained from *Quercus ilex* (QiMS), do not produce 4-terpineol. See, e.g., FIG. 3A. In certain embodiments, the present fermentation compositions further comprise γ-terpinene and α-terpinene, which are not produced by other myrcene synthases. See, e.g., FIG. 3A. In other embodiments, the minor co-products may further comprise sabinene, limonene, β-ocimene, and/or β-linalool. In yet other embodiments, the minor co-products may further comprise α-thujene, (E)-sabinene hydrate, and/or (Z)-sabinene hydrate. In particular embodiment, the fermentation composition comprises myrcene as a major component, and γ-terpinene, α-terpinene, sabinene, limonene, β-ocimene, β-linalool, and/or 4-terpineol as minor components. In particular embodiment, the fermentation comprises myrcene as a major component, and γ-terpinene, α-terpinene, sabinene, limonene, β-ocimene, β-linalool, α-thujene, (E)-sabinene hydrate, and (Z)-sabinene hydrate, and/or 4-terpineol as minor components.

In certain embodiments, each of monoterpene co-products is concurrently produced with myrcene at a level detectable by GC-FID or GC-MS but in a small amount relative to myrcene. In certain embodiments, each monoterpene co-product is present in the fermentation composition in an amount greater than 0.1% but less than about 5%, compared to the total amount of monoterpenes, based on relative area % of the monoterpenes in a GC-MS. In certain embodiments, a monoterpene co-product is present in the fermentation composition in an amount greater than 0.5% but less than 4%, compared to the total amount of monoterpenes, based on relative area % of the monoterpenes in the GC-MS chromatogram. In certain embodiments, a monoterpene co-product is present in the fermentation composition in an amount greater than 1% but less than 3%, compared to the total amount of monoterpenes, based on relative area % of the monoterpenes in the GC-MS chromatogram.

In particular embodiments, the fermentation composition comprises about 89.09% to about 92.01% myrcene, compared to the total amount of the monoterpenes, based on relative area % of the monoterpenes in the GC-MS chromatogram. In particular embodiments, the fermentation composition further comprises at least about 0.65% to 0.90% α-terpinene, compared to the total amount of the monoterpenes, based on relative area % of the monoterpenes in the GC-MS chromatogram. In particular embodiments, the fermentation composition further comprises at least about 1.00% to about 1.06% γ-terpinene, compared to the total amount of the monoterpenes, based on relative area % of the monoterpenes in the GC-MS chromatogram. In particular embodiments, the fermentation composition further comprises at least about 2.32% to about 2.42% 4-terpineol, compared to the total amount of monoterpenes, based on relative area % of the monoterpenes in the GC-MS chromatogram. In particular embodiments, the fermentation composition further comprises at least about 0.80% to about 0.98% sabinene, compared to the total amount of monoterpenes. In particular embodiments, the fermentation composition further comprises at least about 0.54% to about 1.01% limonene, compared to the total amount of the monoterpenes, based on relative area % of the monoterpenes in the GC-MS chromatogram. In particular embodiments, the fermentation composition further comprises about 0.91% to about 0.21% β-ocimene, compared to the total amount of the monoterpenes, based on relative area % of the monoterpenes in the GC-MS chromatogram. In particular embodiments, the fermentation composition further comprises about 0.76% to about 1.17% β-linalool. In particular embodiments, the fermentation composition further comprises about 0% to about 0.51% α-thujene, compared to the total amount of the monoterpenes, based on relative area % of the monoterpenes in the GC-MS chromatogram. In particular embodiments, the fermentation composition further comprises about 0.54% to about 1% (E)-sabinene hydrate, compared to the total amount of the monoterpenes, based on relative area % of the monoterpenes in the GC-MS chromatogram. In certain embodiments, the fermentation composition further comprises about 0.98% to about 1.13% (Z)-sabinene hydrate, based on relative area % of the monoterpenes in the GC-MS chromatogram.

A number of myrcene synthase variants derived from *Ocimum basilicum* exhibit a substantially similar monoterpene product profile as the wild-type myrcene synthase of *Ocimum basilicum* and retain the high myrcene production level. The *Ocimum basilicum* myrcene synthase and its variants are particularly useful in certain embodiments, because they are capable of producing myrcene in relatively high titer during fermentation of genetically modified microbial host cells. Furthermore, as discussed above, both wild-type *Ocimum basilicum* and its variants provided herein, when expressed in genetically modified microbial host cells, produce a unique monoterpene product profile, which is distinguishable from monoterpene product profiles produced by myrcene synthases derived from other organisms. For example, the presently described myrcene synthases, when expressed in genetically modified microbial host cells, produce one or more of α-terpinene and γ-terpinene as monoterpene co-products together with myrcene. By contrast, these co-products are not produced with myrcene by other myrcene synthases, such as *Quercus ilex* myrcene synthase. Therefore, the monoterpenes produced from the presently provided myrcene synthase sequences have a unique molecular fingerprint, which cannot be imparted by myrcene synthase sequences derived from other organisms.

In some embodiments, the myrcene is produced in an amount greater than about 1 gram per liter of fermentation medium. In some embodiments, the myrcene is produced in an amount greater than about 5 grams per liter of fermentation medium. In some embodiments, the myrcene is produced in an amount greater than about 10 grams per liter of the fermentation medium. In some such embodiments, the myrcene is produced in an amount from about 10 to about 200 grams or in an amount from about 10 to about 100 grams per liter of the fermentation medium. In some such embodiments, the myrcene is produced in an amount more than about 15 grams, more than about 20 grams, more than about 25 grams, or more than about 30 grams per liter of the fermentation medium.

In some embodiments, the myrcene is produced in an amount greater than about 1 milligrams per gram of dry cell weight. In some embodiments, the myrcene is produced in an amount greater than about 10 milligrams per gram of dry cell weight. In some embodiments, the myrcene is produced in an amount greater than about 50 milligrams per gram of dry cell weight. In some embodiments, the myrcene is produced in an amount greater than about 50 milligrams per gram of dry cell weight. In some such embodiments, the myrcene is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the myrcene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the myrcene produced by a microbial host cell that does not comprise a heterologous nucleic acid molecule encoding a myrcene synthase, on a per unit volume of cell culture basis.

In some embodiments, the myrcene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the myrcene produced by a microbial host cell that does not comprise a heterologous nucleic acid molecule encoding a myrcene synthase, on a per unit dry cell weight basis.

In some embodiments, the myrcene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the myrcene produced by a microbial host cell that does not comprise a heterologous nucleic acid molecule encoding a myrcene synthase, on a per unit volume of cell culture per unit time basis.

In some embodiments, the myrcene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the myrcene produced by a microbial host cell that does not comprise a heterologous nucleic acid molecule encoding a myrcene synthase, on a per unit dry cell weight per unit time basis.

6.7.3. Recovery of Myrcene

The monoterpenes including myrcene produced by the genetically modified microbial host cell described herein can be isolated from the fermentation compositions using any suitable separation and purification methods known in the art. In certain embodiments, monoterpenes are secreted into the culture medium and may spontaneously form a liquid organic phase, such as an emulsion phase, separate from an aqueous phase of the culture medium. In certain embodiments, secreted monoterpenes may partition into an organic overlay which is added to the culture medium. In certain embodiments, the secreted monoterpenes may evaporate from the culture medium and can be captured as a gas composition in the headspace of a vessel. In certain embodiments, monoterpenes can be recovered from cellular components of the genetically modified microbial host cells. The monoterpenes in various phases can be recovered using known techniques in the art. For example, production and recovery techniques are described in WO2007/139924, which is incorporated herein by reference in its entirety.

In some embodiments, a liquid organic phase comprising the myrcene may be separated from the fermentation medium by centrifugation. In other embodiments, a liquid organic phase comprising the myrcene separates from the fermentation spontaneously. In yet other embodiments, a liquid organic phase comprising the myrcene is separated from the fermentation by adding a deemulsifier and/or a nucleating agent into the fermentation reaction. Illustrative examples of deemulsifiers include flocculants and coagulants. Illustrative examples of nucleating agents include droplets of the myrcene itself and organic solvents such as dodecane, isopropyl myristate, methyl oleate, mineral oil, polyalphaolefins, and the like. In certain embodiment, the genetically modified microbial host cells can be cultured in a production medium with an organic phase overlay (e.g., 10% or 50% overlay of isopropyl myristrate) to facilitate recovery.

In some embodiments, the myrcene is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

Myrcenes produced by host cells can be recovered using any of a variety of methods including but not limited to chromatography, extraction, solvent extraction, membrane separation, electrodialysis, reverse osmosis, distillation, chemical derivatization, and crystallization.

Additional processing steps to improve myrcene quantification or isolation include but are not limited to breaking open the host cells. Suitable methods include but are not limited to vortexing, sonication, homogenization, and the use of glass beads. Other processing steps can include centrifugation to remove unwanted cell debris from the supernatant.

Myrcene production can be readily quantified using well-known methods known in the art including but are not limited to gas chromatography (GC), gas chromatography-mass spectrometry (GC/MS), nuclear magnetic resonance (NMR), RAMAN spectroscopy, optical absorption (UV/VIS), infrared spectroscopy (IR), high performance liquid chromatography (HPLC), liquid chromatography-mass spectrometry (LC/MS), ion chromatography-mass spectrometry, thin layer chromatography, pulsed amperometric detection, and UV-vis spectrometry.

In some embodiments, the myrcene is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of an myrcene refers to an myrcene that is free from other terpenes or contaminants.

7. EXAMPLES 7.1 Construction of Nucleic Acid Constructs and Plasmids

This example describes methods for making nucleic acid constructs and plasmids useful in the generation and characterization of myrcene synthase variants.

A high copy plasmid (2μ/leu2d plasmid) was used to express myrcene synthases from different organisms. The 2μ/leu2d plasmid is described in Erhart and Hollenberg, *J. Bacteriol.* 1983, 156(2): 625-635.

Plasmid pAM11613 was used for competition assays for tier I mutagenesis, and has a nucleotide sequence of SEQ ID NO: 33. Plasmid pAM11613 has the following as main elements in addition to the yeast vector backbone: pUC origin (bp 3218 to 2551); CYC1 terminator (bp 3595 to 3405); trichodiene synthase ("TDS"; bp 4729 to 3605); Gal1/10 promoter (bp 5403 to 4737); limonene synthase version A from *Citrus limon* ("LMSvA"; bp 5414 to 7096); ADH1 terminator (bp 7262 to 7098); and Leu2d (bp 8107 to 9198).

Plasmid pAM11614 was used for competition assays for combinatorial library of ObMS mutant, and has a nucleotide sequence of SEQ ID NO: 34. Plasmid pAM11614 has the following as main elements in addition to the yeast vector backbone: pUC origin (bp 2551 to 3218); CYC1 terminator (bp 3405 to 3595); trichodiene synthase ("TDS"; bp 3605 to 4729); Gal1/10 promoter (bp 4737 to 5403); limonene synthase version B from *Citrus limon* ("LMSvB"; bp 5414 to 7099); ADH1 terminator (bp 7101 to 7265); and Leu2d (bp 8110 to 9201).

Plasmid pAM2947 contains the F-Cphl gene operably linked to pTDH3 promoter, a kanmx4-marker, and the Cen-ARS. The nucleotide sequence of plasmid pAM2947 is shown as SEQ ID NO: 35.

7.2 Microbial Host Strains

This example describes methods for making yeast strains used in the generation and characterization of myrcene synthase variants.

Yeast strain Y13203, derived from a wild-type *Saccharomyces cerevisiae* strain (CEN.PK2), was used to express and screen myrcene synthases from various organisms. The strain overexpresses the mevalonate pathway genes by chromosomally integrating mevalonate pathway genes (acetyl-CoA thiolase, HMG-CoA synthase, HMG-CoA reductase, mevalonate kinase, phosphomevalonate kinase, mevalonate pyrophosphate decarboxylase, and IPP isomerase gene) from *S. cerevisiae* under the control of GAL promoters. Additional information about the chromosomal integration of the mevalonate pathway genes and IPP isomerase and their sequences can be found in U.S. Pat. Nos. 8,221,982 and 8,859,261, which are incorporated herein by reference in their entirety. The strain is also engineered to down regulate ERG20 gene expression by operably linking the ERG20 with promoter pCTR3 (Labbe and Thiele, *Methods of Enzymology*, vol. 306, pages 145-153).

Yeast strain Y21605 is derived from a wild-type *Saccharomyces cerevisiae* strain (CEN.PK2). This strain is derived from strain Y13203. The strain contains ObMS nucleic acid (SEQ ID NO: 3) operably linked to promoter Pgal1 and AgGPPS (SEQ ID NO: 8) operably linked to promoter Pgal10 on a 2μ/leu2d plasmid. The strain also comprises the chromosomally integrated mevalonate pathway genes (acetyl-CoA thiolase, HMG-CoA synthase, HMG-CoA reductase, mevalonate kinase, phosphomevalonate kinase, and mevalonate pyrophosphate decarboxylase, and IPP isomerase gene) from *S. cerevisiae* under the control of GAL promoters. The strain is also engineered to down regulate ERG20 gene expression by operably linking the ERG20 with promoter pCTR3.

Myrcene screening host strain Y21704 was used to screen GPPSs from various organisms. The strain is derived from strain Y13203 and further comprises a GB1 expression tagged ObMS nucleic acid sequence operably linked to promoter Pgal1 on a leu2d plasmid. The GB1 expression tag is described in Chen and Patel, Biochem. Biophys. Res. Comm. 317(2): 401-405 (2004).

Yeast strain Y10566 was used in a competition assay with plasmids pAM11613 and pAM11614. The strain is derived from a wild-type *Saccharomyces cerevisiae* strain (CEN.PK2). The strain comprises the nucleic acids described above for strain Y13203 and further comprises two copies of AgGPPS gene (SEQ ID NO: 8)).

Yeast strain X100 was used to express 1×ObMS, 5×ObMS, and 14×ObMS nucleic acids and to compare their myrcene titer. The strain is derived from a wild-type *Saccharomyces cerevisiae* strain (CEN.PK2). The strain comprises nucleic acids described above for Y13023 and further comprises two copies of SaGPPS (SEQ ID NO: 7) operably linked to pGAL1 promoter, ERG20 operably linked to pMAL1 promoter, and landing pads for myrcene synthase nucleic acids.

7.3 Cell Density Measurements

This example describes methods for determining the cell density of a microorganism culture.

The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to the density of a specific type of organism within a specific medium, but the specific relationship between OD and amount of microorganism per volume may not generally be applicable across all types of organisms in all types of media. A calibration curve can be created by measuring the OD and the dry cell weight over a range of cell densities. In some cases, these correlations can be used in different fermentation of the same or similar microorganisms in the same or similar media.

An exemplary method for determining the cell density ($OD_{600}$) of a yeast cell culture is as follows. An 8 μL sample of a cell culture is combined with 92 μL of Triton OD Diluent (20 g/L Triton X-114, 200 mL/L PEG 200, 200 mL/L 100% ethanol, rest water) in a clear 96-well plate, the solution is agitated at 1,000 RPM for 6 minutes, and the $OD_{600}$ was determined by measuring absorbance at 600 nm on an M5 spectrophotometer (Molecular Devices, Sunnyvale, Calif.).

7.4 GC Methods to Determine the Proportion of Myrcene in a Mixture of Monoterpenes and its Titer This example describes an exemplary gas chromatography (GC) based method useful for determining the area % product purity and myrcene titers of yeast cell cultures.

The area % product profile purity for samples containing myrcene were determined using an Agilent Gas Chromatograph with Flame Ionization Detection (GC-FID). The GC-FID method parameters are outlined in Table 1A. The area % product profile purity is a purity measure where the % purity is the area due to myrcene expressed as a percentage of the total monoterpenes area, and is a measure of the purity of the product profile of a particular enzyme.

TABLE 1A

The GC-FID parameters used to obtain the area % product profile purity of myrcene in samples.

| Oven | |
|---|---|
| Initial Temp, (° C.) | 40.0 |
| Initial Hold, (min) | 8.0 |
| Rate 1, (° C./min) | 5.0 |
| Temp 1, (° C.) | 150.0 |
| Final Time 1, (min) | 30.0 |
| Rate 2, (° C./min) | 50.0 |

TABLE 1A-continued

The GC-FID parameters used to obtain the area % product profile purity of myrcene in samples.

Oven

| | |
|---|---|
| Final Temp, (° C.) | 320 |
| Final Time 2, (min) | 31.4 |
| Rate 3, (° C./min) | 0.0 |
| Final Temp, (° C.) | 320 |
| Final Time 3, (min) | 36.4 |
| Rate 4, (° C./min) | OFF |
| Runtime, (min) | 36.4 |
| Column | Agilent HP-1 |
| Dimensions | 50 m × 0.20 mm, 0.11 μm film |

The monoterpene (C10) retention time window on the GC-FID chromatogram is defined as between 10.0 and 23.0 minutes. No monoterpenes were shown to elute earlier than 10.0 minutes and later than 23 minutes as determined by testing terpene standards and by GC-MS analysis of synthase products (presence of molecular ion 136). In addition, unknown peaks observed in the analyzed samples were excluded as non-terpenes if they were detected in the negative control. The negative control was a strain that had a nonfunctional myrcene synthase.

For determining myrcene titer, GC-FID with an LTM column was used with an external standard calibration. The GC-FID parameters used to measure myrcene amounts are outlined in Table 1B. The external standard calibration was prepared on a weight by volume basis. A known amount of myrcene was diluted in ethyl acetate, and serial dilutions of 10-200 mg/L were prepared and used to calibrate the instrument.

TABLE 1B

The GC-FID parameters used to obtain the myrcene amounts

| Oven | Mach, LTM |
|---|---|
| Initial Temp, (° C.) | 80 |
| Initial Hold, (min) | 0.15 |
| Rate 1, (° C./min) | 15 |
| Temp 1, (° C.) | 120 |
| Hold Time 1, (min) | 0 |
| Rate 2, (° C./min) | 300 |
| Final Temp, (° C.) | 320 |
| Hold Time 2, (min) | 3.0 |
| Final Time, (min) | 6.48 |
| Runtime, (min) | 6.48 |
| Column | Agilent, Agilent DB-1MS-LTM |
| Dimensions | 10 m × 0.10 mm, 0.10 μm film |

7.5 Headspace Analysis to Determine Myrcene Titer

This example describes an exemplary method useful for quantification of myrcene in the gas phase in the well headspace of a plate.

For a competition assay where a myrcene synthase variant sequence and a control enzyme, (R)-limonene synthase, sequence were cloned on the same plasmid, both myrcene and limonene were quantified via the headspace analysis. Strains were grown in sealed 2.2 ml 96-well plates, after which volatile myrcene and limonene present in the well headspace were analyzed by Headspace Gas Chromatography/Flame Ionization Detection (GC/FID). GC/FID system is composed of Agilent 7890 gas chromatograph with FID detector and a Gerstel MPS autosampler. One hundred microliter of the headspace gas was injected into GC, and samples were separated through Agilent HP-5 P/N 1909J413 column (7 m×0.200 mm, 0.33 μm film) using hydrogen as the carrier gas. The temperature of GC oven was set to 55° C. For quantification of myrcene, calibration standards with known concentrations of myrcene and/or limonene in IPM overlay were prepared, filled to 2.2 ml plates, sealed, and ran in parallel with the samples.

7.6 Screening Wild-Type Myrcene Synthase Genes from Various Species

This example describes screening wild-type myrcene synthase genes from several different species to select a myrcene synthase gene suitable for expression in yeast cells.

A number of myrcene synthase genes from different organisms that were either biochemically characterized in the literature or putatively annotated as myrcene synthases were selected for screening for suitable myrcene synthase genes for heterologous expression in yeast host cells. As shown in Table 2 below, these genes include those obtained from *Picea abies* (Martin et al. (2004) *Plant Physiol.* 135, 1908-1927); *Abies grandis* (Bohlmann et al. (1997) JBC 272, 21784); *Ocimum basilicum* (Irijima et al. (2004) *Plant physiol.* 136, 3724-3736); *Quercus ilex* (Fischbach et al. (2001) *Eur. J. Biochem.* 268, 5633-5638); *Antirrhinum majus* (Dudareva et al. (2003) *Plant Cell* 15, 1227-124); *Alstroemeria peruviana* (Aros et al. (2012) *J. Exp. Botany* 63, 2739-2752); and *Medicago truncatula*. The nucleotide sequences are also available from NCBI GenBank.

For each gene, two different codon optimized sequences were designed according to standard protocol using software provided by Integrated DNA Technologies (Coralville, Iowa), http://www.idtdna.com/CodonOpt, selecting *Saccharomyces cerevisiae* as the codon organism. Two examples of codon optimized sequences are shown as SEQ ID NO: 3 (*Ocimum basilicum* myrcene synthase) and SEQ ID NO: 36 (*Quercus ilex* myrcene synthase). The testing was carried out in *Saccharomyces cerevisiae* strain Y13203 with both myrcene synthase nucleic acid and AgGPPS nucleic acid (SEQ ID: 6; codon optimized) expressed on a high copy plasmid 2μ/leu2d.

Strains comprising different myrcene synthase genes were picked from colonies on an agar plate into 2 ml of 2% sucrose Bird Seed Media (BSM, originally described by van Hoek et al., *Biotechnology and Bioengineering* 68(5), 2000, pp. 517-523) in a falcon tube and incubated at 30° C. for 24 hours with shaking. Strain variants were then subcultured to 0.08 $OD_{600}$ in 10 ml of 4% galactose BSM, 125 μM $CuSO_4$ in a 125 ml baffled flask with 10 ml isopropyl myristate (IPM) as an overlay. Samples were taken at 24 hour, 48 hour, or 72 hour as needed. Myrcene titer was determined by diluting 100 μl of IPM taken from the sample at desired time points into 900 μl of ethyl acetate in a glass GC vial. Samples were vortexed, and were analyzed by gas chromatography (GC) as described in Example 7.4. The cell density was determined at $OD_{600}$ by diluting 100 μl of broth into 900 μl of sterile water in a cuvette. Cuvettes were vortexed and the cell density at $OD_{600}$ was assayed using a spectrophotometer.

TABLE 2

The myrcene production from various strains comprising different myrcene synthase genes is shown below:

| Organism (common name) | Enzyme name | Myrcene production in 72 h | Myrcene purity | Uniprot | SEQ ID NOS. |
|---|---|---|---|---|---|
| *Ocimum basilicum* (Basil) | ObMS | ~1 g/L | 89% | Q5SBP1 | SEQ ID NO: 3 |
| *Quercus ilex* (Holly oak) | QiMS | 200 mg/L | 91% | Q93X23 | SEQ ID NO: 36 |
| *Picea abies* (Norway spruce) | PaMS | 50 mg/L | 89% | Q675K9 | |
| *Abies grandis* (Grand fir) | AgMS | No myrcene | Inactive | Q24474 | |
| *Aegilops squarrosa* (Goatgrass) | AsMS | No myrcene | Inactive | M8AXZ3 | |
| *Alstroemeria peruviana* (Peruvian lily) | ApMS | 15 mg/L | Low activity | I3IRM3 | |
| *Antirrhinum majus* (Snapdragon) | AmMS | 13 mg/L | Low activity | Q84ND0 | |
| *Medicago truncatula* (Barrel clover) | MtMS1 | No myrcene | Likely not a MS | A0RZI3 | |
| *Medicago truncatula* (Barrel clover) | MtMS2 | No myrcene | Likely not a MS | G7IRJ6 | |

As summarized in Table 2, the notable myrcene synthases are ObMS (~1 g/L), QiMS (200 mg/L), and PaMS (50 mg/L), from which myrcene production was observed. Other myrcene synthases shown in Table 2 produced either inactive or low activity myrcene synthase. Two of them (MtMS1 and MtMS2) produced no myrcene, indicating that they are likely not a myrcene synthase. When the ObMS amino acid sequence was aligned with other myrcene synthase sequences in Table 2, the ObMS amino acid sequence shares less than 50% identity with other myrcene synthase amino acid sequences (analysis according to Clone Manager Suite, method: FastScan–Max Qual (Cons N).

Monoterpenes produced from the host strains expressing ObMS, QiMS, and PaMS were analyzed using GC-MS and GC-FID analysis as described in Example 7.4. The results show that QiMS and PaMS appear to produce an equal or higher proportion of myrcene in the mixture of monoterpenes (i.e., myrcene purity profiles) than ObMS. However, as shown in Table 2, ObMS expressed in genetically modified microbial host cells generated at least five fold higher myrcene production after 72 hours of culture compared to another myrcene producer (i.e., QiMS). It is noted that a low level of geraniol was observed but was not included as an impurity in the calculation of myrcene purity because it was likely generated from myrcene synthase-independent hydrolysis of GPP in yeast.

FIG. 3A shows a comparison of GC-FID traces of myrcene and other co-products produced by yeast host cells comprising ObMS (trace in the middle) and QiMS (trace at the bottom). As shown by the differences in the two traces, each myrcene synthase exhibits a distinct product profile. In particular, the ObMS trace indicates that the monoterpenes produced from genetically modified microbial host cells expressing ObMS include α-terpinene, γ-terpinene and 4-terpineol, which are not present in the monoterpenes produced from yeast cells expressing QiMS. A number of samples comprising yeast host cells comprising other myrcene synthases were analyzed by GC-FID. Similar to QiMS, other myrcene synthases did not produce α-terpinene, γ-terpinene, 4-terpineol, or other monoterpene co-products.

7.7 Monoterpene Product Profile Produced from *Ocimum basilicum* Myrcene Synthase In this example, the monoterpene product profile of ObMS determined from a GC-MS analysis is described in detail.

Y21605 strain comprising the ObMS nucleic acid (SEQ ID NO: 3) was grown for 2 days pre-culture in a falcon tube containing 2 ml of BSM 2% sucrose medium and incubated at 30° C. with shaking. For production, the strain was grown for 96 hours at 30° C. in a 125 ml unbaffled shake flask containing 10 ml BSM 4% galactose and 125 μM $CuSO_4$ with 10 ml of IPM as an overlay. 1 ml of IPM was sampled from the overlay and spun down to pellet any biomass present. A 500 μl of clarified IPM was diluted twice in 500 μl of ethyl acetate in a GC vial and was analyzed by GC-MS analysis using Agilent 7890 gas chromatograph with mass spectrometer.

The sample was analyzed using GC-MS as follows. HP-1, 50 m×0.2 mm×0.11 um column was used for myrcene analysis. Briefly, 1 μl or 3 μl of sample at about 0.5 g/L was injected on the column and the following temperature gradient was applied: 40° C. with hold for 8 minutes; ramp at 5° C./min to 150° C.; followed by a ramp at 120° C. to 320° C. with hold for 5 minutes to bake out the column. Helium is used as a carrier gas with constant flow at 1.5 ml/min. Inlet is set to 250° C. with the 10:1 split ratio. MS Source is set to 230° C. and MS quad to 15° C. Solvent delay was set to 4 min, EMV Mode to Gain Factor with Gain Factor to 15.

Data was analyzed by NIST 2009 and Wiley 9th Edition Libraries using both Kovats Retention Index (KI) and compound MS trace, with proposed assignments given in Table 3. KI is relative retention value based on a scale defined by the elution of a series of n-alkanes and calculated using the following equations:

For temperature programmed chromatography, the Kovats index is given by the equation $$I = 100 \times \left[ n + (N - n) \frac{t_{r(unknown)} - t_{r(n)}}{t_{r(N)} - t_{r(n)}} \right]$$

Where:

$I$ = Kovats retention index, $n$ = the number of carbon atoms in the smaller $n$-alkane, $N$ = the number of carbon atoms in the larger $n$-alkane, $t_r$ = the retention time.

Available authentic standards of compounds tentatively identified by library match were analyzed for definitive conformation of peak assignment, as summarized in Table 3. See also, FIG. 4 for molecular structures of compounds associated with peak assignments.

TABLE 3

Table 3 illustrates calculation of KI index for selected peaks with MW 136 (C10 terpene) and 154 (C10 terpene alcohol). Matching compounds are selected from NIST library based on fragmentation pattern and KI.

| peak RT [min.] | n | N | tr unknown | tr n | tr N | KI calculated | KI database | Library match |
| --- | --- | --- | --- | --- | --- | --- | --- | --- |
| 12.544 | 9 | 10 | 12.544 | 11.53 | 15.903 | 923.2 | 928-929 | α-Thujene? |
| 14.327 | 9 | 10 | 14.327 | 11.53 | 15.903 | 964.0 | 964-975 | Sabinene |
| 15.315 | 9 | 10 | 15.315 | 11.53 | 15.903 | 986.6 | 979-981 | Myrcene |
| 16.101 | 10 | 11 | 16.101 | 15.903 | 19.562 | 1005.4 | 1008-1017 | α-Terpinene |
| 16.56 | 10 | 11 | 16.56 | 15.903 | 19.562 | 1018.0 | 1020 | (+)-Limonene |
| 17.375 | 10 | 11 | 17.375 | 15.903 | 19.562 | 1040.2 | 1032-1041 | β-Ocimene |
| 17.647 | 10 | 11 | 17.647 | 15.903 | 19.562 | 1047.7 | 1047-1053 | γ-Terpinene |
| 17.729 | 10 | 11 | 17.729 | 15.903 | 19.562 | 1049.9 | 1050 | (E)-sabinene hydrate? |
| 18.759 | 10 | 11 | 18.759 | 15.903 | 19.562 | 1078.1 | 1068-1090 | (Z)-sabinene hydrate? |
| 19 | 10 | 11 | 19 | 15.903 | 19.562 | 1084.6 | 1081-1082 | β-Linalool |
| 21.338 | 11 | 12 | 21.338 | 19.562 | 22.74 | 1155.9 | 1160-1175 | (−)-4-Terpineol |

"?" stands for tentative assignment due to low library score.

TABLE 4

Table 4 shows KI values for tested standards and corresponding values for peaks detected in the analyzed sample. Standards for testing were selected based on results from Table 3.

| Standard name | RT of standard [min.] | KI of standard | KI of unknown in sample |
| --- | --- | --- | --- |
| Sabinene | 14.284 | 963 | 964 |
| Myrcene | 15.215 | 987 | 987 |
| α-Terpinene | 16.069 | 1005 | 1005 |
| Limonene | 16.534 | 1018 | 1018 |
| β-Ocimene | 17.359 | 1040 | 1040 |
| γ-Terpinene | 17.63 | 1048 | 1048 |
| β-Linalool | 18.987 | 1085 | 1085 |
| 4-terpineol | 21.319 | 1156 | 1156 |

TABLE 5

Table 5 illustrates area % purity for analyzed myrcene sample (i.e., relative monoterpenes in a sample composition based on area %) injected at 3 μl and 1 μl. For area % calculation, area of all peaks with MW 136 (C10 terpene) and 154 (C10 terpene alcohol) were added to 100% (assuming the same signal response for all compounds). Peaks with area % less than 0.5% were rejected and area % was re-calculated for remaining compounds.

| Compound name | RT | Area %, 3 μl injection | Area %, 1 μl injection |
| --- | --- | --- | --- |
| α-Thujene (tentative) | 12.544 | 0.51 | NA |
| Sabinene | 14.327 | 0.98 | 0.80 |
| Myrcene | 15.315 | 89.09 | 92.01 |
| α-Terpinene | 16.101 | 0.90 | 0.67 |
| Limonene | 16.56 | 1.01 | 0.54 |
| β-Ocimene | 17.375 | 1.21 | 0.91 |
| γ-Terpinene | 17.647 | 1.06 | 1.00 |
| (E)-sabinene hydrate (tentative) | 17.729 | 0.54 | NA |
| (Z)-sabinene hydrate (tentative) | 18.759 | 1.13 | 0.98 |
| β-Linalool | 19.000 | 1.17 | 0.76 |
| 4-terpineol | 21.338 | 2.42 | 2.32 |

A GC-MS analysis of an ObMS myrcene sample extracted from the broth of Y21605 revealed six other C10 terpenes and four C10 terpene alcohols as minor components in addition to myrcene. See FIG. 3B. The main impurity among the minor co-products is 4-terpineol which is present at about 2.3%. In FIG. 3B, peak 1 represents thujene; peak 2 represents sabinene; peak 3 represents myrcene; peak 4 represents α-terpinene; peak 5 represents limonene; peak 6 represents ocimene; peak 7 represents γ-terpinene; peak 8 represents (E)-sabinene hydrate; peak 9 represents (Z)-sabinene hydrate; peak 10 represents (3-linalool; and peak 11 represents 4-terpineol. The molecular structures of all ten co-products are shown in FIG. 4. The relative area % for each co-product was measured at two different injection volumes of the sample, with the higher injection giving higher impurity levels (Table 5). The myrcene purity was again measured at 89-92% based on the peak areas, consistent with the previous result. GC-MS analyses of other samples derived from host cells genetically modified with myrcene synthase variants described in Examples 7.9 to 7.11 below exhibited substantially similar myrcene purity levels and other co-product peaks as shown in FIG. 3B (data not shown).

7.8 Screening Wild-Type Geranyl Pyrophosphate Synthase Genes from Various Organisms for Co-Expression with a Myrcene Synthase This example describes screening wild-type geranyl pyrophosphate synthase genes from various organisms to select for a geranyl pyrophosphate gene suitable for co-expression with a myrcene synthase in yeast host cells.

Several GPPSs, including both homodimeric and heterodimeric enzymes, were selected for screening. See Table 6 below. For each gene, two different codon optimized sequences were designed according to standard protocol using software provided by Integrated DNA Technologies (Coralville, Iowa) at http://www.idtdna.com/CodonOpt, selecting *Saccharomyces cerevisiae* as the codon organism. For initial testing, each sequence was cloned via single-copy integration into yeast strain Y13203 with ObMS expressed on a high copy plasmid 2μ/leu2d. Myrcene production (as measured by GC) in these strains is dependent on the activity of GPPS—a more active GPPS diverts more carbon from sugar to higher level of GPP for ObMS, leading to higher myrcene titers. Several strains were also constructed with (R)-limonene synthase (ClLMS from *Citrus limon*), an enzyme with higher activity in yeast than ObMS, in place of ObMS, and limonene production was compared with myrcene to help diagnose whether a myrcene synthase is limiting.

The previous experiments with AgGPPS showed that one copy of AgGPPS was not sufficient to support normal strain growth and only supported low level of myrcene production (data not shown). It was therefore unclear prior to the screening whether integrating a single copy of GPPS would provide sufficient activity for the purpose of this screening. However, the single-copy integration approach could potentially allow identification of the most active GPPSs faster and more definitively than a plasmid-based approach where weaker GPPSs are compensated by higher copy numbers. Indeed, although AgGPPS containing strain did not grow very well and produced a relatively low amount of myrcene, it was found that a homodimeric bacterial GPPS, *Streptomyces aculeolatus*, was able to support robust strain growth as shown in Table 6.

TABLE 6

Summary of GPPSs screening results. Activity is defined as amount of strain growth in plates with GPPS integrated as a single copy.

| Organism (common name) | Enzyme Name | Gene Accession Nos. (Notes) | Activity (with a single copy) |
| --- | --- | --- | --- |
| *Abies grandis* (Grand fir) | AgGPPS | AF513112.1 | Low |
| *Streptomyces aculeolatus* | SaGPPS | ABS50454 (Biochemically verified to be a GPPS) | High |
| *Ips pini* (bark beetle) | IpGPPS | AY953508 (GPPS and MS bifunctional enzyme; low activity as GPPS) | Low |
| *Catharanthus roseus* (Madagascar periwinkle) | CrGPPS | JX417185 | No |
| *Humulus lupulus* (European hop) | HlGPPS | ACQ90682/ACQ90681 (Heterodimer) | No |
| *Glycine max* (Soybean) | GmGPPS | ABY90133 | No |
| *Mangifera indica* (Mango) | GPPS1 | AFJ52721 | No |
| *Mangifera indica* (Mango) | GPPS2 | AFJ52722 | No |
| *Medicago sativa* (Alfalfa) | MsGPPS | AEL29573 | No |
| *Phalaenopsis bellina* (Orchid) | PbGPPS | ABV71395 | No |
| *Picea abies* (Norway spruce) | PolDS1 | GQ369788 | No |
| *Salvia miltiorrhiza* (Chinese sage) | GPPS | AEZ55677 | No |
| *Vitis vinifera* (Grape) | VvGPPS | AAR08151 | No |

The myrcene production was also measured in strain Y21704. Myrcene screening host strain Y21704 containing a Pgal1 driven ObMS on a leu2d plasmid was unable to reach maximum $OD_{600}$ in culturing conditions when induced on galactose with 125 μM $CuSO_4$ in the absence of a functional GPPS. As such, nonfunctional GPPS variants were determined by lack of growth of their host strain in a 96 well plate model. Strain variants, each comprising a GPPS gene from different organisms, were picked from single colonies on an agar plate into a 96 well plate containing 360 μl of 2% sucrose BSM and incubated for 24 hours at 30° C. with shaking. For production, 6 μl of each well was then subcultured into a new 96 well plate containing 360 μl of 4% galactose BSM and incubated for 72 hours at 30° C. with shaking. $OD_{600}$ measurement samples were taken at 72 hours, and functional GPPS variants determined by positive growth. This subset of functional GPPS variants integrated into Y21704 was tested for myrcene production in 125 ml baffled shake flasks as described above in Example 7.6. The samples were analyzed using the GC analysis method described in Example 7.4.

FIG. 5 illustrates the comparison of myrcene production by two GPPSs—SaGPPS and AgGPPS. The codon optimized nucleotide sequence for SaGPPS is shown as SEQ ID NO: 6. The codon optimized nucleic acid sequence for AgGPPS is shown as SEQ ID NO: 8. As shown in FIG. 5, the bacterial GPPS derived from *Streptomyces aculeolatus* supported at least three fold increase in myrcene production compared to the AgGPPS derived from plant species. Thus, the bacterial SaGPPS was selected as a GPPS for co-expression with ObMS in other experiments.

7.9 Generation of Myrcene Synthase Variants—Tier I Mutagenesis

This example describes methods for generating libraries of myrcene synthase variants and a competition assay to rank improvement in myrcene synthase activity for each variant over the parent sequence.

In a competition assay, each variant sequence is cloned into plasmid pAM11613. A control enzyme, (R)-limonene synthase from *Citrus limon* (CILSvA), is also expressed on the same plasmid as a test myrcene synthase variant, and the two synthases compete in a microbial host cell for the same substrate (GPP) for the production of myrcene and limonene, respectively. Strains containing the competition plasmid co-produces myrcene and limonene, and the ratios of myrcene and limonene for different myrcene synthase variants are used as the readout for the relative activity of these enzymes. The myrcene synthase variants are identified when they outperform their parent in competing against a limonene synthase for converting GPP to myrcene as opposed to limonene (i.e., higher myrcene to limonene ratios than that of its parent).

To design a mutagenesis library, an alignment of protein sequences of ObMS and several other terpene synthases were created. The residues found to generate beneficial mutations from those terpene synthases, "hot spots," as well as the proposed active site residues were overlaid onto the alignment. Potential hot spots for ObMS were predicted and ranked in order of importance based on the conservation of the region or the residues, the sizes of hits previously identified, and the number of synthases that the residue was found to be beneficial. A total of 47 hot spots were selected.

A saturation mutagenesis library at each of the 47 amino acid positions using a NDT degenerate codon was constructed, leading to 12 possible amino acid changes at the positions. Site-directed mutagenesis library was created by polymerase chain reaction (PCR) mutagenesis using the wild-type myrcene synthase sequence encoding ObMS as template. Mutations were introduced using degenerate NDT codon to convert the residue at the identified position from its wild-type amino acid sequence to a mixed population of 12 possible amino acid sequences (Phe, Leu, Ile, Val, Tyr, His, Asn, Asp, Cys, Arg, Ser, Gly). Internal degenerate primers used to introduce mutations to residue positions 213, 381, 389, 404, 439, 484, 482, 528 and 543, as well as flanking primer sequences are listed in Table 7.

TABLE 7

The forward and reverse primers used to introduce mutations into the ObMS are shown below. The first column indicates the amino acid positions of SEQ ID NO: 2 (ObMS amino acid sequence) and forward or reverse primers, the second column indicates the sequence ID numbers, and the third column shows the nucleotide sequences of the primers.

| aa positions | SEQ ID NO. | Sequence |
|---|---|---|
| 213-IF | SEQ ID NO: 9 | TGGTTCTTAGATGCTTATGCTAGCAGACC |
| 213-IR | SEQ ID NO: 10 | GGTCTGCTAGCATAAGCATCTAAGAACCAAHNGGCCTCCAGCCTTTGA ATCCG |
| 381-IF | SEQ ID NO: 11 | CGTGGCTGGATTTGGTTGAAGCATATNDTGTTGAGGCAAAGTGGTTCC ACGAT |
| 381-IR | SEQ ID NO: 12 | ATATGCTTCAACCAAATCCAGCCACG |
| 389-IF | SEQ ID NO: 13 | TATTTTGTTGAGGCAAAGTGGTTCCACNDTGGATATACTCCAACTCTAG AAGAATATCTC |
| 389-IR | SEQ ID NO: 14 | GTGGAACCACTTTGCCTCAACAAAATATGC |
| 404-IF | SEQ ID NO: 15 | CTAGAAGAATATCTCAACAATTCGAAGNDTACAATAATTTGTCCTGCAA TAGTCTCAGAA |
| 404-IR | SEQ ID NO: 16 | CTTCGAATTGTTGAGATATTCTTCTAGAGT |
| 439-IF | SEQ ID NO: 17 | GAGAGCATATACAAATATCATGACATCCTTNDTCTTTCCGGAATGCTTG CAAGGCT |
| 439-IR | SEQ ID NO: 18 | AAGGATGTCATGATATTTGTATATGCTCTC |
| 528-IF | SEQ ID NO: 19 | CTCGGAAGAGTGGCTAATTTTGTGTATGTGNDTGGAGATGGTTTTGGA GTGCAACACTC |
| 528-IR | SEQ ID NO: 20 | CACATACACAAAATTAGCCACTCTTCCGAG |
| 543-IF | SEQ ID NO: 21 | GTGCAACACTCAAAAATACATCAACAANDTGCTGAATTACTGTTTTACC CATATCAGTAA |
| 543-IR | SEQ ID NO: 22 | TTGTTGATGTATTTTTGAGTGTTGCACTCC |
| 482-IF | SEQ ID NO: 23 | ACGCCTCAGAGGAGGAGGCANDTGAGCACATCAGATTTCTTATGCGG GAG |
| 482-IR | SEQ ID NO: 24 | TGCCTCCTCCTCTGAGGCGT |
| 484-IF | SEQ ID NO: 55 | CTCAGAGGAGGAGGCACGTGAGNDTATCAGATTTCTTATGCGGGAGG CGT |
| 484-IR | SEQ ID NO: 56 | CTCACGTGCCTCCTCCTCTGAG |
| 552-IF | SEQ ID NO: 25 | AAATGGCTGAATTATTGTTTTACCCATACNDTTAAGCTAGCTAAGATCC GCTCTAACCGA |
| 552-IR | SEQ ID NO: 26 | GTATGGGTAAAACAATAATTCAGCCATTTG |
| 544-IF | SEQ ID NO: 27 | TTCGGTGTCCAACACTCTAAGATTCACNDTCAAATGGCTGAATTATTGT TTTACCCATAC |
| 544-IR | SEQ ID NO: 28 | GTGAATCTTAGAGTGTTGGACACCGAAACC |
| AM-405 | SEQ ID NO: 37 | CGTCAAGGAGAAAAAACCCCGGATCCATGGTTGAACCCCGACGC |
| AM-168 | SEQ ID NO: 38 | GCAAGGTTTTCAGTATAATGTTAC |
| 27-IF | SEQ ID NO: 57 | TCCAAGGAAGAACGTCATTTGGAAAGAAAG |
| 27-IR | SEQ ID NO: 58 | TCTTTCCAAATGACGTTCTTCCTTGGAAHNGTTGTTGTTCAAGGATTGA ATGTAATTAAA |
| 28-IF | SEQ ID NO: 59 | AAGGAAGAACGTCATTTGGAAAGAAAGGCT |
| 28-1R | SEQ ID NO: 60 | CTTTCTTTCCAAATGACGTTCTTCCTTAHNATGGTTGTTGTTCAAGGATT GAATGTAATT |

TABLE 7-continued

The forward and reverse primers used to introduce mutations into the ObMS are shown below. The first column indicates the amino acid positions of SEQ ID NO: 2 (ObMS amino acid sequence) and forward or reverse primers, the second column indicates the sequence ID numbers, and the third column shows the nucleotide sequences of the primers.

| aa positions | SEQ ID NO. | Sequence |
|---|---|---|
| 207-IF | SEQ ID NO: 61 | CAAAGATTGGAGGCCAAATGGTTCTTGG |
| 207-IR | SEQ ID NO: 62 | CAAGAACCATTTGGCCTCCAATCTTTGAHNTCTCCAATGCAAAGGTAACTCCAAAGAGTG |
| 222-IF | SEQ ID NO: 63 | CCAGATATGAACCCAATTATTTTCGAATTG |
| 222-IR | SEQ ID NO: 64 | CAATTCGAAAATAATTGGGTTCATATCTGGAHNAGAGGCGTAGGCATCCAAGAACC |
| 342-IF | SEQ ID NO: 65 | AACCAATTGCCATCTTACATGCAATTGNDTTATTTGGCCATTTATAACTTCGTCTCCGAA |
| 342-IR | SEQ ID NO: 66 | CAATTGCATGTAAGATGGCAATTGGTTGAT |
| 347-IF | SEQ ID NO: 67 | TCTTACATGCAATTGTGCTATTTGGCCATTNDTAACTTCGTCTCCGAATTGGCTTACGA |
| 347-IR | SEQ ID NO: 68 | AATGGCCAAATAGCACAATTGCATGTAAGA |
| 382-IF | SEQ ID NO: 69 | TCTTGGTTGGATTTGGTTGAAGCTTATTTCNDTGAAGCCAAGTGGTTCCACGACG |
| 382-IR | SEQ ID NO: 70 | GAAATAAGCTTCAACCAAATCCAACCAAGA |
| 390-IF | SEQ ID NO: 71 | TTGAAGCCAAGTGGTTCCACGACNDTTACACTCCAACTTTGGAAGAATACTTGAAC |
| 390-IR | SEQ ID NO: 72 | GTCGTGGAACCACTTGGCTTCAA |
| 401-IF | SEQ ID NO: 73 | ACTCCAACTTTGGAAGAATACTTGAACNDTTCTAAGATTACTATCATTTGTCCAGCCATC |
| 401-IR | SEQ ID NO: 74 | GTTCAAGTATTCTTCCAAAGTTGGAGTGTA |
| 428-IF | SEQ ID NO: 75 | TTTGCCAACTCTATCGATAAGACTGAANDTGAATCCATTTACAAGTATCACGACATTTTG |
| 428-IR | SEQ ID NO: 76 | TTCAGTCTTATCGATAGAGTTGGCAAAAGC |
| 466-IF | SEQ ID NO: 77 | GATGAAGCGTGGTGACGTTGCTAAGNDTATTCAATGTTACATGAAGGAACACAACGCC |
| 466-IR | SEQ ID NO: 78 | CTTAGCAACGTCACCACGCTTCATC |
| 505-IF | SEQ ID NO: 79 | CTGCCGCTGCTGCCGATGACNDTCCATTTGAATCTGACTTGGTTGTTGGTGC |
| 505-IR | SEQ ID NO: 80 | GTCATCGGCAGCAGCGGCAG |
| 514-IF | SEQ ID NO: 81 | GACTGTCCATTTGAATCTGACTTGGTTGTTNDTGCTGCCTCCTTGGGTAGAGTC |
| 514-IR | SEQ ID NO: 82 | AACAACCAAGTCAGATTCAAATGGACAGTC |
| 517-IF | SEQ ID NO: 83 | CTGACTTGGTTGTTGGTGCTGCCNDTTTGGGTAGAGTCGCTAACTTCGTCTAC |
| 517-IR | SEQ ID NO: 84 | GGCAGCACCAACAACCAAGTCAG |
| 524-IF | SEQ ID NO: 85 | GCCTCCTTGGGTAGAGTCGCTAACNDTGTCTACGTTGAGGGTGATGGTTTC |
| 524-IR | SEQ ID NO: 86 | GTTAGCGACTCTACCCAAGGAGGC |
| 527-IF | SEQ ID NO: 87 | CTTGGGTAGAGTCGCTAACTTCGTCTACNDTGAGGGTGATGGTTTCGGTGTC |
| 527-IR | SEQ ID NO: 88 | GTAGACGAAGTTAGCGACTCTACCCAAG |

To introduce mutations at the identified position, two PCR reactions were performed with the 5' external forward primer (AM-405) and internal reverse primers (IR), and internal forward primers (IF) and the 3' external reverse primer (AM-168), respectively, creating two overlapping fragments of the myrcene synthase sequence. The primer sequences are shown in Table 7. All PCR reactions were performed with Phusion® High-Fidelity DNA Polymerase according to manufacturer's manual.

To create the mutagenesis library in yeast, plasmid pAM11613 was digested with BamHI and NheI, and the digested vector backbone was purified. One microliter of each PCR fragment was mixed with 15 ng of digested pAM11613, and gap repaired into yeast strain Y10566. Twelve random clones from selected transformations were sequenced to confirm that the library contained an appropriate diversity and frequency of mutations at the desired residue position.

To screen for improved myrcene synthase activity, 36 yeast clones for each residue position were inoculated into wells of a 96-well plate in 360 μl of the preculture media (Bird Seed Medium containing sucrose 14 g/L, maltose 7 g/L, and lysine 1 g/L), and grown at 30° C. for two days by shaking at 1000 rpm. Then 3 μl of culture was subcultured into 2.2 ml 96-well deep well plates containing 75 μl of production media (Bird Seed Medium containing galactose 4% and 125 μM CuSO$_4$). The plates were then foil sealed with a heat sealer (e.g., PlateLoc Thermal Microplate Sealer, Agilent Technologies) and grown at 30° C. for three days by shaking at 1000 rpm.

The GC headspace assay described in Example 7.5 was used to quantify myrcene produced in the sealed plates at the end of growth and production. Headspace gas of the wells was injected directly into GC, and the peak areas of myrcene (produced by myrcene synthase mutants) and limonene (produced by limonene synthase present in vector pAM11613) were quantified. The ratio of myrcene peak area to limonene peak area was calculated for each yeast clone in the plates, and compared to that of the yeast clone expressing the wild-type myrcene synthase having the sequence of SEQ ID NO: 2. The yeast clone with an increased myrcene/limonene ratio was identified, and its myrcene synthase sequence was amplified and sequenced.

A total of nineteen beneficial mutations identified from screening the saturation mutagenesis library of 1xObMS were ported onto 5xObMS, the new codon variant that is approximately 5 times better than 1xObMS. The nineteen mutants in the 1xObMS background exhibited at least about 10% improvement in activity compared to their parent 1xObMS. As summarized in Table 8, about 10-70% improvements in activity were obtained for the majority of mutants over the new parent 5xObMS, a level of improvements similar to that observed with 1xObMS. The myrcene synthase variants with the highest activity, 5xObMS_M543I and 5xObMS_E528D exhibited more than 8-fold improvement over the 1xObMS.

TABLE 8

Beneficial mutations are portable from 1xObMS to 5xObMS. Competition ratios were normalized to that of 5xObMS. The CVs were calculated from 6 replicates. Beneficial mutations selected to be included in the combinatorial library were marked with an "X".

| Residue | Synthase | Improvement | CV | Comb library |
|---|---|---|---|---|
|  | 5xObMS | 0.0% | 4.4% |  |
| 213 | K213C | 9.7% | 2.4% |  |
|  | K213H | 34.9% | 5.3% | x |
|  | K213R | 14.4% | 2.8% |  |
|  | K213V | 9.9% | 0.7% |  |
| 381 | F381L | 9.2% | 5.2% | x |
| 389 | D389G | 31.7% | 5.2% | x |
|  | D389S | 20.7% | 3.2% |  |
| 404 | I404V | 40.9% | 4.2% | x |
| 439 | Y439L | 19.9% | 4.7% | x |
| 482 | R482C | 23.8% | 1.5% |  |
|  | R482D | 43.7% | 2.9% |  |
|  | R482H | 38.1% | 5.3% |  |
|  | R482I | 61.2% | 5.8% | x |
|  | R482L | 50.3% | 4.7% |  |
|  | R482N | 43.2% | 5.6% |  |
|  | R482V | 62.2% | 4.7% |  |
| 484 | H484Y | 2.4% | 3.9% |  |
| 528 | E528D | 68.5% | 3.6% | x |
| 543 | M543I | 69.7% | 3.8% | x |

In order to identify additional beneficial mutations that improve the activity of 5xObMS enzyme, a second saturation mutagenesis library was built and screened with the 5xObMS as parent. To construct the library, 100 amino acid residues were selected to introduce mutations using NDT degenerate primers as described above. The primer sequences are summarized in Table 7. Selection of the 100 amino acid residues were based on two criteria: 1) additional "hot spots" from other terpene synthases (described above) that were not included in the first mutagenesis library; and 2) an ObMS homology model. Residues were selected that are located between 8 and 12 Å from the active site. This library was screened using the same protocol as described above. A total of 29 beneficial mutations at 16 unique amino acid positions were confirmed. Improvements of these variants over the parent 5xObMS range from 12% to 78% based on the competition assay (see Table 9).

TABLE 9

Additional beneficial mutations that were identified from screening a second saturation mutagenesis library of 5xObMS. Competition ratios were normalized to that of 5xObMS. The CVs were calculated from 6 replicates.

| Residue | Synthase variant | Improvement over parent | CV |
|---|---|---|---|
| 27 | H27I | 12% | 1% |
|  | H27C | 17% | 3% |
| 28 | S28H | 55% | 5% |
| 207 | I207V | 50% | 4% |
| 222 | R222N | 53% | 3% |
| 342 | C342L | 68% | 7% |
| 347 | Y347R | 37% | 5% |
| 382 | V382L | 23% | 1% |
| 390 | G390D | 60% | 3% |
| 401 | N401I | 27% | 1% |
|  | N401V | 30% | 1% |
| 428 | V428L | 27% | 4% |
| 466 | A466C | 24% | 3% |
|  | A466S | 71% | 2% |
| 505 | C505I | 62% | 2% |
|  | C505L | 53% | 3% |
|  | C505V | 52% | 1% |

TABLE 9-continued

Additional beneficial mutations that were identified from screening a second saturation mutagenesis library of 5xObMS. Competition ratios were normalized to that of 5xObMS. The CVs were calculated from 6 replicates.

| Residue | Synthase variant | Improvement over parent | CV |
|---|---|---|---|
| 514 | G514L | 22% | 1% |
|  | G514V | 26% | 3% |
| 517 | S517G | 58% | 3% |
| 524 | F524L | 31% | 3% |
|  | F524V | 38% | 1% |
| 527 | V527C | 38% | 4% |
|  | V527F | 78% | 3% |
|  | V527H | 33% | 4% |
|  | V527L | 45% | 1% |
|  | V527N | 54% | 3% |
|  | V527S | 39% | 5% |
|  | V527Y | 47% | 2% |

7.10 Generation of Additional Myrcene Synthase Variants—Screening Combinatorial Libraries This example describes methods for combining mutations and screening for improved myrcene synthase variants using the monoterpene synthase competition assay in yeast.

To further improve the activity of myrcene synthase, eight beneficial mutations (K213H, F381L, D389G, I404V, Y439L, R482I, E528D, and M543I) were selected for the design and construction of a combinatorial library. The 5xObMS was used as the parental sequence. The created library contained all possible 28 combinations of these eight mutations. To create the combinatorial library, overlapping PCR products and gblock sequences (SEQ ID NOs: 39 to 54) comprising the intended mutations were generated. Two PCR reactions were performed with the following primers using the 5xObMS as a template:

```
AMN449:
                                      (SEQ ID NO: 29)
CTATACTTTAACGTCAAGGAGAAAAAACGGATCCATGGTCGAACCAAGAA
GATCCGGTA;
and YY317:
                                      (SEQ ID NO: 30)
ATAAGCTTCAACCAAATCCAACCAAGACTT.
```

PCR products were gel purified. A total of sixteen gblocks was used to introduce all combinations of mutations for F381L, D389G, I404V, Y439L, R482I, E528D, and M543I. Fifty nanograms of each PCR fragment and 10 ng of each gblock were mixed, and an overlap extension PCR reaction was performed with Phusion® High-Fidelity DNA Polymerase. The PCR mixture was first set up without primers, denatured at 95° C. for 3 minutes, followed by 10 cycles (95° C. for 30 seconds, 55° C. for 30 seconds, and 72° C. for 2 minutes). The following primers were added to the reaction:

```
JW730:
                                      (SEQ ID NO: 31)
TACTTTAACGTCAAGGAGAA

ATN009:
                                      (SEQ ID NO: 32)
TTCAGGTTGTCTAACTCCTTCCTTTTCGG
```

After addition of primers JW730 and ATN009, the reaction was performed for another 20 cycles (95° C. for 30 seconds, 56° C. for 30 seconds, and 72° C. for 2 minutes). The amplified full length product was gel-extracted and quantified. 9 ng of the full length product was mixed with 15 ng of BamHI/NheI digested vector pAM 11614, and gap repaired into yeast strain Y10566.

To screen the combinatorial library, 800 yeast clones were inoculated into wells of 96-well plates, grown and assayed as described previously. Yeast clones with increased myrcene/limonene ratio compared to that of the parent strain containing 5xObMS were identified, and their myrcene synthase sequences were amplified and sequenced. Over 50 hits with at least 2-fold improvement over the parent were identified from the initial Tier-1 screening. A subsequent tier screening led to the confirmation of the five top hits with improvements (based on the competition assay) between 2.5 and 2.8-fold over the parent 5xObMs (see Table 10).

TABLE 10

Top five hits identified from screening the myrcene synthase combinatorial library. Their improvements are relative to the parent of the library 5xObMS. Their improvements relative to the enzyme 1xObMS are also listed for the purpose of tracking the overall progress of myrcene synthase engineering.

| Hit | Activity relative to 5xObMS (Parent) | Overall activity Relative to 1xObMS | Amino acid mutations (as compared to wild-type ObMS) |
|---|---|---|---|
| T4-2 and T4-36 | 2.5 | 12.5 | F381L, I404V, E528D, M543I |
| T4-5 | 2.5 | 12.5 | I404V, E528D |
| T4-22 | 2.5 | 12.5 | F381L, D389G, I404V, Y439L, E528D |
| T4-23 | 2.5 | 12.5 | F381L, E528D, M543I |
| T4-43 | 2.8 | 14 | F381L, I404V, E528D |

Sequences of these top hits led to some valuable insights into these beneficial mutations. All hits contain the E528D mutation, which appeared to be one of the best beneficial mutations among the eight mutations included in this combinatorial library. On the other hand, none of the top hits contain either K213H or R482I mutation. In addition, there appears to be a synergistic effect between I404V and E528D as the improvement with both mutations together (250% in the Hit T4-5 and likely in the Hit T4-43) exceeded the sum of the two individual improvements (~110%). In contrast, E528, M543I and F381L mutations appear to be fully additive when combined, generating a total of 150% improvement in activity as expected from the sum of their individual improvements (from Table 10). The hit T4-43 which contains three amino acid changes (F381L, I404V, and E528D) is herein referred to as 14×ObMS variant because its overall activity is 14 times greater than that of 1×ObMS (the wild-type myrcene synthase from *Ocimum basilicum*).

7.11 Improvement of Myrcene Production in 14×ObMS Variant

This example illustrates improved myrcene production by the ObMS variants 5×ObMS and 14×ObMS compared to the wild-type 1×ObMS.

Screening host strain X100 was created by integrating two copies of pGAL1 promoter driven SaGPPS, along with an endonuclease landing pad for myrcene synthases. The landing pad consists of the pGAL1 promoter, the F-Cphl cut site, and a terminator. The 1×ObMS, 5×ObMS, and 14×ObMS were amplified with primers that contain homology to the pGAL1 promoter and the terminator, and each was cotransformed with pAM2947 plasmid containing the F-Cphl endonuclease into strains X100 to create new strains, each with a single copy of 1×ObMS, 5×ObMS, and 14×ObMS, respectively, integrated into the chromosome. These strains were tested for production in the sealed 2.2 ml 96 well plate model, containing 120 µl 1% sucrose, and 30 µl IPM with 1 g/L limonene as an internal standard. After 72 hours incubation at 30° C. with shaking, the samples in the plate were analyzed and myrcene production was quantified using the headspace analysis as described in Example 7.5.

The results are shown in FIG. 6. As shown in FIG. 6, the rapid improvement has been made to the wild-type 1×ObMS enzyme via combination of codon optimization (5×ObMS variant) and via a combination of codon optimization and directed evolution (14×ObMS variant). Compared to the wild-type 1×ObMS nucleic acid (which is not codon optimized), the 14×ObMS variant, when expressed in yeast cells, exhibited improved myrcene production by about 3.5 fold compared to the wild-type 1×ObMS.

7.12 ObMS Variants with Improvement Over their Parent 14×ObMS

This example describes methods of screening for improved myrcene synthase variants over their parent 14×ObMS in a monoterpene synthase competition assay in yeast.

Site-directed mutagenesis library was created by polymerase chain reaction (PCR) mutagenesis using the 14×ObMS sequence as template. The parent 14×ObMS enzyme contains three amino acids (F381L, I404V and E528D). Mutations were introduced using degenerate NDT codon on the 14×ObMS sequence (SEQ ID NO: 4) as described above in Section 6.9. Primer sequences are listed in Table 7 shown above. Screening and competition/headspace assays were carried out as described previously in Examples 6.4, 6.5, and 6.9 using strain Y10566.

Two hits were identified and confirmed from the screening assays. After sequencing myrcene synthase sequences in these two hits, the exact changes in nucleotide sequences were determined. These two hits are: A544S (codon change from gct to agt) and Q552R (codon change caa to cgt). The improvements of myrcene synthase activity of these two hits over the parent 14×ObMS are shown in FIG. 7, where the Y-axis shows the percent improvement over the parent enzyme. As shown in FIG. 7, both mutations A544S and Q552R improved myrcene synthase activity by at least 10% over the parent 14×ObMS.

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing embodiments have been described in some detail by way of illustration and example for purposes of clarity of understanding, it will be readily apparent to those of ordinary skill in the art in light of the teachings of embodiments of this invention that certain changes and modifications may be made thereto without departing from the spirit or scope of the appended claims.

What is claimed is:

1. A fermentation composition comprising:
   (a) a genetically modified microbial host cell cultured in a culture medium, wherein the microbial host cell comprises a heterologous nucleic acid molecule encoding a myrcene synthase, wherein the myrcene synthase comprises a sequence that has at least about 70% sequence identity to SEQ ID NO: 2, and at least one variant amino acid residue at position 27, 28, 207, 213, 222, 342, 347, 381, 382, 389, 390, 401, 404, 428, 439, 466, 482, 484, 505, 514, 517, 524, 527, 528, 543, 544, or 552, wherein the positions are numbered with reference to SEQ ID NO: 2; and
   (b) monoterpenes produced from the microbial host cell, wherein the monoterpenes comprise myrcene as a major component and one or more co-products as minor components, wherein the one or more co-products comprise α-terpinene and γ-terpinene.

2. The fermentation composition of claim 1, wherein the one or more co-products further comprise 4-terpineol.

3. The fermentation composition of claim 1, wherein the one or more co-products further comprise sabinene, limonene, β-ocimene, or β-linalool.

4. The fermentation composition of claim 1, wherein the one or more co-products further comprise α-thujene, (E)-sabinene hydrate, or (Z)-sabinene hydrate.

5. The fermentation composition of claim 1, wherein the monoterpenes comprise at least about 85% myrcene and less than about 15% the one or more co-products, compared to the total amount of the monoterpenes.

6. The fermentation composition of claim 1, wherein the monoterpenes comprise between about 88% to about 93% myrcene, compared to the total amount of the monoterpenes.

7. The fermentation composition of claim 1, wherein the monoterpenes comprise between about 0.5% to about 1% α-terpinene, compared to the total amount of the monoterpenes.

8. The fermentation composition of claim 1, wherein the monoterpenes comprise between about 0.5% to about 1.5% γ-terpinene, compared to the total amount of the monoterpenes.

9. The fermentation composition of claim 1, wherein the monoterpenes comprise between about 1% to about 3% 4-terpineol, compared to the total amount of the monoterpenes.

10. The fermentation composition of claim 1, wherein the monoterpenes comprise, based on the total amount of the monoterpenes: about 89.09% to about 92.01% myrcene, about 0.80% to about 0.98% sabinene, about 0.67% to about 0.90% α-terpinene, about 0.54% to about 1.01% limonene, about 0.91% to about 1.21% β-ocimene, about 1.00% to about 1.06% γ-terpinene, about 0.76% to about 1.17% β-linalool, and about 2.32% to about 2.42% 4-terpineol.

11. The fermentation composition of claim 10, wherein the monoterpenes further comprise, based on the total amount of the monoterpenes: about 0% to about 0.51% α-thujene, about 0% to about 0.54% (E)-sabinene hydrate, and about 0.98% to about 1.13% (Z)-sabinene hydrate.

12. The fermentation composition of claim 1, wherein the myrcene synthase exhibits an improved activity for converting geranyl diphosphate into myrcene compared to the activity of a myrcene synthase of SEQ ID NO: 2 under identical reaction conditions.

13. The fermentation composition of claim 1, wherein the myrcene synthase exhibits an improved activity for converting geranyl diphosphate into myrcene compared to the activity of a myrcene synthase isolated from *Quercus* ilex, *Abies grandis, Antirrhinum majus, Arabidopsis thaliana, Aegilops squarrosa, Alstroemeria peruviana* or *Picea abies* under identical reaction conditions.

14. The fermentation composition of claim 1, wherein the heterologous nucleic acid molecule encoding the myrcene synthase is a nucleic acid molecule encoding *Ocimum basilicum* myrcene synthase.

15. The fermentation composition of claim 1, wherein the myrcene synthase comprises an amino acid sequence having at least about 75% sequence identity to SEQ ID NO: 2.

16. The fermentation composition of claim 1, wherein the at least one variant amino acid residue is selected from the group consisting of H27I, H27C, S28H, I207V, K213C, K213H, K213R, K213V, R222N, C342L, Y347R, F381L, V382L, D389G, D389S, G390D, N401I, N401V, I404V, V428L, Y439L, A466C, A466S, R482C, R482D, R482H, R482I, R482L, R482N, R482V, H484Y, C505I, C505L, C505V, G514L, G514V, S517G, F524L, F524V, V527C, V527F, V527H, V527L, V527N, V527S, V527Y, E528D, M543I, A544S, and Q552R, wherein the positions are numbered with reference to SEQ ID NO: 2.

17. The fermentation composition of claim 16, wherein the myrcene synthase comprises at least one set of variant amino acid residues compared to SEQ ID NO: 2, and wherein the at least one set of variant amino acid residues is selected from the group of sets of variant amino acid residues consisting of:
(a) F381L, I404V, E528D, and M543I;
(b) I404V and E528D;
(c) F381L, D389G, I404V, Y439L, and E528D;
(d) F381L, E528D, and M543I;
(e) F381L, I404V, and E528D;
(f) F381L, I404V, E528D, and A544S; and
(g) F381L, I404V, E528D, and Q552R,
wherein the positions are numbered with reference to SEQ ID NO: 2.

18. The fermentation composition of claim 17, wherein the myrcene synthase comprises variant amino acid residues F381L, I404V, and E528D compared to SEQ ID NO: 2, wherein the positions are numbered with reference to SEQ ID NO: 2.

19. A fermentation composition comprising:
(a) a genetically modified microbial host cell cultured in a culture medium, wherein the microbial host cell comprises a heterologous nucleic acid molecule encoding a myrcene synthase, wherein the myrcene synthase comprises a sequence that has at least about 70% sequence identity to SEQ ID NO: 2, and wherein the myrcene synthase comprises variant amino acid residues F381L, I404V, E528D, and A544S compared to SEQ ID NO: 2, wherein the positions are numbered with reference to SEQ ID NO: 2;
(b) monoterpenes produced from the microbial host cell, wherein the monoterpenes comprise myrcene as a major component and one or more co-products as minor components, wherein the one or more co-products comprise α-terpinene and γ-terpinene.

20. A fermentation composition comprising:
(a) a genetically modified microbial host cell cultured in a culture medium, wherein the microbial host cell comprises a heterologous nucleic acid molecule encoding a myrcene synthase, wherein the myrcene synthase comprises a sequence that has at least about 70% sequence identity to SEQ ID NO: 2, and wherein the myrcene synthase comprises variant amino acid residues F381L, I404V, E528D, and Q552R compared to SEQ ID NO: 2, wherein the positions are numbered with reference to SEQ ID NO: 2;
(b) monoterpenes produced from the microbial host cell, wherein the monoterpenes comprise myrcene as a major component and one or more co-products as minor components, wherein the one or more co-products comprise α-terpinene and γ-terpinene.

21. The fermentation composition of claim 1, wherein the heterologous nucleic acid molecule encoding the myrcene synthase comprises a nucleotide sequence having at least about 70% SEQ ID NO: 1, SEQ ID NO: 3, or SEQ ID NO: 4.

22. The fermentation composition of claim 1, wherein the myrcene synthase has 80% identity to SEQ ID NO: 2.

23. The fermentation composition of claim 1, wherein the myrcene synthase has 90% identity to SEQ ID NO: 2.

24. The fermentation composition of claim 1, wherein the myrcene synthase has 95% identity to SEQ ID NO: 2.

* * * * *

SEQUENCE LISTING

<160> NUMBER OF SEQ ID NOS: 88

<210> SEQ ID NO 1
<211> LENGTH: 1659
<212> TYPE: DNA
<213> ORGANISM: Ocimum basilicum
<220> FEATURE:
<221> NAME/KEY: misc_feature
<223> OTHER INFORMATION: 1xObMS nucleic acid (wild-type Ocimum basilicum
      myrcene synthase after truncation of a transit peptide)

<400> SEQUENCE: 1

```
atggttgaac cccgacgctc cggaaactac cagccttcag cttgggattt caactacatt      60
caatctctca ataataatca ctccaaggag gagaggcatt tggaaaggaa agctaagctg     120
attgaggaag tgaagatgct attggagcag gaaatggcgg cagttcaaca gttggagttg     180
attgaagact gaaaaatct gggattgtca tacttatttc aagatgagat taaaataatt     240
ttgaattcca tatacaatca ccacaaatgc ttccacaata atcatgaaca atgcatacac     300
gtaaattcag atttgtattt cgtcgctctc ggattcagac tcttccggca acatggtttt     360
aaagtctctc aagaagtatt tgactgtttt aagaacgaag agggcagtga tttcagtgca     420
```

```
aaccttgctg acgatacaaa ggggctgcta caactttacg aagcgtcata tctggtgaca    480
gaagatgaag atacactgga gatggcgcga caattttcca ccaaaattct gcagaaaaaa    540
gtggaagaaa aaatgattga aaggagaat tgttatcat ggacacttca ttctttggag     600
```

```
aaccttgctg acgatacaaa ggggctgcta caactttacg aagcgtcata tctggtgaca    480
gaagatgaag atacactgga gatggcgcga caattttcca ccaaaattct gcagaaaaaa    540
gtggaagaaa aaatgattga aaggagaat tgttatcat ggacacttca ttctttggag     600
ctcccacttc attggcggat tcaaaggctg gaggccaaat ggttcttaga tgcttatgct    660
agcagaccag atatgaatcc cattattttt gagttggcta aattggaatt caatattgct    720
caagcattac aacaggaaga actcaaagat ctctcaaggt ggtggaatga tactggtatt    780
gccgaaaaac tcccatttgc gagggatcga atagttgaat cccactattg ggcaattgga    840
acccttgagc cttatcaata tagatatcaa agaagcctca tcgccaagat tattgcccta    900
actacagttg ttgatgatgt ctacgatgtg tacggcacat tggatgaact ccaactattc    960
acagacgcaa ttcgaagatg ggatattgaa tcaatcaacc aacttcctag ttacatgcaa    1020
ctatgctatt tggcaatcta caactttgtt tctgagctgg cttacgatat tttccgagac    1080
aagggtttca acagcctccc atacttacac aaatcgtggc tggatttggt tgaagcatat    1140
tttgttgagg caaagtggtt ccacgatgga tatactccaa ctctagaaga atatctcaac    1200
aattcgaaga taacaataat tgtcctgca atagtctcag aaatatactt cgcatttgca    1260
aactccatcg acaaaacaga ggtcgagagc atatacaaat atcatgacat cctttacctt    1320
tccggaatgc ttgcaaggct tcccgatgat ttgggaacat catcgtttga tgaagaga     1380
ggtgacgtgg cgaaagcaat tcagtgttac atgaaggagc ataacgcctc agaggaggag    1440
gcacgtgagc acatcagatt tcttatgcgg gaggcgtgga agcatatgaa cacggcggct    1500
gcggccgacg actgtccatt tgagagtgac ttagttgtgg gtgcagctag tctcggaaga    1560
gtggctaatt ttgtgtatgt ggagggagat ggttttggag tgcaacactc aaaaatacat    1620
caacaaatgg ctgaattact gttttaccca tatcagtaa                           1659
```

<210> SEQ ID NO 2
<211> LENGTH: 552
<212> TYPE: PRT
<213> ORGANISM: Ocimum basilicum
<220> FEATURE:
<221> NAME/KEY: misc_feature
<223> OTHER INFORMATION: 1xObMS amino acid (wild-type Ocimum basilicum
      myrcene synthase after truncation of a transit peptide)

<400> SEQUENCE: 2

Met Val Glu Pro Arg Arg Ser Gly Asn Tyr Gln Pro Ser Ala Trp Asp
1               5                   10                  15

Phe Asn Tyr Ile Gln Ser Leu Asn Asn Asn His Ser Lys Glu Glu Arg
            20                  25                  30

His Leu Glu Arg Lys Ala Lys Leu Ile Glu Glu Val Lys Met Leu Leu
        35                  40                  45

Glu Gln Glu Met Ala Ala Val Gln Gln Leu Glu Leu Ile Glu Asp Leu
    50                  55                  60

Lys Asn Leu Gly Leu Ser Tyr Leu Phe Gln Asp Glu Ile Lys Ile Ile
65                  70                  75                  80

Leu Asn Ser Ile Tyr Asn His His Lys Cys Phe His Asn Asn His Glu
                85                  90                  95

Gln Cys Ile His Val Asn Ser Asp Leu Tyr Phe Val Ala Leu Gly Phe
            100                 105                 110

Arg Leu Phe Arg Gln His Gly Phe Lys Val Ser Gln Glu Val Phe Asp
        115                 120                 125

Cys Phe Lys Asn Glu Glu Gly Ser Asp Phe Ser Ala Asn Leu Ala Asp

-continued

```
            130                 135                 140
Asp Thr Lys Gly Leu Leu Gln Leu Tyr Glu Ala Ser Tyr Leu Val Thr
145                 150                 155                 160

Glu Asp Glu Asp Thr Leu Glu Met Ala Arg Gln Phe Ser Thr Lys Ile
                165                 170                 175

Leu Gln Lys Lys Val Glu Glu Lys Met Ile Glu Lys Glu Asn Leu Leu
                180                 185                 190

Ser Trp Thr Leu His Ser Leu Glu Leu Pro Leu His Trp Arg Ile Gln
                195                 200                 205

Arg Leu Glu Ala Lys Trp Phe Leu Asp Ala Tyr Ala Ser Arg Pro Asp
                210                 215                 220

Met Asn Pro Ile Ile Phe Glu Leu Ala Lys Leu Glu Phe Asn Ile Ala
225                 230                 235                 240

Gln Ala Leu Gln Gln Glu Glu Leu Lys Asp Leu Ser Arg Trp Trp Asn
                245                 250                 255

Asp Thr Gly Ile Ala Glu Lys Leu Pro Phe Ala Arg Asp Arg Ile Val
                260                 265                 270

Glu Ser His Tyr Trp Ala Ile Gly Thr Leu Glu Pro Tyr Gln Tyr Arg
                275                 280                 285

Tyr Gln Arg Ser Leu Ile Ala Lys Ile Ile Ala Leu Thr Thr Val Val
                290                 295                 300

Asp Asp Val Tyr Asp Val Tyr Gly Thr Leu Asp Glu Leu Gln Leu Phe
305                 310                 315                 320

Thr Asp Ala Ile Arg Arg Trp Asp Ile Glu Ser Ile Asn Gln Leu Pro
                325                 330                 335

Ser Tyr Met Gln Leu Cys Tyr Leu Ala Ile Tyr Asn Phe Val Ser Glu
                340                 345                 350

Leu Ala Tyr Asp Ile Phe Arg Asp Lys Gly Phe Asn Ser Leu Pro Tyr
                355                 360                 365

Leu His Lys Ser Trp Leu Asp Leu Val Glu Ala Tyr Phe Val Glu Ala
                370                 375                 380

Lys Trp Phe His Asp Gly Tyr Thr Pro Thr Leu Glu Glu Tyr Leu Asn
385                 390                 395                 400

Asn Ser Lys Ile Thr Ile Ile Cys Pro Ala Ile Val Ser Glu Ile Tyr
                405                 410                 415

Phe Ala Phe Ala Asn Ser Ile Asp Lys Thr Glu Val Glu Ser Ile Tyr
                420                 425                 430

Lys Tyr His Asp Ile Leu Tyr Leu Ser Gly Met Leu Ala Arg Leu Pro
                435                 440                 445

Asp Asp Leu Gly Thr Ser Ser Phe Glu Met Lys Arg Gly Asp Val Ala
                450                 455                 460

Lys Ala Ile Gln Cys Tyr Met Lys Glu His Asn Ala Ser Glu Glu Glu
465                 470                 475                 480

Ala Arg Glu His Ile Arg Phe Leu Met Arg Glu Ala Trp Lys His Met
                485                 490                 495

Asn Thr Ala Ala Ala Ala Asp Asp Cys Pro Phe Glu Ser Asp Leu Val
                500                 505                 510

Val Gly Ala Ala Ser Leu Gly Arg Val Ala Asn Phe Val Tyr Val Glu
                515                 520                 525

Gly Asp Gly Phe Gly Val Gln His Ser Lys Ile His Gln Gln Met Ala
530                 535                 540

Glu Leu Leu Phe Tyr Pro Tyr Gln
545                 550
```

<210> SEQ ID NO 3
<211> LENGTH: 1659
<212> TYPE: DNA
<213> ORGANISM: Artificial Sequence
<220> FEATURE:
<223> OTHER INFORMATION: Synthetic: 5xObMS nucleic acid (codon
      optimization of the 1xObMS)

<400> SEQUENCE: 3

| | |
|---|---|
| atggtcgaac caagaagatc cggtaactac caaccatccg cttgggattt taattacatt | 60 |
| caatccttga caacaacca ttccaaggaa gaacgtcatt tggaaagaaa ggctaagtta | 120 |
| attgaagaag tcaagatgtt attagagcaa gaaatggctg ctgttcaaca attggaatta | 180 |
| attgaagact tgaagaactt gggtttgtcc tacttgtttc aagatgaaat taaaatcatt | 240 |
| ttgaactcta tttacaacca ccataaatgt ttccacaata accatgaaca atgcattcac | 300 |
| gttaactctg acttgtactt tgtcgccttg ggtttcagat tgttcagaca catggtttc | 360 |
| aaggtttctc aagaagtttt cgattgcttc aagaacgaag aaggttccga cttttccgct | 420 |
| aacttggctg atgatactaa aggttttgttg caattgtatg aggcttctta cttggttact | 480 |
| gaagatgaag atactttaga atggccaga caattttcca ccaagatctt gcaaaagaag | 540 |
| gtcgaagaga agatgattga aaggaaaac ttattgtctt ggaccttgca ctctttggag | 600 |
| ttacctttgc attggagaat ccaaagattg gaggccaaat ggttcttgga tgcctacgcc | 660 |
| tctagaccag atatgaaccc aattattttc gaattggcca agttggaatt taacattgct | 720 |
| caagccttgc aacaagaaga attgaaggac ttgtctagat ggtggaacga cactggtatt | 780 |
| gctgaaaagt tgccttttcgc tagagataga attgtcgaat ctcattactg ggccatcgt | 840 |
| actttggaac ataccaata cagataccaa agatctttga tcgccaaaat catcgccttg | 900 |
| accactgtcg tcgatgacgt ttatgacgtc tacggtactt ggacgaatt acaattattc | 960 |
| accgacgcca tcagaagatg ggacattgaa tctatcaacc aattgccatc ttacatgcaa | 1020 |
| tgtgctatt tggccattta taacttcgtc tccgaattgg cttacgacat tttccgtgat | 1080 |
| aagggtttca actctttacc atacttgcac aagtcttggt tggatttggt tgaagcttat | 1140 |
| ttcgttgaag ccaagtggtt ccacgacggt tacactccaa ctttggaaga atacttgaac | 1200 |
| aactctaaga ttactatcat ttgtccagcc atcgtttccg aaatttactt cgcttttgcc | 1260 |
| aactctatcg ataagactga agttgaatcc atttacaagt atcacgacat tttgtacttg | 1320 |
| tccggtatgt tggctagatt gccagacgat ttgggtacct cttccttcga gatgaagcgt | 1380 |
| ggtgacgttg ctaaggccat tcaatgttac atgaaggaac acaacgcctc tgaggaagaa | 1440 |
| gctagagaac atattcgttt cttgatgaga gaagcttgga agcacatgaa cactgccgct | 1500 |
| gctgccgatg actgtccatt tgaatctgac ttggttgttg gtgctgcctc cttgggtaga | 1560 |
| gtcgctaact tcgtctacgt tgagggtgat ggtttcggtg tccaacactc taagattcac | 1620 |
| caacaaatgg ctgaattatt gttttaccca taccaataa | 1659 |

<210> SEQ ID NO 4
<211> LENGTH: 1659
<212> TYPE: DNA
<213> ORGANISM: Artificial Sequence
<220> FEATURE:
<223> OTHER INFORMATION: Synthetic: 14xObMS nucleic acid

<400> SEQUENCE: 4

| | |
|---|---|
| atggtcgaac caagaagatc cggtaactac caaccatccg cttgggattt taattacatt | 60 |

```
caatccttga acaacaacca ttccaaggaa gaacgtcatt tggaaagaaa ggctaagtta    120
attgaagaag tcaagatgtt attagagcaa gaaatggctg ctgttcaaca attggaatta    180
attgaagact tgaagaactt gggtttgtcc tacttgtttc aagatgaaat taaaatcatt    240
ttgaactcta tttacaacca ccataaatgt ttccacaata accatgaaca atgcattcac    300
gttaactctg acttgtactt tgtcgccttg ggtttcagat tgttcagaca acatggtttc    360
aaggtttctc aagaagtttt cgattgcttc aagaacgaag aaggttccga cttttccgct    420
aacttggctg atgatactaa aggtttgttg caattgtatg aggcttctta cttggttact    480
gaagatgaag atactttaga aatggccaga caatttccca ccaagatctt gcaaaagaag    540
gtcgaagaga agatgattga aaaggaaaac ttattgtctt ggaccttgca ctctttggag    600
ttacctttgc attggagaat ccaaagattg gaggccaaat ggttcttgga tgcctacgcc    660
tctagaccag atatgaaccc aattattttc gaattggcca agttggaatt taacattgct    720
caagccttgc aacaagaaga attgaaggac ttgtctagat ggtggaacga cactggtatt    780
gctgaaaagt tgcctttcgc tagagataga attgtcgaat ctcattactg ggccatcggt    840
actttggaac ataccaata cagataccaa agatctttga tcgccaaaat catcgccttg    900
accactgtcg tcgatgacgt ttatgacgtc tacggtactt tggacgaatt acaattattc    960
accgacgcca tcagaagatg ggacattgaa tctatcaacc aattgccatc ttacatgcaa   1020
ttgtgctatt tggccattta taacttcgtc tccgaattgg cttacgacat tttccgtgat   1080
aagggtttca ctctttacc atacttgcac aagtcttggt tggatttggt tgaagcttat   1140
cttgttgaag ccaagtggtt ccacgacggt tacactccaa ctttggaaga atacttgaac   1200
aactctaagg ttactatcat ttgtccagcc atcgtttccg aaatttactt cgcttttgcc   1260
aactctatcg ataagactga agttgaatcc atttacaagt atcacgacat tttgtacttg   1320
tccggtatgt tggctagatt gccagacgat ttgggtacct cttccttcga gatgaagcgt   1380
ggtgacgttg ctaaggccat tcaatgttac atgaaggaac acaacgcctc tgaggaagaa   1440
gctagagaac atattcgttt cttgatgaga gaagcttgga agcacatgaa cactgccgct   1500
gctgccgatg actgtccatt tgaatctgac ttggttgttg gtgctgcctc cttgggtaga   1560
gtcgctaact tcgtctacgt tgatggtgat ggtttcggtg tccaacactc taagattcac   1620
caacaaatgg ctgaattatt gttttacccca taccaataa                         1659
```

<210> SEQ ID NO 5  
<211> LENGTH: 552  
<212> TYPE: PRT  
<213> ORGANISM: Artificial Sequence  
<220> FEATURE:  
<223> OTHER INFORMATION: Synthetic: 14xObMS amino acid (hit from the combinatorial library design. 14x has 3 amino acid changes compared to 5xObMS: F381L, I404V, and E528D)

<400> SEQUENCE: 5

```
Met Val Glu Pro Arg Arg Ser Gly Asn Tyr Gln Pro Ser Ala Trp Asp
 1               5                  10                  15

Phe Asn Tyr Ile Gln Ser Leu Asn Asn Asn His Ser Lys Glu Glu Arg
            20                  25                  30

His Leu Glu Arg Lys Ala Lys Leu Ile Glu Glu Val Lys Met Leu Leu
        35                  40                  45

Glu Gln Glu Met Ala Ala Val Gln Gln Leu Glu Leu Ile Glu Asp Leu
    50                  55                  60
```

```
Lys Asn Leu Gly Leu Ser Tyr Leu Phe Gln Asp Glu Ile Lys Ile Ile
 65                  70                  75                  80

Leu Asn Ser Ile Tyr Asn His His Lys Cys Phe His Asn Asn His Glu
                 85                  90                  95

Gln Cys Ile His Val Asn Ser Asp Leu Tyr Phe Val Ala Leu Gly Phe
            100                 105                 110

Arg Leu Phe Arg Gln His Gly Phe Lys Val Ser Gln Glu Val Phe Asp
            115                 120                 125

Cys Phe Lys Asn Glu Glu Gly Ser Asp Phe Ser Ala Asn Leu Ala Asp
130                 135                 140

Asp Thr Lys Gly Leu Leu Gln Leu Tyr Glu Ala Ser Tyr Leu Val Thr
145                 150                 155                 160

Glu Asp Glu Asp Thr Leu Glu Met Ala Arg Gln Phe Ser Thr Lys Ile
                165                 170                 175

Leu Gln Lys Lys Val Glu Glu Lys Met Ile Glu Lys Glu Asn Leu Leu
                180                 185                 190

Ser Trp Thr Leu His Ser Leu Glu Leu Pro Leu His Trp Arg Ile Gln
            195                 200                 205

Arg Leu Glu Ala Lys Trp Phe Leu Asp Ala Tyr Ala Ser Arg Pro Asp
210                 215                 220

Met Asn Pro Ile Ile Phe Glu Leu Ala Lys Leu Glu Phe Asn Ile Ala
225                 230                 235                 240

Gln Ala Leu Gln Gln Glu Leu Lys Asp Leu Ser Arg Trp Trp Asn
            245                 250                 255

Asp Thr Gly Ile Ala Glu Lys Leu Pro Phe Ala Arg Asp Arg Ile Val
            260                 265                 270

Glu Ser His Tyr Trp Ala Ile Gly Thr Leu Glu Pro Tyr Gln Tyr Arg
            275                 280                 285

Tyr Gln Arg Ser Leu Ile Ala Lys Ile Ile Ala Leu Thr Thr Val Val
            290                 295                 300

Asp Asp Val Tyr Asp Val Tyr Gly Thr Leu Asp Glu Leu Gln Leu Phe
305                 310                 315                 320

Thr Asp Ala Ile Arg Arg Trp Asp Ile Glu Ser Ile Asn Gln Leu Pro
                325                 330                 335

Ser Tyr Met Gln Leu Cys Tyr Leu Ala Ile Tyr Asn Phe Val Ser Glu
            340                 345                 350

Leu Ala Tyr Asp Ile Phe Arg Asp Lys Gly Phe Asn Ser Leu Pro Tyr
            355                 360                 365

Leu His Lys Ser Trp Leu Asp Leu Val Glu Ala Tyr Leu Val Glu Ala
    370                 375                 380

Lys Trp Phe His Asp Gly Tyr Thr Pro Thr Leu Glu Glu Tyr Leu Asn
385                 390                 395                 400

Asn Ser Lys Val Thr Ile Ile Cys Pro Ala Ile Val Ser Glu Ile Tyr
                405                 410                 415

Phe Ala Phe Ala Asn Ser Ile Asp Lys Thr Glu Val Glu Ser Ile Tyr
            420                 425                 430

Lys Tyr His Asp Ile Leu Tyr Leu Ser Gly Met Leu Ala Arg Leu Pro
            435                 440                 445

Asp Asp Leu Gly Thr Ser Ser Phe Glu Met Lys Arg Gly Asp Val Ala
            450                 455                 460

Lys Ala Ile Gln Cys Tyr Met Lys Glu His Asn Ala Ser Glu Glu Glu
465                 470                 475                 480

Ala Arg Glu His Ile Arg Phe Leu Met Arg Glu Ala Trp Lys His Met
```

```
                      485                 490                 495
Asn Thr Ala Ala Ala Asp Asp Cys Pro Phe Glu Ser Asp Leu Val
            500                 505                 510

Val Gly Ala Ala Ser Leu Gly Arg Val Ala Asn Phe Val Tyr Val Asp
            515                 520                 525

Gly Asp Gly Phe Gly Val Gln His Ser Lys Ile His Gln Gln Met Ala
        530                 535                 540

Glu Leu Leu Phe Tyr Pro Tyr Gln
545                 550
```

<210> SEQ ID NO 6
<211> LENGTH: 1070
<212> TYPE: DNA
<213> ORGANISM: Streptomyces aculeolatus
<220> FEATURE:
<221> NAME/KEY: misc_feature
<223> OTHER INFORMATION: Streptomyces aculeolatus geranyl pyrophosphate
      synthase nucleic acid encoding 'SaGPPS" (codon optimized for S.
      cerevisiae)

<400> SEQUENCE: 6

```
atgaccaccg aagtcacttc cttcactggt gccggtccac acccagctgc ttctgttaga    60
cgtattactg acgacttatt gcaaagagtt gaagacaagt tggcctcctt cttgactgct   120
gagagagaca gatacgccgc catggatgaa agagctttgg ccgccgtcga cgctttaacc   180
gacttggtca cttccggtgg taagagagtt agacctactt tctgtattac cggttatttg   240
gctgctggtg gtgatgccgg tgatccaggt attgttgctg ctgctgctgg tttggaaatg   300
ttgcatgttt ctgctttgat tcatgacgat atcttggata actccgctca agaagaggt    360
aagccaacta ttcacacttt ataccggtgat ttacatgact cccacggttg agaggtgaa   420
tcccgtagat tcggtgaagg tatcggtatt ttgattggta atttagcctt ggtttattct   480
caagaattgg tctgtcaagc cccaccagct gtcttagctg aatggcatag attatgctct   540
gaagttaaca ttggtcaatg tttggacgtt tgtgctgccg ctgagttctc tgctgatcca   600
gaattatctc gtttggttgc cttgatcaag tctggtagat ataccattca ccgtccattg   660
gttatgggtg ctaacgctgc ctctagacca gacttagctg ctgcttatgt tgaatacggt   720
gaagctgtcg gtgaagcttt ccaattgcgt gatgacttgt ggatgctttt ggtgactct   780
actgaaaccg gtaaaccaac cggtttggac tttactcaac ataagatgac tttgttgtta   840
ggttgggcta tgcaacgtga cacccatatt agaaccttga tgactgaacc tggtcatact   900
ccagaggaag ttagaagaag attggaagat accgaagttc aaaggacgt tgagcgtcac    960
atcgctgatt ggttgaacaa ggtagagct gccatcgccg acgccccaat tgaccctcaa   1020
tggagacaag aattggctga tatggctgtt agagccgcct acagaactaa               1070
```

<210> SEQ ID NO 7
<211> LENGTH: 356
<212> TYPE: PRT
<213> ORGANISM: Streptomyces aculeolatus
<220> FEATURE:
<221> NAME/KEY: misc_feature
<223> OTHER INFORMATION: Streptomyces aculeolatus geranyl pyrophosphate
      synthase "SaGPPS"

<400> SEQUENCE: 7

```
Met Thr Thr Glu Val Thr Ser Phe Thr Gly Ala Gly Pro His Pro Ala
1               5                   10                  15

Ala Ser Val Arg Arg Ile Thr Asp Asp Leu Leu Gln Arg Val Glu Asp
```

```
            20                  25                  30
Lys Leu Ala Ser Phe Leu Thr Ala Glu Arg Asp Arg Tyr Ala Ala Met
        35                  40                  45

Asp Glu Arg Ala Leu Ala Ala Val Asp Ala Leu Thr Asp Leu Val Thr
    50                  55                  60

Ser Gly Gly Lys Arg Val Arg Pro Thr Phe Cys Ile Thr Gly Tyr Leu
 65                 70                  75                  80

Ala Ala Gly Gly Asp Ala Gly Asp Pro Gly Ile Val Ala Ala Ala
                85                  90                  95

Gly Leu Glu Met Leu His Val Ser Ala Leu Ile His Asp Asp Ile Leu
            100                 105                 110

Asp Asn Ser Ala Gln Arg Arg Gly Lys Pro Thr Ile His Thr Leu Tyr
        115                 120                 125

Gly Asp Leu His Asp Ser His Gly Trp Arg Gly Glu Ser Arg Arg Phe
    130                 135                 140

Gly Glu Gly Ile Gly Ile Leu Ile Gly Asn Leu Ala Leu Val Tyr Ser
145                 150                 155                 160

Gln Glu Leu Val Cys Gln Ala Pro Pro Ala Val Leu Ala Glu Trp His
            165                 170                 175

Arg Leu Cys Ser Glu Val Asn Ile Gly Gln Cys Leu Asp Val Cys Ala
        180                 185                 190

Ala Ala Glu Phe Ser Ala Asp Pro Glu Leu Ser Arg Leu Val Ala Leu
    195                 200                 205

Ile Lys Ser Gly Arg Tyr Thr Ile His Arg Pro Leu Val Met Gly Ala
210                 215                 220

Asn Ala Ala Ser Arg Pro Asp Leu Ala Ala Tyr Val Glu Tyr Gly
225                 230                 235                 240

Glu Ala Val Gly Glu Ala Phe Gln Leu Arg Asp Asp Leu Leu Asp Ala
            245                 250                 255

Phe Gly Asp Ser Thr Glu Thr Gly Lys Pro Thr Gly Leu Asp Phe Thr
        260                 265                 270

Gln His Lys Met Thr Leu Leu Leu Gly Trp Ala Met Gln Arg Asp Thr
    275                 280                 285

His Ile Arg Thr Leu Met Thr Glu Pro Gly His Thr Pro Glu Glu Val
290                 295                 300

Arg Arg Arg Leu Glu Asp Thr Glu Val Pro Lys Asp Val Glu Arg His
305                 310                 315                 320

Ile Ala Asp Leu Val Glu Gln Gly Arg Ala Ala Ile Ala Asp Ala Pro
            325                 330                 335

Ile Asp Pro Gln Trp Arg Gln Glu Leu Ala Asp Met Ala Val Arg Ala
        340                 345                 350

Ala Tyr Arg Thr
        355

<210> SEQ ID NO 8
<211> LENGTH: 891
<212> TYPE: DNA
<213> ORGANISM: Abies grandis
<220> FEATURE:
<221> NAME/KEY: misc_feature
<223> OTHER INFORMATION: Abies grandis geranyl pyrophosphate synthase
      nucleotide sequence ("AgGPPS2") - codon optimized for S.
      cerevisiae

<400> SEQUENCE: 8
atgttcgatt tcaacaaata catggattct aaggcgatga ccgttaatga agcactaaat     60
```

```
aaagccattc ccctgaggta tccccaaaaa atatacgagt ctatgaggta cagtttgttg    120
gcaggtggaa aacgagtaag accagtacta tgcatcgcag cctgtgaatt ggtcggtggt    180
actgaagaat tagcaattcc gactgcttgt gccattgaaa tgattcacac tatgtccctc    240
atgcatgacg acttgccttg catagataat gatgatctga aagaggtaa acctactaac     300 cataaaatct ttggagaaga tactgcagta acggctggaa atgctctcca cagctacgca    360
ttcgaacaca tcgcggtcag tacatctaaa acagtcgggg cagacagaat cttgaggatg    420
gtgtcagaac ttggtagggc aacaggttca gaaggagtga tgggtggcca aatggtcgat    480
atcgccagcg aaggggatcc tagcattgat ttgcaaacct tggaatggat ccatatccat    540
aagactgcta tgttattgga atgcagcgta gtttgtggtg ctatcattgg tggtgctagc    600
gaaatcgtta ttgaacgcgc aaggaggtat gcaaggtgtg ttggtctctt gtttcaagtt    660
gttgacgata tattggacgt taccaagtcc agcgatgaat tagggaaaac tgcaggcaag    720
gatcttattt cagataaggc tacttacccc aagctgatgg ggcttgaaaa agcaaaagag    780
ttcagtgatg aattattgaa tagagcaaag ggtgagctca gctgctttga ccctgtaaag    840
gctgcaccat tattagggtt agctgattat gtagctttta gacagaatta a             891
```

```
<210> SEQ ID NO 9
<211> LENGTH: 29
<212> TYPE: DNA
<213> ORGANISM: Artificial Sequence
<220> FEATURE:
<223> OTHER INFORMATION: Synthetic: Primer 213-IF

<400> SEQUENCE: 9
tggttcttag atgcttatgc tagcagacc                                       29

<210> SEQ ID NO 10
<211> LENGTH: 53
<212> TYPE: DNA
<213> ORGANISM: Artificial Sequence
<220> FEATURE:
<223> OTHER INFORMATION: Synthetic: Primer 213-IR
<220> FEATURE:
<221> NAME/KEY: misc_feature
<222> LOCATION: (32)..(32)
<223> OTHER INFORMATION: n is a, c, g, or t

<400> SEQUENCE: 10
ggtctgctag cataagcatc taagaaccaa hnggcctcca gcctttgaat ccg            53

<210> SEQ ID NO 11
<211> LENGTH: 53
<212> TYPE: DNA
<213> ORGANISM: Artificial Sequence
<220> FEATURE:
<223> OTHER INFORMATION: Synthetic: Primer 381-IF
<220> FEATURE:
<221> NAME/KEY: misc_feature
<222> LOCATION: (27)..(27)
<223> OTHER INFORMATION: n is a, c, g, or t

<400> SEQUENCE: 11
cgtggctgga tttggttgaa gcatatndtg ttgaggcaaa gtggttccac gat            53

<210> SEQ ID NO 12
<211> LENGTH: 26
<212> TYPE: DNA
<213> ORGANISM: Artificial Sequence
<220> FEATURE:
```

```
<223> OTHER INFORMATION: Synthetic: Primer 381-IR

<400> SEQUENCE: 12
atatgcttca accaaatcca gccacg                                          26

<210> SEQ ID NO 13
<211> LENGTH: 60
<212> TYPE: DNA
<213> ORGANISM: Artificial Sequence
<220> FEATURE:
<223> OTHER INFORMATION: Synthetic: Primer 389-IF
<220> FEATURE:
<221> NAME/KEY: misc_feature
<222> LOCATION: (28)..(28)
<223> OTHER INFORMATION: n is a, c, g, or t

<400> SEQUENCE: 13
tattttgttg aggcaaagtg gttccacndt ggatatactc caactctaga agaatatctc     60

<210> SEQ ID NO 14
<211> LENGTH: 30
<212> TYPE: DNA
<213> ORGANISM: Artificial Sequence
<220> FEATURE:
<223> OTHER INFORMATION: Synthetic: Primer 389-IR

<400> SEQUENCE: 14
gtggaaccac tttgcctcaa caaaatatgc                                      30

<210> SEQ ID NO 15
<211> LENGTH: 60
<212> TYPE: DNA
<213> ORGANISM: Artificial Sequence
<220> FEATURE:
<223> OTHER INFORMATION: Synthetic: Primer 404-IF
<220> FEATURE:
<221> NAME/KEY: misc_feature
<222> LOCATION: (28)..(28)
<223> OTHER INFORMATION: n is a, c, g, or t

<400> SEQUENCE: 15
ctagaagaat atctcaacaa ttcgaagndt acaataattt gtcctgcaat agtctcagaa     60

<210> SEQ ID NO 16
<211> LENGTH: 30
<212> TYPE: DNA
<213> ORGANISM: Artificial Sequence
<220> FEATURE:
<223> OTHER INFORMATION: Synthetic: Primer 404-IR

<400> SEQUENCE: 16
cttcgaattg ttgagatatt cttctagagt                                      30

<210> SEQ ID NO 17
<211> LENGTH: 56
<212> TYPE: DNA
<213> ORGANISM: Artificial Sequence
<220> FEATURE:
<223> OTHER INFORMATION: Synthetic: Primer 439-IF
<220> FEATURE:
<221> NAME/KEY: misc_feature
<222> LOCATION: (31)..(31)
<223> OTHER INFORMATION: n is a, c, g, or t

<400> SEQUENCE: 17
gagagcatat acaaatatca tgacatcctt ndtctttccg gaatgcttgc aaggct         56
```

-continued

```
<210> SEQ ID NO 18
<211> LENGTH: 30
<212> TYPE: DNA
<213> ORGANISM: Artificial Sequence
<220> FEATURE:
<223> OTHER INFORMATION: Synthetic: Primer 439-IR

<400> SEQUENCE: 18
aaggatgtca tgatatttgt atatgctctc                               30

<210> SEQ ID NO 19
<211> LENGTH: 59
<212> TYPE: DNA
<213> ORGANISM: Artificial Sequence
<220> FEATURE:
<223> OTHER INFORMATION: Synthetic: Primer 528-IF
<220> FEATURE:
<221> NAME/KEY: misc_feature
<222> LOCATION: (31)..(31)
<223> OTHER INFORMATION: n is a, c, g, or t

<400> SEQUENCE: 19
ctcggaagag tggctaattt tgtgtatgtg ndtggagatg gttttggagt gcaacactc    59

<210> SEQ ID NO 20
<211> LENGTH: 30
<212> TYPE: DNA
<213> ORGANISM: Artificial Sequence
<220> FEATURE:
<223> OTHER INFORMATION: Synthetic: Primer 528-IR

<400> SEQUENCE: 20
cacatacaca aaattagcca ctcttccgag                               30

<210> SEQ ID NO 21
<211> LENGTH: 60
<212> TYPE: DNA
<213> ORGANISM: Artificial Sequence
<220> FEATURE:
<223> OTHER INFORMATION: Synthetic: Primer 543-IF
<220> FEATURE:
<221> NAME/KEY: misc_feature
<222> LOCATION: (28)..(28)
<223> OTHER INFORMATION: n is a, c, g, or t

<400> SEQUENCE: 21
gtgcaacact caaaaataca tcaacaandt gctgaattac tgttttaccc atatcagtaa   60

<210> SEQ ID NO 22
<211> LENGTH: 30
<212> TYPE: DNA
<213> ORGANISM: Artificial Sequence
<220> FEATURE:
<223> OTHER INFORMATION: Synthetic: Primer 543-IR

<400> SEQUENCE: 22
ttgttgatgt atttttgagt gttgcactcc                               30

<210> SEQ ID NO 23
<211> LENGTH: 50
<212> TYPE: DNA
<213> ORGANISM: Artificial Sequence
<220> FEATURE:
<223> OTHER INFORMATION: Synthetic: Primer 482-IF
<220> FEATURE:
<221> NAME/KEY: misc_feature
<222> LOCATION: (21)..(21)
<223> OTHER INFORMATION: n is a, c, g, or t
```

<400> SEQUENCE: 23
acgcctcaga ggaggaggca ndtgagcaca tcagatttct tatgcgggag                50

<210> SEQ ID NO 24
<211> LENGTH: 20
<212> TYPE: DNA
<213> ORGANISM: Artificial Sequence
<220> FEATURE:
<223> OTHER INFORMATION: Synthetic: Primer 482-IR

<400> SEQUENCE: 24
tgcctcctcc tctgaggcgt                                                 20

<210> SEQ ID NO 25
<211> LENGTH: 60
<212> TYPE: DNA
<213> ORGANISM: Artificial Sequence
<220> FEATURE:
<223> OTHER INFORMATION: Synthetic: Primer 552-IF
<220> FEATURE:
<221> NAME/KEY: misc_feature
<222> LOCATION: (30)..(30)
<223> OTHER INFORMATION: n is a, c, g, or t

<400> SEQUENCE: 25
aaatggctga attattgttt tacccatacn dttaagctag ctaagatccg ctctaaccga     60

<210> SEQ ID NO 26
<211> LENGTH: 30
<212> TYPE: DNA
<213> ORGANISM: Artificial Sequence
<220> FEATURE:
<223> OTHER INFORMATION: Synthetic: Primer 552-IR

<400> SEQUENCE: 26
gtatgggtaa aacaataatt cagccatttg                                      30

<210> SEQ ID NO 27
<211> LENGTH: 60
<212> TYPE: DNA
<213> ORGANISM: Artificial Sequence
<220> FEATURE:
<223> OTHER INFORMATION: Synthetic: Primer 544-IF
<220> FEATURE:
<221> NAME/KEY: misc_feature
<222> LOCATION: (28)..(28)
<223> OTHER INFORMATION: n is a, c, g, or t

<400> SEQUENCE: 27
ttcggtgtcc aacactctaa gattcacndt caaatggctg aattattgtt ttacccatac     60

<210> SEQ ID NO 28
<211> LENGTH: 30
<212> TYPE: DNA
<213> ORGANISM: Artificial Sequence
<220> FEATURE:
<223> OTHER INFORMATION: Synthetic: Primer 544-IR

<400> SEQUENCE: 28
gtgaatctta gagtgttgga caccgaaacc                                      30

<210> SEQ ID NO 29
<211> LENGTH: 59
<212> TYPE: DNA
<213> ORGANISM: Artificial Sequence
<220> FEATURE:
<223> OTHER INFORMATION: Synthetic: Primer AMN449

```
<400> SEQUENCE: 29
ctatacttta acgtcaagga gaaaaaacgg atccatggtc gaaccaagaa gatccggta      59

<210> SEQ ID NO 30
<211> LENGTH: 30
<212> TYPE: DNA
<213> ORGANISM: Artificial Sequence
<220> FEATURE:
<223> OTHER INFORMATION: Synthetic: Primer YY317

<400> SEQUENCE: 30
ataagcttca accaaatcca accaagactt                                      30

<210> SEQ ID NO 31
<211> LENGTH: 20
<212> TYPE: DNA
<213> ORGANISM: Artificial Sequence
<220> FEATURE:
<223> OTHER INFORMATION: Synthetic: Primer JW730

<400> SEQUENCE: 31
tactttaacg tcaaggagaa                                                 20

<210> SEQ ID NO 32
<211> LENGTH: 29
<212> TYPE: DNA
<213> ORGANISM: Artificial Sequence
<220> FEATURE:
<223> OTHER INFORMATION: Synthetic: Primer ATN009

<400> SEQUENCE: 32
ttcaggttgt ctaactcctt cctttttcgg                                      29

<210> SEQ ID NO 33
<211> LENGTH: 9863
<212> TYPE: DNA
<213> ORGANISM: Artificial Sequence
<220> FEATURE:
<223> OTHER INFORMATION: Synthetic: Plasmid pAM11613

<400> SEQUENCE: 33
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgataccccg     180
catggaatgg gataatatca caggaggtac tagactacct ttcatcctac ataaatagac     240
gcatataagt acgcatttaa gcataaacac gcactatgcc gttcttctca tgtatatata     300
tatacaggca acacgcagat ataggtgcga cgtgaacagt gagctgtatg tgcgcagctc     360
gcgttgcatt ttcggaagcg ctcgttttcg gaaacgcttt gaagttccta ttccgaagtt     420
cctattctct agaaagtata ggaacttcag agcgcttttg aaaaccaaaa gcgctctgaa     480
gacgcacttt caaaaaacca aaaacgcacc ggactgtaac gagctactaa aatattgcga     540
ataccgcttc cacaaacatt gctcaaaagt atctctttgc tatatatctc tgtgctatat     600
ccctatataa cctacccatc cacctttcgc tccttgaact tgcatctaaa ctcgacctct     660
acatttttta tgtttatctc tagtattact ctttagacaa aaaaattgta gtaagaacta     720
ttcatagagt gaatcgaaaa caatacgaaa atgtaaacat ttcctatacg tagtatatag     780
agacaaaata gaagaaaccg ttcataattt tctgaccaat gaagaatcat caacgctatc     840
```

```
actttctgtt cacaaagtat gcgcaatcca catcggtata gaatataatc ggggatgcct    900
ttatcttgaa aaaatgcacc cgcagcttcg ctagtaatca gtaaacgcgg gaagtggagt    960
caggcttttt ttatggaaga gaaaatagac accaaagtag ccttcttcta accttaacgg   1020
acctacagtg caaaaagtta tcaagagact gcattataga gcgcacaaag gagaaaaaaa   1080
gtaatctaag atgctttgtt agaaaaatag cgctctcggg atgcattttt gtagaacaaa   1140
aaagaagtat agattctttg ttggtaaaat agcgctctcg cgttgcattt ctgttctgta   1200
aaaatgcagc tcagattctt tgtttgaaaa attagcgctc tcgcgttgca ttttgttttt   1260
acaaaaatga agcacagatt cttcgttggt aaaatagcgc tttcgcgttg catttctgtt   1320
ctgtaaaaat gcagctcaga ttcttttgttt gaaaaattag cgctctcgcg ttgcattttt   1380
gttctacaaa atgaagcaca gatgcttcgt tcaggtggca cttttcgggg aaatgtgcgc   1440
ggaacccta tttgtttatt tttctaaata cattcaaata tgtatccgct catgagacaa   1500
taaccctgat aaatgcttca ataatattga aaaaggaaga gtatgagtat tcaacatttc   1560
cgtgtcgccc ttattccctt ttttgcggca ttttgccttc ctgttttgc tcacccagaa   1620
acgctggtga agtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg gaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcatttttaa   2460
tttaaaagga tctaggtgaa gatcctttt gataatctca tgaccaaaat cccttaacgt   2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
gtttgtttgc cggatcaaga gctaccaact cttttccga aggtaactgg cttcagcaga   2700
gcgcagatac caaatactgt ccttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacgggggg ttcgtgcaca cagcccagct tggagcgaac gacctacacc   2940
gaactgagat acctacagcg tgagctatga gaaagcgcca cgcttcccga agggagaaag   3000
gcggacaggt atccggtaag cggcagggtc ggaacaggag agcgcacgag ggagcttcca   3060
gggggaaacg cctggtatct ttatagtcct gtcgggtttc gccacctctg acttgagcgt   3120
cgatttttgt gatgctcgtc aggggggcgg agcctatgga aaaacgccag caacgcggcc   3180
ttttacggt tcctggcctt tgctggcct tttgctcaca tgttctttcc tgcgttatcc   3240
```

```
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggatcttcga gcgtcccaaa    3420
accttctcaa gcaaggtttt cagtataatg ttacatgcgt acacgcgtct gtacagaaaa    3480
aaaagaaaaa tttgaaatat aaataacgtt cttaatacta acataactat aaaaaaataa    3540
atagggacct agacttcagg ttgtctaact ccttcctttt cggttagagc ggatcttagc    3600
tagcttattc aactaattct atagatgata aaaatggttt ctggacctct ttgacgtcct    3660
ttgatcttac gttagctaac tgggcgactg gtggataggc ccactcagaa ggtgaaacgg    3720
ctcctacatt ggcagcttgc tcgtagaact tgcaaaattt tgggcatcc tcagtctttt     3780 cctccttgac tttctcgtag atttcagaca acctgtacct cctgtcgcat aaatgccatg    3840
tgacataacc atgcatgaag cactctatgg tgtccattac ttgagggtcc ttgtctgaga    3900
aaactgcaac catttgcttt gaagagtgca aggtatcctg ggtcaattt tctaaggcct     3960 cgtgtaatga tatctcgtca gaaacaacgt agttctttac caaagagatc tgatccctct    4020
cgtcgtcgaa ctccttgtaa aatgacatca aatcattaac ccagaccatc caattttcca    4080
tttgagctat ggctgaagtg atctccaaaa acaatgatct ttcattgaac tgctcctttg    4140
gccacaaaga ggcaccgacg cagtgtccta aaccgttcat tcttctcaag aactgtgggt    4200
agtcgtgaga acctgggaat cctccaaaat tgtattgttc tatccagcaa ccctcgaaga    4260
agtctaaggt agacctgatc aagttcaatg agcaaaaagg accaaaatgc ctcaatacgt    4320
ttggaaagtg ctcgtttact aaagcccacc aaggatgagc ctgttctcta cctgcttgta    4380
agtcatcgaa gtagtttacc atagtagggt atgggtcgtc ttttgaatcg tccaatacca    4440
aggtgtaggt atagtggatt gacaagtctg ccatacactc tttagatacc ttggcccatg    4500
aatatacaac cataccgaca atggtctgca atgaagcttg caatctctta gggtcgacct    4560
tcaacaactg ctgctgtctt ggctgggcga agtggtgggc ggctttgttg taggcgtagt    4620
gtaagttctc aatcctctcc tccctggtat agtttgagtc cctgtaccta atgtactcca    4680
acaacctgac ggtggtgttc aagaagtact cggttggaaa gttttccatg gatccggggt    4740
tttttctcct tgacgttaaa gtatagaggt atattaacaa ttttttgttg atactttat    4800 tacatttgaa taagaagtaa tacaaaccga aaatgttgaa agtattagtt aaagtggtta    4860
tgcagttttt gcatttatat atctgttaat agatcaaaaa tcatcgcttc gctgattaat    4920 tacccccagaa ataaggctaa aaaactaatc gcattatcat cctatggttg ttaatttgat   4980 tcgttcatt gaaggtttgt ggggccaggt tactgccaat ttttcctctt cataaccata    5040
aaagctagta ttgtagaatc tttattgttc ggagcagtgc ggcgcgaggc acatctgcgt    5100
ttcaggaacg cgaccggtga agacgaggac gcacggagga gagtcttcct tcggagggct    5160
gtcacccgct cggcggcttc taatccgtac ttcaatatag caatgagcag ttaagcgtat    5220
tactgaaagt tccaaagaga aggtttttt aggctaagat aatggggctc tttacatttc     5280
cacaacatat aagtaagatt agatatggat atgtatatgg atatgtatat ggtggtaatg    5340
ccatgtaata tgattattaa acttctttgc gtccatccaa aaaaaagta agaattttg      5400 aaaattcgaa ttcatgaatt taactgtgga cagaagatct gctaattatc aaccaagcat    5460
ctgggatcac gattttctac aatcacttaa cagtaattat acggatgaag cctataagag    5520
gagggccgaa gaattgagag gaaaagttaa aatcgctatt aaagatgtta ttgaacctct    5580
```

```
cgaccagctt gagttaatag acaatctcca aagacttggc ttagcccata gatttgaaac      5640
agaaatcaga atatactta ataatattta taacaataac aaggattaca actggaggaa      5700
agaaaatttg tacgcaacat ctctcgaatt tagattgtta cgtcaacacg gatatccagt      5760
gagccaggaa gtgttcaacg gttttaaaga tgatcaaggt ggatttattt gtgatgattt      5820
taagggtatt ttaagtttgc atgaagcttc gtattactcc ttggaggggg aatcgattat      5880
ggaggaagcc tggcaattca cgagcaagca tctaaaagaa gtaatgattt ctaaaaatat      5940
ggaagaggat gttttcgtag ctgaacaagc aaagcgagct ctggaattac ccttacattg      6000
gaaagtacct atgttggagg cacgatggtt tatacacata tacgagcgtc gggaggacaa      6060
aaaccatcta cttttagagt tggcgaaaat ggaattcaat acactccagg caatttacca      6120
ggaggaattg aaggagatta gcggttggtg gaaggatact ggtctgggtg aaaaattgtc      6180
gttcgcacgt aatcgtttag ttgctagttt cctttggagc atggggatag cattcgaacc      6240
ccaatttgcc tattgtcgcc gtgtattaac gattagtatc gccttaatca ctgtgataga      6300
cgacatctac gatgtatacg gtacactaga tgaattagag atttttactg atgcggtcga      6360
gagatgggat atcaactatg cattaaagca cttgcctggc tacatgaaaa tgtgtttctt      6420
agcattatac aactttgtga atgaattcgc ttactatgtt cttaaacaac aggacttcga      6480
tctattgttg tctataaaaa acgcatggct cgggttaatt caagcatatc ttgttgaggc      6540
aaaatggtat cattctaagt ataccccaaa attggaagag tatctagaaa acggtcttgt      6600
gagtattacg ggacctttaa ttattactat tagctatctg tcaggaacta accctataat      6660
taaaaaggaa ttagaatttc ttgaaagcaa tcctgatatt gtccattgga gtagtaaaat      6720
ctttagatta caggacgatt tgggtacaag tagcgatgag attcaaagag gagacgtacc      6780
caaatctatc caatgttata tgcacgaaac cggtgctagt gaagaagtag ccagacaaca      6840
tataaaagac atgatgagac agatgtggaa aaaagtaaat gcttacacag ctgataaaga      6900
ttctcctctt acgggaacca ctacagagtt cctgttaaac ctagttagaa tgagtcattt      6960
catgtactta cacggagatg gccacggtgt ccaaaatcaa gaaactatcg atgtggggtt      7020
cacgttgttg tttcaaccga tacctttaga ggataagcat atggcattta cagcgtcacc      7080
tggtacaaaa ggctaagcga atttcttatg atttatgatt tttattatta aataagttat      7140
aaaaaaaata agtgtataca aattttaaag tgactcttag gttttaaaac gaaaattctt      7200
attcttgagt aactctttcc tgtaggtcag gttgctttct caggtatagc atgaggtcgc      7260
tccaattcag ctggcgtaat agcgaagagg cccgcaccga tcgcccttcc caacagttgc      7320
gcagcctgaa tggcgaatgg cgcgacgcgc cctgtagcgg cgcattaagc gcggcgggtg      7380
tggtggttac gcgcagcgtg accgctacac ttgccagcgc cctagcgccc gctcctttcg      7440
ctttcttccc ttcctttctc gccacgttcg ccggctttcc ccgtcaagct ctaaatcggg      7500
ggctcccttt agggttccga tttagtgctt tacggcacct cgaccccaaa aaacttgatt      7560
agggtgatgg ttcacgtagt gggccatcgc cctgatagac ggtttttcgc cctttgacgt      7620
tggagtccac gttctttaat agtggactct tgttccaaac tggaacaaca ctcaacccta      7680
tctcggtcta ttcttttgat ttataaggga ttttgccgat ttcggcctat tggttaaaaa      7740
atgagctgat ttaacaaaaa tttaacgcga attttaacaa aatattaacg tttacaattt      7800
cctgatgcgg tattttctcc ttacgcatct gtgcggtatt tcacaccgca tatcgacggt      7860
cgaggagaac ttctagtata tccacatacc taatattatt gccttattaa aaatggaatc      7920
ccaacaatta catcaaaatc cacattctct tcaaaatcaa ttgtcctgta cttccttgtt      7980
```

```
catgtgtgtt caaaaacgtt atatttatag gataattata ctctatttct caacaagtaa   8040
ttggttgttt ggccgagcgg tctaaggcgc cttttttttat atatatttca aggatatacc   8100
attgtaatgt ctgccctaa gaagatcgtc gttttgccag gtgaccacgt tggtcaagaa   8160
atcacagccg aagccattaa ggttcttaaa gctatttctg atgttcgttc caatgtcaag   8220
ttcgatttcg aaaatcattt aattggtggt gctgctatcg atgctacagg tgttccactt   8280
ccagatgagg cgctggaagc ctccaagaag gttgatgccg ttttgttagg tgctgtggct   8340
ggtcctaaat ggggtaccgg tagtgttaga cctgaacaag gtttactaaa aatccgtaaa   8400
gaacttcaat tgtacgccaa cttaagacca tgtaactttg catccgactc tcttttagac   8460
ttatctccaa tcaagccaca atttgctaaa ggtactgact tcgttgttgt cagagaatta   8520
gtgggaggta tttactttgg taagagaaag gaagacgatg gtgatggtgt cgcttgggat   8580
agtgaacaat acaccgttcc agaagtgcaa agaatcacaa gaatggccgc tttcatggcc   8640
ctacaacatg agccaccatt gcctatttgg tccttggata agctaatcct tttggcctct   8700
tcaagattat ggagaaaaac tgtggaggaa accatcaaga acgaattccc tacattgaag   8760
gttcaacatc aattgattga ttctgccgcc atgatcctag ttaagaaccc aacccaccta   8820
aatggtatta taatcaccag caacatgttt ggtgatatca tctccgatga agcctccgtt   8880
atcccaggtt ccttgggttt gttgccatct gcgtccttgg cctctttgcc agacaagaac   8940
accgcatttg gtttgtacga accatgccac ggttctgctc cagatttgcc aaagaataag   9000
gttgacccta tcgccactat cttgtctgct gcaatgatgt tgaaattgtc attgaacttg   9060
cctgaagaag gtaaggccat tgaagatgca gttaaaaagg ttttggatgc aggtatcaga   9120
actggtgatt taggtggttc caacagtacc accgaagtcg gtgatgctgt cgccgaagaa   9180
gttaagaaaa tccttgctta aaaagattct cttttttttat gatatttgta cataaacttt   9240
ataaatgaaa ttcataatag aaacgacacg aaattacaaa atggaatatg ttcatagggt   9300
agacgaaact atatacgcaa tctacataca tttatcaaga aggagaaaaa ggaggatagt   9360
aaaggaatac aggtaagcaa attgatacta atggctcaac gtgataagga aaagaattg   9420 cactttaaca ttaatattga caaggaggag ggcaccacac aaaaagttag gtgtaacaga   9480
aaatcatgaa actacgattc ctaatttgat attggaggat tttctctaaa aaaaaaaaa   9540 tacaacaaat aaaaaacact caatgacctg accatttgat ggagtttaag tcaataccct   9600
cttgaagcat ttcccataat ggtgaaagtt ccctcaagaa ttttactctg tcagaaacgg   9660
ccttacgacg tagtcgatat ggtgcactct cagtacaatc tgctctgatg ccgcatagtt   9720
aagccagccc cgacacccgc caacacccgc tgacgcgccc tgacgggctt gtctgctccc   9780
ggcatccgct tacagacaag ctgtgaccgt ctccgggagc tgcatgtgtc agaggttttc   9840
accgtcatca ccgaaacgcg cga                                           9863
```

<210> SEQ ID NO 34
<211> LENGTH: 9866
<212> TYPE: DNA
<213> ORGANISM: Artificial Sequence
<220> FEATURE:
<223> OTHER INFORMATION: Synthetic: Plasmid pAM11614

<400> SEQUENCE: 34

```
gacgaaaggg cctcgtgata cgcctatttt tataggttaa tgtcatgata ataatggttt     60
cttagtatga tccaatatca aaggaaatga tagcattgaa ggatgagact aatccaattg    120
```

```
aggagtggca gcatatagaa cagctaaagg gtagtgctga aggaagcata cgatacccg    180
catggaatgg gataatatca caggaggtac tagactacct ttcatcctac ataaatagac    240
gcatataagt acgcatttaa gcataaacac gcactatgcc gttcttctca tgtatatata    300
tatacaggca acacgcagat ataggtgcga cgtgaacagt gagctgtatg tgcgcagctc    360
gcgttgcatt ttcggaagcg ctcgttttcg gaaacgcttt gaagttccta ttccgaagtt    420
cctattctct agaaagtata ggaacttcag agcgcttttg aaaaccaaaa gcgctctgaa    480
gacgcacttt caaaaaacca aaaacgcacc ggactgtaac gagctactaa atattgcga    540
ataccgcttc cacaaacatt gctcaaaagt atctctttgc tatatatctc tgtgctatat    600
ccctatataa cctacccatc caccttccgc tccttgaact tgcatctaaa ctcgacctct    660
acattttta tgtttatctc tagtattact ctttagacaa aaaaattgta gtaagaacta    720
ttcatagagt gaatcgaaaa caatacgaaa atgtaaacat ttcctatacg tagtatatag    780
agacaaaata gaagaaaccg ttcataattt tctgaccaat gaagaatcat caacgctatc    840
actttctgtt cacaaagtat gcgcaatcca catcggtata gaatataatc ggggatgcct    900
ttatcttgaa aaaatgcacc cgcagcttcg ctagtaatca gtaaacgcgg gaagtggagt    960
caggcttttt ttatggaaga gaaaatagac accaaagtag ccttcttcta accttaacgg   1020
acctacagtg caaaagtta tcaagagact gcattataga gcgcacaaag gagaaaaaaa   1080
gtaatctaag atgctttgtt agaaaaatag cgctctcggg atgcatttt gtagaacaaa   1140
aaagaagtat agattctttg ttggtaaaat agcgctctcg cgttgcattt ctgttctgta   1200
aaaatgcagc tcagattctt tgtttgaaaa attagcgctc tcgcgttgca ttttgttt    1260
acaaaatga agcacagatt cttcgttggt aaaatagcgc tttcgcgttg catttctgtt   1320
ctgtaaaat gcagctcaga ttctttgttt gaaaaattag cgctctcgcg ttgcatttt    1380
gttctacaaa atgaagcaca gatgcttcgt tcaggtggca cttttcgggg aaatgtgcgc   1440
ggaacccta tttgttattt tttctaaata cattcaaata tgtatccgct catgagacaa   1500
taaccctgat aaatgcttca ataatattga aaaggaaga gtatgagtat tcaacatttc   1560
cgtgtcgccc ttattccctt ttttgcggca ttttgcttc ctgttttgc tcacccagaa   1620
acgctggtga agtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcatttttaa   2460
tttaaaagga tctaggtgaa gatccttttt gataatctca tgaccaaaat cccttaacgt   2520
```

```
gagttttcgt tccactgagc gtcagacccc gtagaaaaga tcaaaggatc ttcttgagat      2580
ccttttttc tgcgcgtaat ctgctgcttg caaacaaaaa aaccaccgct accagcggtg      2640
gtttgtttgc cggatcaaga gctaccaact cttttttccga aggtaactgg cttcagcaga    2700
gcgcagatac caaatactgt ccttctagtg tagccgtagt taggccacca cttcaagaac    2760
tctgtagcac cgcctacata cctcgctctg ctaatcctgt taccagtggc tgctgccagt    2820
ggcgataagt cgtgtcttac cgggttggac tcaagacgat agttaccgga taaggcgcag    2880
cggtcgggct gaacggggg ttcgtgcaca cagcccagct tggagcgaac gacctacacc      2940
gaactgagat acctcagcg tgagctatga gaaagcgcca cgcttcccga agggagaaag      3000
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgatttttgt gatgctcgtc aggggggcgg agcctatgga aaaacgccag caacgcggcc    3180
tttttacggt tcctggcctt tgctggcct tttgctcaca tgttctttcc tgcgttatcc      3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggatcttcga gcgtcccaaa    3420
accttctcaa gcaaggtttt cagtataatg ttacatgcgt acacgcgtct gtacagaaaa    3480
aaagaaaaa tttgaaatat aataacgtt cttaatacta acataactat aaaaaaataa       3540
atagggacct agacttcagg ttgtctaact ccttcctttt cggttagagc ggatcttagc    3600
tagcttattc aactaattct atagatgata aaaatggttt ctggacctct ttgacgtcct    3660
ttgatcttac gttagctaac tgggcgactg gtggataggc ccactcagaa ggtgaaacgg    3720
ctcctacatt ggcagcttgc tcgtagaact tgcaaaattt ttgggcatcc tcagtctttt    3780
cctccttgac tttctcgtag atttcagaca acctgtacct cctgtcgcat aaatgccatg    3840
tgacataacc atgcatgaag cactctatgg tgtccattac ttgagggtcc ttgtctgaga    3900
aaactgcaac catttgcttt gaagagtgca aggtatcctg ggtcaatttt tctaaggcct    3960
cgtgtaatga tatctcgtca gaaacaacgt agttctttac caaagagatc tgatccctct    4020
cgtcgtcgaa ctccttgtaa aatgacatca aatcattaac ccagaccatc caattttcca    4080
tttgagctat ggctgaagtg atctccaaaa acaatgatct ttcattgaac tgctcctttg    4140
gccacaaaga ggcaccgacg cagtgtccta aaccgttcat tcttctcaag aactgtgggt    4200
agtcgtgaga acctgggaat cctccaaaat tgtattgttc tatccagcaa ccctcgaaga    4260
agtctaaggt agacctgatc aagttcaatg agcaaaaagg accaaaatgc ctcaatacgt    4320
ttggaaagtg ctcgtttact aaagcccacc aaggatgagc ctgttctcta cctgcttgta    4380
agtcatcgaa gtagtttacc atagtagggt atgggtcgtc ttttgaatcg tccaatacca    4440
aggtgtaggt atagtggatt gacaagtctg ccatacactc tttagatacc ttggcccatg    4500
aatatacaac cataccgaca atggtctgca atgaagcttg caatctctta gggtcgacct    4560
tcaacaactg ctgctgtctt ggctgggcga agtggtgggc ggctttgttg taggcgtagt    4620
gtaagttctc aatcctctcc tccctggtat agtttgagtc cctgtaccta atgtactcca    4680
acaacctgac ggtggtgttc aagaagtact cggttggaaa gttttccatg gatccggggt    4740
ttttctcct tgacgttaaa gtatagaggt atattaacaa ttttttgttg atacttttat      4800
tacatttgaa taagaagtaa tacaaaccga aaatgttgaa agtattagtt aaagtggtta    4860
```

```
tgcagttttt gcatttatat atctgttaat agatcaaaaa tcatcgcttc gctgattaat    4920
tacccagaa ataaggctaa aaaactaatc gcattatcat cctatggttg ttaatttgat     4980
tcgttcattt gaaggtttgt ggggccaggt tactgccaat ttttcctctt cataaccata    5040
aaagctagta ttgtagaatc tttattgttc ggagcagtgc ggcgcgaggc acatctgcgt    5100
ttcaggaacg cgaccggtga agacgaggac gcacggagga gagtcttcct tcggagggct    5160
gtcacccgct cggcggcttc taatccgtac ttcaatatag caatgagcag ttaagcgtat    5220
tactgaaagt tccaaagaga aggttttttt aggctaagat aatggggctc tttacatttc    5280
cacaacatat aagtaagatt agatatggat atgtatatgg atatgtatat ggtggtaatg    5340
ccatgtaata tgattattaa acttctttgc gtccatccaa aaaaaaagta agaattttg     5400
aaaattcgaa ttcatggata acttaactgt tgacagaaga tctgccaact accaaccatc    5460
tatctgggat catgatttct tacaatcctt gaactccaac tacactgatg aagcttataa    5520
gagaagagct gaagaattaa gaggtaaggt caagattgct atcaaggatg tcattgaacc    5580
attggaccaa ttggaattga tcgataactt gcaacgtttg ggtttggctc atagattcga    5640
gaccgaaatt cgtaacatct taaacaacat ttacaacaac acaaggatt acaactggag     5700
aaaggaaaac ttatatgcta cctccttgga attcagatta ttaagacaac atggttaccc    5760
agtctctcaa gaagttttca atggtttcaa ggatgatcaa ggtggtttca tttgtgatga    5820
ctttaagggt atcttatctt tgcatgaagc ttcctattac tccttggaag gtgagtctat    5880
tatggaagaa gcctggcaat ttacctctaa gcacttgaag gaagtcatga tttctaaaaa    5940
catgaagaa gatgttttcg ttgctgaaca agctaagcgt gctttggaat taccattgca     6000
ctggaaggtt ccaatgttgg aagcccgttg gttattcac atctacgaaa gaagagaaga     6060
caagaatcac ttgttgttgg aattggccaa gatggaattc aacactttac aagctattta    6120
ccaagaggaa ttgaaggaga tctctggttg gtggaaagac actggtttag gtgaaaagtt    6180
atctttgct agaaacagat tagtcgcttc cttcttatgg tctatgggta ttgctttcga    6240
gccacaattc gcttattgta gacgtgtctt gaccatttcc atcgctttga ttactgttat    6300
tgatgatatt tacgatgttt acggtacctt ggatgaatta gaaattttca ccgacgctgt    6360
tgagagatgg gacatcaact acgccttgaa gcatttgcca ggttatatga agatgtgttt    6420
cttagctttg tataatttcg ttaatgaatt cgcctattac gttttgaagc aacaagactt    6480
cgacttgtta ttatccatta agaacgcttg gttaggtttg attcaagctt atttggtcga    6540
agccaagtgg taccactcca gtataccccc aaagttggaa gagtacttgg aaaacggttt    6600
agtttctatc actggtccat tgatcattac tatctcttac ttatctggta ccaacccaat    6660
tattaagaag gaattggaat ttttggaatc taacccagat attgttcact ggtcttctaa    6720
gattttcaga ttgcaagatg acttgggtac ttcctctgat gaaattcaaa gaggtgacgt    6780
cccaaagtcc atccaatgtt acatgcatga aactggtgct tctgaagagg tcgccagaca    6840
acacattaag gatatgatgc gtcaaatgtg gaagaaggtc aacgcctaca ccgccgacaa    6900
agattctcca ttgactggta ccactactga atttttgttg aacttagtta gaatgtctca    6960
tttcatgtac ttgcatggtg acggtcacgg tgtccaaaac caagaaacta tcgacgtcgg    7020
ttttactttg ttgttccaac caattccatt ggaagataaa catatggctt tcactgcctc    7080
tccaggtact aagggttaag cgaatttctt atgatttatg attttttatta ttaaataagt   7140
tataaaaaaa ataagtgtat acaaattta aagtgactct taggttttaa aacgaaaatt     7200
cttattcttg agtaactctt tcctgtaggt caggttgctt tctcaggtat agcatgaggt    7260
```

```
cgctccaatt cagctggcgt aatagcgaag aggcccgcac cgatcgccct tcccaacagt   7320
tgcgcagcct gaatggcgaa tggcgcgacg cgccctgtag cggcgcatta agcgcggcgg   7380
gtgtggtggt tacgcgcagc gtgaccgcta cacttgccag cgccctagcg cccgctcctt   7440
tcgctttctt cccttccttt ctcgccacgt tcgccggctt tccccgtcaa gctctaaatc   7500
gggggctccc tttagggttc cgatttagtg ctttacggca cctcgacccc aaaaaacttg   7560
attagggtga tggttcacgt agtgggccat cgccctgata cacggttttt cgcccttga    7620 cgttggagtc cacgttcttt aatagtggac tcttgttcca aactggaaca acactcaacc   7680
ctatctcggt ctattctttt gatttataag ggattttgcc gatttcggcc tattggttaa   7740
aaaatgagct gatttaacaa aaatttaacg cgaattttaa caaaatatta cgtttacaa    7800 tttcctgatg cggtattttc tccttacgca tctgtgcggt atttcacacc gcatatcgac   7860
ggtcgaggag aacttctagt atatccacat acctaatatt attgccttat aaaaatgga    7920 atcccaacaa ttacatcaaa atccacattc tcttcaaaat caattgtcct gtacttcctt   7980
gttcatgtgt gttcaaaaac gttatattta taggataatt atactctatt tctcaacaag   8040
taattggttt tttggccgag cggtctaagg cgcctttttt tatatatatt tcaaggatat   8100
accattgtaa tgtctgcccc taagaagatc gtcgttttgc caggtgacca cgttggtcaa   8160
gaaatcacag ccgaagccat taaggttctt aaagctattt ctgatgttcg ttccaatgtc   8220
aagttcgatt tcgaaaatca tttaattggt ggtgctgcta tcgatgctac aggtgttcca   8280
cttccagatg aggcgctgga agcctccaag aaggttgatg ccgttttgtt aggtgctgtg   8340
gctggtccta aatggggtac cggtagtgtt agacctgaac aaggtttact aaaaatccgt   8400
aaagaacttc aattgtacgc caacttaaga ccatgtaact ttgcatccga ctctctttta   8460
gacttatctc caatcaagcc acaatttgct aaaggtactg acttcgttgt tgtcagagaa   8520
ttagtgggag gtatttactt tggtaagaga aggaagacg atggtgatgg tgtcgcttgg   8580
gatagtgaac aatacaccgt tccagaagtg caaagaatca caagaatggc cgctttcatg   8640
gccctacaac atgagccacc attgccatt tggtccttgg ataaagctaa tctttggcc    8700 tcttcaagat tatggagaaa aactgtggag gaaaccatca agaacgaatt ccctacattg   8760
aaggttcaac atcaattgat tgattctgcc gccatgatcc tagttaagaa cccaacccac   8820
ctaaatggta ttataatcac cagcaacatg tttggtgata tcatctccga tgaagcctcc   8880
gttatcccag gttccttggg tttgttgcca tctgcgtcct tggcctcttt gccagacaag   8940
aacaccgcat ttggtttgta cgaaccatgc cacggttctg ctccagattt gccaaagaat   9000
aaggttgacc ctatcgccac tatcttgtct gctgcaatga tgttgaaatt gtcattgaac   9060
ttgcctgaag aaggtaaggc cattgaagat gcagttaaaa aggttttgga tgcaggtatc   9120
agaactggtg atttaggtgg ttccaacagt accaccgaag tcggtgatgc tgtcgccgaa   9180
gaagttaaga aaatccttgc ttaaaaagat tctctttttt tatgatattt gtacataaac   9240
tttataaatg aaattcataa tagaaacgac acgaaattac aaaatggaat atgttcatag   9300
ggtagacgaa actatatacg caatctacat acatttatca agaaggagaa aaaggaggat   9360
agtaaaggaa tacaggtaag caaattgata ctaatggctc aacgtgataa ggaaaaagaa   9420
ttgcacttta acattaatat tgacaaggag gagggcacca cacaaaaagt taggtgtaac   9480
agaaaatcat gaaactacga ttcctaattt gatattggag gattttctct aaaaaaaaaa   9540
aaatacaaca aataaaaaac actcaatgac ctgaccattt gatggagttt aagtcaatac   9600
```

-continued

| | |
|---|---|
| cttcttgaag catttcccat aatggtgaaa gttccctcaa gaattttact ctgtcagaaa | 9660 |
| cggccttacg acgtagtcga tatggtgcac tctcagtaca atctgctctg atgccgcata | 9720 |
| gttaagccag ccccgacacc cgccaacacc cgctgacgcg ccctgacggg cttgtctgct | 9780 |
| cccggcatcc gcttacagac aagctgtgac cgtctccggg agctgcatgt gtcagaggtt | 9840 |
| ttcaccgtca tcaccgaaac gcgcga | 9866 |

<210> SEQ ID NO 35
<211> LENGTH: 6764
<212> TYPE: DNA
<213> ORGANISM: Artificial Sequence
<220> FEATURE:
<223> OTHER INFORMATION: Synthetic: Plasmid pAM2947

<400> SEQUENCE: 35

| | |
|---|---|
| acagcttgtc tgtaagcgga tgccgggagc agacaagccc gtcagggcgc gtcagcgggt | 60 |
| gttggcgggt gtcggggctg gcttaactat gcggcatcag agcagattgt actgagagtg | 120 |
| caaatacaca tcatcgtcct acaagttcat caaagtgttg acagacaac tataccagca | 180 |
| tggatctctt gtatcggttc tttttctcccg ctctctcgca ataacaatga acactgggtc | 240 |
| aatcatagcc tacacaggtg aacagagtag cgtttataca gggtttatac ggtgattcct | 300 |
| acggcaaaaa ttttcatttt ctaaaaaaaa aagaaaaat ttttctttcc aacgctagaa | 360 |
| ggaaagaaa atctaatta aattgatttg gtgattttct gagagttccc ttttcatat | 420 |
| atcgaatttt gaatataaaa ggagatcgaa aaattttttc tattcaatct gttttctggt | 480 |
| tttatttgat agtttttttg tgtattatta ttatggatta gtactggttt atatgggttt | 540 |
| ttctgtataa cttcttttta ttttagtttg tttaatctta ttttgagtta cattatagtt | 600 |
| ccctaactgc aagagaagta acattaaaaa tgggtaagga aaagactcac gtttcgaggc | 660 |
| cgcgattaaa ttccaacatg gatgctgatt tatatgggta taaatgggct cgcgataatg | 720 |
| tcgggcaatc aggtgcgaca atctatcgat tgtatgggaa gcccgatgcg ccagagttgt | 780 |
| ttctgaaaca tggcaaaggt agcgttgcca atgatgttac agatgagatg gtcagactaa | 840 |
| actggctgac ggaatttatg cctcttccga ccatcaagca ttttatccgt actcctgatg | 900 |
| atgcatggtt actcaccact gcgatccccg gcaaaacagc attccaggta ttagaagaat | 960 |
| atcctgattc aggtgaaaat attgttgatg cgctggcagt gttcctgcgc cggttgcatt | 1020 |
| cgattcctgt ttgtaattgt ccttttaaca gcgatcgcgt atttcgtctc gctcaggcgc | 1080 |
| aatcacgaat gaataacggt ttggttgatg cgagtgattt tgatgacgag cgtaatggct | 1140 |
| ggcctgttga acaagtctgg aaagaaatgc ataagctttt gccattctca ccggattcag | 1200 |
| tcgtcactca tggtgatttc tcacttgata accttatttt tgacgagggg aaattaatag | 1260 |
| gttgtattga tgttggacga gtcggaatcg cagaccgata ccaggatctt gccatcctat | 1320 |
| ggaactgcct cggtgagttt tctccttcat tacagaaacg ctttttcaa aaatatggta | 1380 |
| ttgataatcc tgatatgaat aaattgcagt ttcatttgat gctcgatgag ttttctaag | 1440 |
| tttaacttga tactactaga ttttttctct tcatttataa aattttttggt tataattgaa | 1500 |
| gctttagaag tatgaaaaaa tccttttttt tcattctttg caaccaaaat aagaagcttc | 1560 |
| ttttattcat tgaaatgatg aatataaacc taacaaaaga aaaagactcg aatatcaaac | 1620 |
| attaaaaaaa aataaaagag gttatctgtt ttcccattta gttggagttt gcattttcta | 1680 |
| atagataaa ctctcaatta atgtggattt agtttctctg ttcgtttttt tttgttttgt | 1740 |
| tctcactgta tttacatttc tatttagtat ttagttattc atataatctt aacttgcggt | 1800 |

```
gtgaaatacc gcacagatgc gtaaggagaa aataccgcat caggaaattg taagcgttaa    1860
tattttgtta aaattcgcgt taaatttttg ttaaatcagc tcatttttta accaataggc    1920
cgaaatcggc aaaatccctt ataaatcaaa agaatagacc gagatagggt tgagtgttgt    1980
tccagtttgg aacaagagtc cactattaaa gaacgtggac tccaacgtca aagggcgaaa    2040
aaccgtctat cagggcgatg gcccactacg tgaaccatca ccctaatcaa gttttttggg    2100
gtcgaggtgc cgtaaagcac taaatcggaa ccctaaaggg agcccccgat ttagagcttg    2160
acggggaaag ccggcgaacg tggcgagaaa ggaagggaag aaagcgaaag gagcgggcgc    2220
tagggcgctg gcaagtgtag cggtcacgct gcgcgtaacc accacacccg ccgcgcttaa    2280
tgcgccgcta cagggcgcgt cgcgccattc gccattcagg ctgcgcaact gttgggaagg    2340
gcgatcggtg cgggcctctt cgctattacg ccagctggcg aaaggggat gtgctgcaag    2400 gcgattaagt tgggtaacgc cagggttttc ccagtcacga cgttgtaaaa cgacggccag    2460
tgagcgcgcg taatacgact cactataggg cggaataaaa aacacgcttt ttcagttcga    2520
gtttatcatt atcaatactg ccatttcaaa gaatacgtaa ataattaata gtagtgattt    2580
tcctaacttt atttagtcaa aaaattagcc ttttaattct gctgtaaccc gtacatgccc    2640 aaaataggggg gcgggttaca cagaatatat aacatcgtag gtgtctgggt gaacagttta    2700
ttcctggcat ccactaaata taatggagcc cgcttttaa gctggcatcc agaaaaaaaa    2760
agaatcccag caccaaaata ttgttttctt caccaaccat cagttcatag gtccattctc    2820
ttagcgcaac tacagagaac aggggcacaa acaggcaaaa aacgggcaca acctcaatgg    2880
agtgatgcaa cctgcctgga gtaaatgatg acacaaggca attgacccac gcatgtatct    2940
atctcatttt cttacacctt ctattacctt ctgctctctc tgatttggaa aaagctgaaa    3000
aaaaaggttg aaaccagttc cctgaaatta ttccctact tgactaataa gtatataaag    3060
acggtaggta ttgattgtaa ttctgtaaat ctatttctta aacttcttaa attctacttt    3120
tatagttagt cttttttta gttttaaaac accaagaact tagtttcgaa taaacacaca    3180
taaacaaaca aaatgactaa gttgtattct gacttgtaca ggacctgcat gacatgcgga    3240
gaagaaaaat tgtcaaccga gttctacgtc aggaacaaga agaccggagt tagacattca    3300
tcatgcaaag agtgtgacaa ggtcagggtc aaatcaagac acaaggagaa ccctgaaagg    3360
accaaaaaca acgacttgaa gagattgtac ggaatcaccct tggacgagca tacccaaatg    3420
tatgaggaac aaaatggtgt atgtgcaatt tgcaagggag aaggagatgg aaagtggaag    3480
aaattgtgtg ttgaccatga tcacgaaaca ggaaaggtca ggcagttgtt gtgtaggaac    3540
tgcaatatga tgtttgggtca ggtcaacgac aacgttaact tattatcaga aatgataaag    3600
tatttgaaaa gatatcagta aaacctgcag gccgcgagcg ccgattaagt gaatttactt    3660
taaatcttgc atttaaataa attttctttt tatagcttta tgacttagtt tcaatttata    3720
tactatttta atgacatttt cgattcattg attgaaagct ttgtgttttt tcttgatgcg    3780
ctattgcatt gttcttgtct ttttcgccac atgtaatatc tgtagtagat acctgataca    3840
ttgtggatgc tgagtgaaat tttagttaat aatggaggcg ctcttaataa ttttggggat    3900
attggcttaa cgcgatcgcc gacgccgccg atggggatc cactagttct agagcggccg    3960
ccaccgcggt ggagctccag cttttgttcc ctttagtgag ggttaattgc gcgcttggcg    4020
taatcatggt catagctgtt tcctgtgtga aattgttatc cgctcacaat tccacacaac    4080
ataggagccg gaagcataaa gtgtaaagcc tggggtgcct aatgagtgag gtaactcaca    4140
```

-continued

```
ttaattgcgt tgcgctcact gcccgctttc cagtcgggaa acctgtcgtg ccagctgcat    4200
taatgaatcg gccaacgcgc ggggagaggc ggtttgcgta ttgggcgctc ttccgcttcc    4260
tcgctcactg actcgctgcg ctcggtcgtt cggctgcggc gagcggtatc agctcactca    4320
aaggcggtaa tacggttatc cacagaatca ggggataacg caggaaagaa catgtgagca    4380
aaaggccagc aaaaggccag gaaccgtaaa aaggccgcgt tgctggcgtt tttccatagg    4440
ctccgccccc ctgacgagca tcacaaaaat cgacgctcaa gtcagaggtg gcgaaacccg    4500
acaggactat aaagatacca ggcgtttccc cctggaagct ccctcgtgcg ctctcctgtt    4560
ccgaccctgc cgcttaccgg atacctgtcc gcctttctcc cttcgggaag cgtggcgctt    4620
tctcatagct cacgctgtag gtatctcagt tcggtgtagg tcgttcgctc caagctgggc    4680
tgtgtgcacg aaccccccgt tcagcccgac cgctgcgcct tatccggtaa ctatcgtctt    4740
gagtccaacc cggtaagaca cgacttatcg ccactggcag cagccactgg taacaggatt    4800
agcagagcga ggtatgtagg cggtgctaca gagttcttga agtggtggcc taactacggc    4860
tacactagaa ggacagtatt tggtatctgc gctctgctga gccagttac cttcggaaaa    4920
agagttggta gctcttgatc cggcaaacaa accaccgctg gtagcggtgg tttttttgtt    4980
tgcaagcagc agattacgcg cagaaaaaaa ggatctcaag aagatccttt gatcttttct    5040
acggggtctg acgctcagtg gaacgaaaac tcacgttaag ggattttggt catgagatta    5100
tcaaaaagga tcttcaccta gatccttta aattaaaaat gaagttttaa atcaatctaa    5160
agtatatatg agtaaacttg gtctgacagt taccaatgct taatcagtga ggcacctatc    5220
tcagcgatct gtctatttcg ttcatccata gttgcctgac tccccgtcgt gtagataact    5280
acgatacggg agggcttacc atctggcccc agtgctgcaa tgataccgcg agacccacgc    5340
tcaccggctc cagatttatc agcaataaac cagccagccg aagggccga gcgcagaagt    5400
ggtcctgcaa ctttatccgc ctccatccag tctattaatt gttgccggga agctagagta    5460
agtagttcgc cagttaatag tttgcgcaac gttgttgcca ttgctacagg catcgtggtg    5520
tcacgctcgt cgtttggtat ggcttcattc agctccggtt cccaacgatc aaggcgagtt    5580
acatgatccc ccatgttgtg caaaaaagcg gttagctcct tcggtcctcc gatcgttgtc    5640
agaagtaagt tggccgcagt gttatcactc atggttatgg cagcactgca taattctctt    5700
actgtcatgc catccgtaag atgcttttct gtgactggtg agtactcaac caagtcattc    5760
tgagaatagt gtatgcggcg accgagttgc tcttgcccgg cgtcaatacg ggataatacc    5820
gcgccacata gcagaacttt aaaagtgctc atcattggaa acgttcttc ggggcgaaaa    5880
ctctcaagga tcttaccgct gttgagatcc agttcgatgt aacccactcg tgcacccaac    5940
tgatcttcag catcttttac tttcaccagc gtttctgggt gagcaaaaac aggaaggcaa    6000
aatgccgcaa aaaagggaat aagggcgaca cggaaatgtt gaatactcat actcttcctt    6060
tttcaatatt attgaagcat ttatcagggt tattgtctca tgagcggata catatttgaa    6120
tgtatttaga aaaataaaca aataggggtt ccgcgcacat ttccccgaaa agtgccacct    6180
gggtcctttt catcacgtgc tataaaaata attataattt aaattttta atataaatat    6240
ataaattaaa aatagaaagt aaaaaaagaa attaagaaa aaatagtttt tgttttccga    6300
agatgtaaaa gactctaggg ggatcgccaa caaatactac cttttatctt gctcttcctg    6360
ctctcaggta ttaatgccga attgtttcat cttgtctgtg tagaagacca cacacgaaaa    6420
tcctgtgatt ttacatttta cttatcgtta atcgaatgta tatctattta atctgctttt    6480
cttgtctaat aaatatatat gtaaagtacg ctttttgttg aaatttttta aacctttgtt    6540
```

-continued

| | |
|---|---|
| tatttttttt tcttcattcc gtaactcttc taccttcttt atttactttc taaaatccaa | 6600 |
| atacaaaaca taaaaataaa taaacacaga gtaaattccc aaattattcc atcattaaaa | 6660 |
| gatacgaggc gcgtgtaagt tacaggcaag cgatccgtcc taagaaacca ttattatcat | 6720 |
| gacattaacc tataaaaata ggcgtatcac gaggcccttt cgtc | 6764 |

<210> SEQ ID NO 36
<211> LENGTH: 1638
<212> TYPE: DNA
<213> ORGANISM: Quercus ilex
<220> FEATURE:
<221> NAME/KEY: misc_feature
<223> OTHER INFORMATION: Quercus ilex myrcene synthase nucleic acid
      encoding "QiMS" (codon optimized for S. cerevisiae)

<400> SEQUENCE: 36

| | |
|---|---|
| atggctattt tgagaagatc cgctaactac caaccttcta tttggaacca tgactacatt | 60 |
| gaatctttga gaattgaata cgttggtgaa acctgtacca gacaaattaa cgttttgaaa | 120 |
| gaacaagtca gaatgatgtt gcacaaagtc gttaacccat ggaacaatt ggaattgatt | 180 |
| gaaatcttac aaagattagg tttatcttac catttcgaag aagaaatcaa gagaatcttg | 240 |
| gacggtgtct acaacaatga ccatggtggt gatacctgga aggctgaaaa cttgtacgct | 300 |
| accgctttga gttcagatt gttgagacaa cacggttact ctgtttccca gaagttttt | 360 |
| aactccttca aggacgaaag aggttccttt aaggcttgtt tgtgtgagga taccaagggt | 420 |
| atgttgtcct tgtatgaagc ttctttcttc ttgattgaag gtgaaaatat tttggaagaa | 480 |
| gcccgtgact tctctactaa gcacttagaa gaatatgtca agcaaaataa ggaaaagaac | 540 |
| ttagctactt tggtcaacca ctccttagaa ttcccattgc attggagaat gcctcgtttg | 600 |
| gaagccagat ggttcatcaa catttataga cataaccaag atgttaaccc aattttgtta | 660 |
| gagttcgctg aattggattt caacattgtt caagccgccc accaagctga cttgaagcaa | 720 |
| gtttctacct ggtggaagtc caccggtttg gttgaaaact tgtctttcgc cagagacaga | 780 |
| ccagttgaaa atttcttctg gactgtcggt tgatctttc aaccacaatt cggttactgt | 840 |
| cgtagaatgt tcactaaagt tttcgctttg atcactacca ttgacgacgt ctacgacgtt | 900 |
| tacggtactt tggacgaatt ggaattgttc actgatgtcg tcgaaagatg ggacatcaac | 960 |
| gccatggatc aattgccaga ttacatgaag atctgtttct tgaccttgca caactccgtc | 1020 |
| aacgaaatgg ctttggatac catgaaggag caaagattcc atattattaa gtatttgaag | 1080 |
| aaggcttggg ttgatttgtg tagatactac ttggttgaag ctaaatggta ctccaacaag | 1140 |
| tacagaccat ccttgcaaga gtatattgaa aacgcttgga tttccatcgg tgccccaact | 1200 |
| attttggtcc acgcttactt tttcgttacc aaccctatta ccaaggaagc cttggactgt | 1260 |
| ttggaagaat acccaaacat tattagatgg tcctccatca ttgccagatt agctgatgat | 1320 |
| ttgggtacct ccactgatga gttgaaaaga ggtgacgtcc taaggctat tcaatgttat | 1380 |
| atgaatgaga ctggtgcctc cgaagaaggt gctagagaat acattaaata cttgatttct | 1440 |
| gctacttgga gaagatgaa caaagataga gctgcttctt ctccattctc tcatattttt | 1500 |
| atcgaaattg ctttgaactt ggctagaatg gctcaatgtt tgtatcaaca cggtgacggt | 1560 |
| cacggtttgg gtaaccgtga aaccaaagat cgtatttgt ccttgttgat ccaaccaatc | 1620 |
| cctttaaaca aggactaa | 1638 |

<210> SEQ ID NO 37

-continued

```
<211> LENGTH: 44
<212> TYPE: DNA
<213> ORGANISM: Artificial Sequence
<220> FEATURE:
<223> OTHER INFORMATION: Synthetic: AM-405 primer

<400> SEQUENCE: 37
cgtcaaggag aaaaaacccc ggatccatgg ttgaacaccg acgc               44

<210> SEQ ID NO 38
<211> LENGTH: 24
<212> TYPE: DNA
<213> ORGANISM: Artificial Sequence
<220> FEATURE:
<223> OTHER INFORMATION: Synthetic: AM-168 primer

<400> SEQUENCE: 38
gcaaggtttt cagtataatg ttac                                     24

<210> SEQ ID NO 39
<211> LENGTH: 210
<212> TYPE: DNA
<213> ORGANISM: Artificial Sequence
<220> FEATURE:
<223> OTHER INFORMATION: Synthetic: Mrycomb1_2A

<400> SEQUENCE: 39
caattgccat cttacatgca attgtgctat ttggccattt ataacttcgt ctccgaattg     60
gcttacgaca ttttccgtga taagggtttc aactctttac catacttgca caagtcttgg   120
ttggatttgg ttgaagctta tttcgttgaa gccaagtggt tccacgacgg ttacactcca   180
actttggaag aatacttgaa caactctaag                                     210

<210> SEQ ID NO 40
<211> LENGTH: 210
<212> TYPE: DNA
<213> ORGANISM: Artificial Sequence
<220> FEATURE:
<223> OTHER INFORMATION: Synthetic: Mrycomb1_2B

<400> SEQUENCE: 40
caattgccat cttacatgca attgtgctat ttggccattt ataacttcgt ctccgaattg     60
gcttacgaca ttttccgtga taagggtttc aactctttac catacttgca caagtcttgg   120
ttggatttgg ttgaagctta tcttgttgaa gccaagtggt tccacgacgg ttacactcca   180
actttggaag aatacttgaa caactctaag                                     210

<210> SEQ ID NO 41
<211> LENGTH: 210
<212> TYPE: DNA
<213> ORGANISM: Artificial Sequence
<220> FEATURE:
<223> OTHER INFORMATION: Synthetic: Mrycomb1_2C

<400> SEQUENCE: 41
caattgccat cttacatgca attgtgctat ttggccattt ataacttcgt ctccgaattg     60
gcttacgaca ttttccgtga taagggtttc aactctttac catacttgca caagtcttgg   120
ttggatttgg ttgaagctta tttcgttgaa gccaagtggt tccacggtgg ttacactcca   180
actttggaag aatacttgaa caactctaag                                     210

<210> SEQ ID NO 42
<211> LENGTH: 210
```

```
<212> TYPE: DNA
<213> ORGANISM: Artificial Sequence
<220> FEATURE:
<223> OTHER INFORMATION: Synthetic: Mrycomb1_2D

<400> SEQUENCE: 42
caattgccat cttacatgca attgtgctat ttggccattt ataacttcgt ctccgaattg      60
gcttacgaca ttttccgtga taagggtttc aactctttac catacttgca caagtcttgg     120
ttggatttgg ttgaagctta tcttgttgaa gccaagtggt tccacggtgg ttacactcca     180
actttggaag aatacttgaa caactctaag                                      210

<210> SEQ ID NO 43
<211> LENGTH: 414
<212> TYPE: DNA
<213> ORGANISM: Artificial Sequence
<220> FEATURE:
<223> OTHER INFORMATION: Synthetic: Mrycomb1_3A

<400> SEQUENCE: 43
ggttacactc caactttgga agaatacttg aacaactcta agattactat catttgtcca      60
gccatcgttt ccgaaattta cttcgctttt gccaactcta tcgataagac tgaagttgaa     120
tccatttaca agtatcacga catttttgtac ttgtccggta tgttggctag attgccagac    180
gatttgggta cctcttcctt cgagatgaag cgtggtgacg ttgctaaggc cattcaatgt     240
tacatgaagg aacacaacgc ctctgaggaa gaagctagag aacatattcg tttcttgatg     300
agagaagctt ggaagcacat gaacactgcc gctgctgccg atgactgtcc atttgaatct     360
gacttggttg ttggtgctgc ctccttgggt agagtcgcta acttcgtcta cgtt           414

<210> SEQ ID NO 44
<211> LENGTH: 414
<212> TYPE: DNA
<213> ORGANISM: Artificial Sequence
<220> FEATURE:
<223> OTHER INFORMATION: Synthetic: Mrycomb1_3B

<400> SEQUENCE: 44
ggttacactc caactttgga agaatacttg aacaactcta aggttactat catttgtcca      60
gccatcgttt ccgaaattta cttcgctttt gccaactcta tcgataagac tgaagttgaa     120
tccatttaca agtatcacga catttttgtac ttgtccggta tgttggctag attgccagac    180
gatttgggta cctcttcctt cgagatgaag cgtggtgacg ttgctaaggc cattcaatgt     240
tacatgaagg aacacaacgc ctctgaggaa gaagctagag aacatattcg tttcttgatg     300
agagaagctt ggaagcacat gaacactgcc gctgctgccg atgactgtcc atttgaatct     360
gacttggttg ttggtgctgc ctccttgggt agagtcgcta acttcgtcta cgtt           414

<210> SEQ ID NO 45
<211> LENGTH: 414
<212> TYPE: DNA
<213> ORGANISM: Artificial Sequence
<220> FEATURE:
<223> OTHER INFORMATION: Synthetic: Mrycomb1_3C

<400> SEQUENCE: 45
ggttacactc caactttgga agaatacttg aacaactcta agattactat catttgtcca      60
gccatcgttt ccgaaattta cttcgctttt gccaactcta tcgataagac tgaagttgaa     120
tccatttaca agtatcacga catttttgctt ttgtccggta tgttggctag attgccagac    180
```

```
gatttgggta cctcttcctt cgagatgaag cgtggtgacg ttgctaaggc cattcaatgt      240
tacatgaagg aacacaacgc ctctgaggaa gaagctagag aacatattcg tttcttgatg      300
agagaagctt ggaagcacat gaacactgcc gctgctgccg atgactgtcc atttgaatct      360
gacttggttg ttggtgctgc ctccttgggt agagtcgcta acttcgtcta cgtt            414

<210> SEQ ID NO 46
<211> LENGTH: 414
<212> TYPE: DNA
<213> ORGANISM: Artificial Sequence
<220> FEATURE:
<223> OTHER INFORMATION: Synthetic: Mrycomb1_3D

<400> SEQUENCE: 46
ggttacactc caactttgga agaatacttg aacaactcta agattactat catttgtcca       60
gccatcgttt ccgaaattta cttcgctttt gccaactcta tcgataagac tgaagttgaa      120
tccatttaca agtatcacga catttttgtac ttgtccggta tgttggctag attgccagac     180
gatttgggta cctcttcctt cgagatgaag cgtggtgacg ttgctaaggc cattcaatgt      240
tacatgaagg aacacaacgc ctctgaggaa gaagctattg aacatattcg tttcttgatg      300
agagaagctt ggaagcacat gaacactgcc gctgctgccg atgactgtcc atttgaatct      360
gacttggttg ttggtgctgc ctccttgggt agagtcgcta acttcgtcta cgtt            414

<210> SEQ ID NO 47
<211> LENGTH: 414
<212> TYPE: DNA
<213> ORGANISM: Artificial Sequence
<220> FEATURE:
<223> OTHER INFORMATION: Synthetic: Mrycomb1_3E

<400> SEQUENCE: 47
ggttacactc caactttgga agaatacttg aacaactcta aggttactat catttgtcca       60
gccatcgttt ccgaaattta cttcgctttt gccaactcta tcgataagac tgaagttgaa      120
tccatttaca agtatcacga catttttgctt ttgtccggta tgttggctag attgccagac     180
gatttgggta cctcttcctt cgagatgaag cgtggtgacg ttgctaaggc cattcaatgt      240
tacatgaagg aacacaacgc ctctgaggaa gaagctagag aacatattcg tttcttgatg      300
agagaagctt ggaagcacat gaacactgcc gctgctgccg atgactgtcc atttgaatct      360
gacttggttg ttggtgctgc ctccttgggt agagtcgcta acttcgtcta cgtt            414

<210> SEQ ID NO 48
<211> LENGTH: 414
<212> TYPE: DNA
<213> ORGANISM: Artificial Sequence
<220> FEATURE:
<223> OTHER INFORMATION: Synthetic: Mrycomb1_3F

<400> SEQUENCE: 48
ggttacactc caactttgga agaatacttg aacaactcta aggttactat catttgtcca       60
gccatcgttt ccgaaattta cttcgctttt gccaactcta tcgataagac tgaagttgaa      120
tccatttaca agtatcacga catttttgtac ttgtccggta tgttggctag attgccagac     180
gatttgggta cctcttcctt cgagatgaag cgtggtgacg ttgctaaggc cattcaatgt      240
tacatgaagg aacacaacgc ctctgaggaa gaagctattg aacatattcg tttcttgatg      300
agagaagctt ggaagcacat gaacactgcc gctgctgccg atgactgtcc atttgaatct      360
gacttggttg ttggtgctgc ctccttgggt agagtcgcta acttcgtcta cgtt            414
```

<210> SEQ ID NO 49
<211> LENGTH: 414
<212> TYPE: DNA
<213> ORGANISM: Artificial Sequence
<220> FEATURE:
<223> OTHER INFORMATION: Synthetic: Mrycomb1_3G

<400> SEQUENCE: 49

```
ggttacactc caactttgga agaatacttg aacaactcta agattactat catttgtcca      60
gccatcgttt ccgaaattta cttcgctttt gccaactcta tcgataagac tgaagttgaa     120
tccatttaca agtatcacga catttttgctt ttgtccggta tgttggctag attgccagac    180
gatttgggta cctcttcctt cgagatgaag cgtggtgacg ttgctaaggc cattcaatgt     240
tacatgaagg aacacaacgc ctctgaggaa gaagctattg aacatattcg tttcttgatg     300
agagaagctt ggaagcacat gaacactgcc gctgctgccg atgactgtcc atttgaatct    360
gacttggttg ttggtgctgc ctccttgggt agagtcgcta acttcgtcta cgtt          414
```

<210> SEQ ID NO 50
<211> LENGTH: 414
<212> TYPE: DNA
<213> ORGANISM: Artificial Sequence
<220> FEATURE:
<223> OTHER INFORMATION: Synthetic: Mrycomb1_3H

<400> SEQUENCE: 50

```
ggttacactc caactttgga agaatacttg aacaactcta aggttactat catttgtcca     60
gccatcgttt ccgaaattta cttcgctttt gccaactcta tcgataagac tgaagttgaa    120
tccatttaca agtatcacga catttttgctt ttgtccggta tgttggctag attgccagac   180
gatttgggta cctcttcctt cgagatgaag cgtggtgacg ttgctaaggc cattcaatgt    240
tacatgaagg aacacaacgc ctctgaggaa gaagctattg aacatattcg tttcttgatg    300
agagaagctt ggaagcacat gaacactgcc gctgctgccg atgactgtcc atttgaatct   360
gacttggttg ttggtgctgc ctccttgggt agagtcgcta acttcgtcta cgtt         414
```

<210> SEQ ID NO 51
<211> LENGTH: 273
<212> TYPE: DNA
<213> ORGANISM: Artificial Sequence
<220> FEATURE:
<223> OTHER INFORMATION: Synthetic: Mrycomb1_4A

<400> SEQUENCE: 51

```
gaacatattc gtttcttgat gagagaagct tggaagcaca tgaacactgc cgctgctgcc      60
gatgactgtc catttgaatc tgacttggtt gttggtgctg cctccttggg tagagtcgct     120
aacttcgtct acgttgaggg tgatggtttc ggtgtccaac actctaagat tcaccaacaa     180
atggctgaat tattgtttta cccataccaa taagctagct aagatccgct ctaaccgaaa     240
aggaaggagt tagacaacct gaagtctagg tcc                                  273
```

<210> SEQ ID NO 52
<211> LENGTH: 273
<212> TYPE: DNA
<213> ORGANISM: Artificial Sequence
<220> FEATURE:
<223> OTHER INFORMATION: Synthetic: Mrycomb1_4B

<400> SEQUENCE: 52

```
gaacatattc gtttcttgat gagagaagct tggaagcaca tgaacactgc cgctgctgcc      60
gatgactgtc catttgaatc tgacttggtt gttggtgctg cctccttggg tagagtcgct     120
aacttcgtct acgttgatgg tgatggtttc ggtgtccaac actctaagat tcaccaacaa     180
atggctgaat tattgtttta cccataccaa taagctagct aagatccgct ctaaccgaaa     240
aggaaggagt tagacaacct gaagtctagg tcc                                  273
```

<210> SEQ ID NO 53
<211> LENGTH: 273
<212> TYPE: DNA
<213> ORGANISM: Artificial Sequence
<220> FEATURE:
<223> OTHER INFORMATION: Synthetic: Mrycomb1_4C

<400> SEQUENCE: 53

```
gaacatattc gtttcttgat gagagaagct tggaagcaca tgaacactgc cgctgctgcc      60
gatgactgtc catttgaatc tgacttggtt gttggtgctg cctccttggg tagagtcgct     120
aacttcgtct acgttgaggg tgatggtttc ggtgtccaac actctaagat tcaccaacaa     180
attgctgaat tattgtttta cccataccaa taagctagct aagatccgct ctaaccgaaa     240
aggaaggagt tagacaacct gaagtctagg tcc                                  273
```

<210> SEQ ID NO 54
<211> LENGTH: 273
<212> TYPE: DNA
<213> ORGANISM: Artificial Sequence
<220> FEATURE:
<223> OTHER INFORMATION: Synthetic: Mrycomb1_4D

<400> SEQUENCE: 54

```
gaacatattc gtttcttgat gagagaagct tggaagcaca tgaacactgc cgctgctgcc      60
gatgactgtc catttgaatc tgacttggtt gttggtgctg cctccttggg tagagtcgct     120
aacttcgtct acgttgatgg tgatggtttc ggtgtccaac actctaagat tcaccaacaa     180
attgctgaat tattgtttta cccataccaa taagctagct aagatccgct ctaaccgaaa     240
aggaaggagt tagacaacct gaagtctagg tcc                                  273
```

<210> SEQ ID NO 55
<211> LENGTH: 50
<212> TYPE: DNA
<213> ORGANISM: Artificial Sequence
<220> FEATURE:
<223> OTHER INFORMATION: Synthetic: Primer 484-1F
<220> FEATURE:
<221> NAME/KEY: misc_feature
<222> LOCATION: (23)..(23)
<223> OTHER INFORMATION: n is a, c, g, or t

<400> SEQUENCE: 55

```
ctcagaggag gaggcacgtg agndtatcag atttcttatg cgggaggcgt                 50
```

<210> SEQ ID NO 56
<211> LENGTH: 22
<212> TYPE: DNA
<213> ORGANISM: Artificial Sequence
<220> FEATURE:
<223> OTHER INFORMATION: Synthetic: Primer 484-1R

<400> SEQUENCE: 56

```
ctcacgtgcc tcctcctctg ag                                              22
```

```
<210> SEQ ID NO 57
<211> LENGTH: 30
<212> TYPE: DNA
<213> ORGANISM: Artificial Sequence
<220> FEATURE:
<223> OTHER INFORMATION: Synthetic: Primer 27-IF

<400> SEQUENCE: 57
tccaaggaag aacgtcattt ggaaagaaag                                          30

<210> SEQ ID NO 58
<211> LENGTH: 60
<212> TYPE: DNA
<213> ORGANISM: Artificial Sequence
<220> FEATURE:
<223> OTHER INFORMATION: Synthetic: Primer 27-IR
<220> FEATURE:
<221> NAME/KEY: misc_feature
<222> LOCATION: (30)..(30)
<223> OTHER INFORMATION: n is a, c, g, or t

<400> SEQUENCE: 58
tctttccaaa tgacgttctt ccttggaahn gttgttgttc aaggattgaa tgtaattaaa         60

<210> SEQ ID NO 59
<211> LENGTH: 30
<212> TYPE: DNA
<213> ORGANISM: Artificial Sequence
<220> FEATURE:
<223> OTHER INFORMATION: Synthetic: Primer 28-IF

<400> SEQUENCE: 59
aaggaagaac gtcatttgga agaaaggct                                           30

<210> SEQ ID NO 60
<211> LENGTH: 60
<212> TYPE: DNA
<213> ORGANISM: Artificial Sequence
<220> FEATURE:
<223> OTHER INFORMATION: Synthetic: Primer 28-IR
<220> FEATURE:
<221> NAME/KEY: misc_feature
<222> LOCATION: (30)..(30)
<223> OTHER INFORMATION: n is a, c, g, or t

<400> SEQUENCE: 60
ctttctttcc aaatgacgtt cttccttahn atggttgttg ttcaaggatt gaatgtaatt         60

<210> SEQ ID NO 61
<211> LENGTH: 28
<212> TYPE: DNA
<213> ORGANISM: Artificial Sequence
<220> FEATURE:
<223> OTHER INFORMATION: Synthetic: Primer 207-IF

<400> SEQUENCE: 61
caaagattgg aggccaaatg gttcttgg                                            28

<210> SEQ ID NO 62
<211> LENGTH: 60
<212> TYPE: DNA
<213> ORGANISM: Artificial Sequence
<220> FEATURE:
<223> OTHER INFORMATION: Synthetic: Primer 207-IR
<220> FEATURE:
<221> NAME/KEY: misc_feature
<222> LOCATION: (30)..(30)
<223> OTHER INFORMATION: n is a, c, g, or t
```

<400> SEQUENCE: 62
caagaaccat ttggcctcca atctttgahn tctccaatgc aaaggtaact ccaaagagtg    60

<210> SEQ ID NO 63
<211> LENGTH: 30
<212> TYPE: DNA
<213> ORGANISM: Artificial Sequence
<220> FEATURE:
<223> OTHER INFORMATION: Synthetic: Primer 222-IF

<400> SEQUENCE: 63
ccagatatga acccaattat tttcgaattg    30

<210> SEQ ID NO 64
<211> LENGTH: 56
<212> TYPE: DNA
<213> ORGANISM: Artificial Sequence
<220> FEATURE:
<223> OTHER INFORMATION: Synthetic: Primer 222-IR
<220> FEATURE:
<221> NAME/KEY: misc_feature
<222> LOCATION: (33)..(33)
<223> OTHER INFORMATION: n is a, c, g, or t

<400> SEQUENCE: 64
caattcgaaa ataattgggt tcatatctgg ahnagaggcg taggcatcca agaacc    56

<210> SEQ ID NO 65
<211> LENGTH: 60
<212> TYPE: DNA
<213> ORGANISM: Artificial Sequence
<220> FEATURE:
<223> OTHER INFORMATION: Synthetic: Primer 342-IF
<220> FEATURE:
<221> NAME/KEY: misc_feature
<222> LOCATION: (28)..(28)
<223> OTHER INFORMATION: n is a, c, g, or t

<400> SEQUENCE: 65
aaccaattgc catcttacat gcaattgndt tatttggcca tttataactt cgtctccgaa    60

<210> SEQ ID NO 66
<211> LENGTH: 30
<212> TYPE: DNA
<213> ORGANISM: Artificial Sequence
<220> FEATURE:
<223> OTHER INFORMATION: Synthetic: Primer 342-IR

<400> SEQUENCE: 66
caattgcatg taagatggca attggttgat    30

<210> SEQ ID NO 67
<211> LENGTH: 59
<212> TYPE: DNA
<213> ORGANISM: Artificial Sequence
<220> FEATURE:
<223> OTHER INFORMATION: Synthetic: Primer 347-IF
<220> FEATURE:
<221> NAME/KEY: misc_feature
<222> LOCATION: (31)..(31)
<223> OTHER INFORMATION: n is a, c, g, or t

<400> SEQUENCE: 67
tcttacatgc aattgtgcta tttggccatt ndtaacttcg tctccgaatt ggcttacga    59

<210> SEQ ID NO 68
<211> LENGTH: 30

-continued

<212> TYPE: DNA
<213> ORGANISM: Artificial Sequence
<220> FEATURE:
<223> OTHER INFORMATION: Synthetic: Primer 347-IR

<400> SEQUENCE: 68
aatggccaaa tagcacaatt gcatgtaaga                                        30

<210> SEQ ID NO 69
<211> LENGTH: 55
<212> TYPE: DNA
<213> ORGANISM: Artificial Sequence
<220> FEATURE:
<223> OTHER INFORMATION: Synthetic: Primer 382-IF
<220> FEATURE:
<221> NAME/KEY: misc_feature
<222> LOCATION: (31)..(31)
<223> OTHER INFORMATION: n is a, c, g, or t

<400> SEQUENCE: 69
tcttggttgg atttggttga agcttatttc ndtgaagcca agtggttcca cgacg           55

<210> SEQ ID NO 70
<211> LENGTH: 30
<212> TYPE: DNA
<213> ORGANISM: Artificial Sequence
<220> FEATURE:
<223> OTHER INFORMATION: Synthetic: Primer 382-IR

<400> SEQUENCE: 70
gaaataagct tcaaccaaat ccaaccaaga                                        30

<210> SEQ ID NO 71
<211> LENGTH: 56
<212> TYPE: DNA
<213> ORGANISM: Artificial Sequence
<220> FEATURE:
<223> OTHER INFORMATION: Synthetic: Primer 390-IF
<220> FEATURE:
<221> NAME/KEY: misc_feature
<222> LOCATION: (24)..(24)
<223> OTHER INFORMATION: n is a, c, g, or t

<400> SEQUENCE: 71
ttgaagccaa gtggttccac gacndttaca ctccaacttt ggaagaatac ttgaac          56

<210> SEQ ID NO 72
<211> LENGTH: 45
<212> TYPE: DNA
<213> ORGANISM: Artificial Sequence
<220> FEATURE:
<223> OTHER INFORMATION: Synthetic: Primer

<400> SEQUENCE: 72
gtcgtggaac cacttggctt caactcacgt gcctcctcct ctgag                       45

<210> SEQ ID NO 73
<211> LENGTH: 60
<212> TYPE: DNA
<213> ORGANISM: Artificial Sequence
<220> FEATURE:
<223> OTHER INFORMATION: Synthetic: Primer 401-IF
<220> FEATURE:
<221> NAME/KEY: misc_feature
<222> LOCATION: (28)..(28)
<223> OTHER INFORMATION: n is a, c, g, or t

<400> SEQUENCE: 73
actccaactt tggaagaata cttgaacndt tctaagatta ctatcatttg tccagccatc    60

<210> SEQ ID NO 74
<211> LENGTH: 30
<212> TYPE: DNA
<213> ORGANISM: Artificial Sequence
<220> FEATURE:
<223> OTHER INFORMATION: Synthetic: Primer 401-IR

<400> SEQUENCE: 74
gttcaagtat tcttccaaag ttggagtgta                                     30

<210> SEQ ID NO 75
<211> LENGTH: 60
<212> TYPE: DNA
<213> ORGANISM: Artificial Sequence
<220> FEATURE:
<223> OTHER INFORMATION: Synthetic: Primer 428-IF
<220> FEATURE:
<221> NAME/KEY: misc_feature
<222> LOCATION: (28)..(28)
<223> OTHER INFORMATION: n is a, c, g, or t

<400> SEQUENCE: 75
tttgccaact ctatcgataa gactgaandt gaatccattt acaagtatca cgacattttg    60

<210> SEQ ID NO 76
<211> LENGTH: 30
<212> TYPE: DNA
<213> ORGANISM: Artificial Sequence
<220> FEATURE:
<223> OTHER INFORMATION: Synthetic: Primer 428-IR

<400> SEQUENCE: 76
ttcagtctta tcgatagagt tggcaaaagc                                     30

<210> SEQ ID NO 77
<211> LENGTH: 58
<212> TYPE: DNA
<213> ORGANISM: Artificial Sequence
<220> FEATURE:
<223> OTHER INFORMATION: Synthetic: Primer 466-IF
<220> FEATURE:
<221> NAME/KEY: misc_feature
<222> LOCATION: (26)..(26)
<223> OTHER INFORMATION: n is a, c, g, or t

<400> SEQUENCE: 77
gatgaagcgt ggtgacgttg ctaagndtat tcaatgttac atgaaggaac acaacgcc     58

<210> SEQ ID NO 78
<211> LENGTH: 25
<212> TYPE: DNA
<213> ORGANISM: Artificial Sequence
<220> FEATURE:
<223> OTHER INFORMATION: Synthetic: Primer 466-IR

<400> SEQUENCE: 78
cttagcaacg tcaccacgct tcatc                                          25

<210> SEQ ID NO 79
<211> LENGTH: 52
<212> TYPE: DNA
<213> ORGANISM: Artificial Sequence
<220> FEATURE:
<223> OTHER INFORMATION: Synthetic: Primer 505-IF
<220> FEATURE:
<221> NAME/KEY: misc_feature

```
<222> LOCATION: (21)..(21)
<223> OTHER INFORMATION: n is a, c, g, or t

<400> SEQUENCE: 79
ctgccgctgc tgccgatgac ndtccatttg aatctgactt ggttgttggt gc          52

<210> SEQ ID NO 80
<211> LENGTH: 20
<212> TYPE: DNA
<213> ORGANISM: Artificial Sequence
<220> FEATURE:
<223> OTHER INFORMATION: Synthetic: Primer 505-IR

<400> SEQUENCE: 80
gtcatcggca gcagcggcag                                              20

<210> SEQ ID NO 81
<211> LENGTH: 54
<212> TYPE: DNA
<213> ORGANISM: Artificial Sequence
<220> FEATURE:
<223> OTHER INFORMATION: Synthetic: Primer 514-IF
<220> FEATURE:
<221> NAME/KEY: misc_feature
<222> LOCATION: (31)..(31)
<223> OTHER INFORMATION: n is a, c, g, or t

<400> SEQUENCE: 81
gactgtccat ttgaatctga cttggttgtt ndtgctgcct ccttgggtag agtc        54

<210> SEQ ID NO 82
<211> LENGTH: 30
<212> TYPE: DNA
<213> ORGANISM: Artificial Sequence
<220> FEATURE:
<223> OTHER INFORMATION: Synthetic: Primer 514-IR

<400> SEQUENCE: 82
aacaaccaag tcagattcaa atggacagtc                                   30

<210> SEQ ID NO 83
<211> LENGTH: 53
<212> TYPE: DNA
<213> ORGANISM: Artificial Sequence
<220> FEATURE:
<223> OTHER INFORMATION: Synthetic: Primer 517-IF
<220> FEATURE:
<221> NAME/KEY: misc_feature
<222> LOCATION: (24)..(24)
<223> OTHER INFORMATION: n is a, c, g, or t

<400> SEQUENCE: 83
ctgacttggt tgttggtgct gccndtttgg gtagagtcgc taacttcgtc tac         53

<210> SEQ ID NO 84
<211> LENGTH: 23
<212> TYPE: DNA
<213> ORGANISM: Artificial Sequence
<220> FEATURE:
<223> OTHER INFORMATION: Synthetic: Primer 517-IR

<400> SEQUENCE: 84
ggcagcacca acaaccaagt cag                                          23

<210> SEQ ID NO 85
<211> LENGTH: 51
<212> TYPE: DNA
```

```
<213> ORGANISM: Artificial Sequence
<220> FEATURE:
<223> OTHER INFORMATION: Synthetic: Primer 524-IF
<220> FEATURE:
<221> NAME/KEY: misc_feature
<222> LOCATION: (25)..(25)
<223> OTHER INFORMATION: n is a, c, g, or t

<400> SEQUENCE: 85
gcctccttgg gtagagtcgc taacndtgtc tacgttgagg gtgatggttt c          51

<210> SEQ ID NO 86
<211> LENGTH: 24
<212> TYPE: DNA
<213> ORGANISM: Artificial Sequence
<220> FEATURE:
<223> OTHER INFORMATION: Synthetic: Primer 524-IR

<400> SEQUENCE: 86
gttagcgact ctacccaagg aggc                                         24

<210> SEQ ID NO 87
<211> LENGTH: 52
<212> TYPE: DNA
<213> ORGANISM: Artificial Sequence
<220> FEATURE:
<223> OTHER INFORMATION: Synthetic: Primer 527-IF
<220> FEATURE:
<221> NAME/KEY: misc_feature
<222> LOCATION: (29)..(29)
<223> OTHER INFORMATION: n is a, c, g, or t

<400> SEQUENCE: 87
cttgggtaga gtcgctaact cgtctacnd tgagggtgat ggtttcggtg tc          52

<210> SEQ ID NO 88
<211> LENGTH: 28
<212> TYPE: DNA
<213> ORGANISM: Artificial Sequence
<220> FEATURE:
<223> OTHER INFORMATION: Synthetic: Primer 527-IR

<400> SEQUENCE: 88
gtagacgaag ttagcgactc tacccaag                                     28
```